US012697324B2

(12) United States Patent
Qiao et al.

(10) Patent No.: US 12,697,324 B2
(45) Date of Patent: Aug. 4, 2026

(54) USE OF COMPOUND AS CYP2E1 INHIBITOR

(71) Applicant: Suzhou Lingxi Biotechnology Co., Ltd., Suzhou (CN)

(72) Inventors: Hailing Qiao, Zhengzhou (CN); Haiwei Xu, Zhengzhou (CN); Yan Fang, Zhengzhou (CN); Na Gao, Zhengzhou (CN); Qiang Wen, Zhengzhou (CN); Shufeng Li, Zhengzhou (CN)

(73) Assignee: Suzhou Lingxi Biotechnology Co., Ltd., Suzhou (CN)

( * ) Notice: Subject to any disclaimer, the term of this patent is extended or adjusted under 35 U.S.C. 154(b) by 596 days.

(21) Appl. No.: 18/024,070

(22) PCT Filed: Oct. 29, 2021

(86) PCT No.: PCT/CN2021/127710

§ 371 (c)(1),
(2) Date: Mar. 1, 2023

(87) PCT Pub. No.: WO2022/048695

PCT Pub. Date: Mar. 10, 2022

(65) Prior Publication Data

US 2023/0277508 A1 Sep. 7, 2023

(30) Foreign Application Priority Data

Sep. 1, 2020 (CN) ......................... 202010906508.3

(51) Int. Cl.

| | |
|---|---|
| ***A61K 31/426*** | (2006.01) |
| ***A61K 31/427*** | (2006.01) |
| ***A61K 31/4439*** | (2006.01) |
| ***A61K 31/497*** | (2006.01) |
| ***A61K 31/5377*** | (2006.01) |
| ***A61P 1/16*** | (2006.01) |
| ***A61P 3/06*** | (2006.01) |
| ***A61P 3/10*** | (2006.01) |
| ***A61P 9/10*** | (2006.01) |
| ***A61P 11/00*** | (2006.01) |
| ***A61P 25/28*** | (2006.01) |
| ***A61P 29/00*** | (2006.01) |
| ***A61P 31/04*** | (2006.01) |
| ***A61P 35/00*** | (2006.01) |

(52) U.S. Cl.

CPC .......... *A61K 31/426* (2013.01); *A61K 31/427* (2013.01); *A61K 31/4439* (2013.01); *A61K 31/497* (2013.01); *A61K 31/5377* (2013.01); *A61P 1/16* (2018.01); *A61P 3/06* (2018.01); *A61P 3/10* (2018.01); *A61P 9/10* (2018.01); *A61P 11/00* (2018.01); *A61P 25/28* (2018.01); *A61P 29/00* (2018.01); *A61P 31/04* (2018.01); *A61P 35/00* (2018.01)

(58) Field of Classification Search

CPC .... A61P 9/10; A61P 25/28; A61P 1/16; A61P 35/00; A61P 29/00; A61P 11/00; A61P 3/06; A61P 3/10; A61P 31/04; A61P 31/427; A61P 31/4439; A61P 31/497

See application file for complete search history.

(56) References Cited

FOREIGN PATENT DOCUMENTS

| | | | | |
|---|---|---|---|---|
| CN | 1276789 A | | 12/2000 | |
| CN | 101921269 | * | 12/2010 | ........... C07D 417/14 |
| CN | 101921269 A | | 12/2010 | |
| CN | 105769860 | * | 4/2016 | ........... A61K 31/426 |
| CN | 105664181 A | | 6/2016 | |
| CN | 105769860 A | | 7/2016 | |

OTHER PUBLICATIONS

Anke C. Gebhardt et al., Chlormethiazole Inhibition of Cytochrome P450 2E1 As Assessed by Chlorzoxazone Hydroxylation in Humans, Hepatology, 1997-10-31, pp. 957-961.
Jianbin Wang et al., Inhibitory effect of Clormethiazole on ethanol-induced liver injury in rats, China Journal of Modern Medicine, Sep. 30, 2018, pp. 14-21, vol. 28 No. 26.
Na Gao, et al., Concentration-Dependent Inhibitory Effect of Baicalin on the Plasma Protein Binding and Metabolism of Chlorzoxazone, a CYP2E1 Probe Substrate, in Rats In Vitro and In Vivo, PLOS ONE, 2013, pp. 1-9, vol. 8, Issue 1, e53038.
What Don't We Know? Science, 2005, pp. 78-102, vol. 309, AAAS.
Sergei I. Grivennikov, et al., Immunity, Inflammation, and Cancer, Cell, 2010, pp. 883-899, vol. 140.
Atamjit Singh, et al., Thiazole derivatives in medicinal chemistry: Recent advancements in synthetic strategies, Structure activity relationship and pharmacological outcomes; Journal of Molecular Structure, 2022, pp. 1-89, vol. 1266, 133479.

* cited by examiner

*Primary Examiner* — Erich A Leeser
(74) *Attorney, Agent, or Firm* — Kilpatrick Townsend & Stockton LLP

(57) ABSTRACT

A use of a compound as a CYP2E1 inhibitor includes: using a compound shown in formula (I) or a salt thereof as an inhibitor to inhibit CYP2E1, where the compound or the salt thereof targets and binds to CYP2E1. The inhibitor can be used for the prevention and treatment of a tumor including liver cancer, glioma, ovarian cancer, lung cancer, bladder cancer, and gallbladder cancer. The inhibitor can also be used for the prevention and treatment of an inflammation-mediated disease (IMD) such as liver damage, fatty liver, hepatitis, liver fibrosis, pulmonary fibrosis, rheumatic and rheumatoid arthritis, sepsis, Alzheimer's disease (AD), ischemic stroke, Parkinson's disease (PD), hyperlipidemia, atherosclerosis (AS), coronary heart disease (CHD), and diabetes.

7 Claims, 46 Drawing Sheets

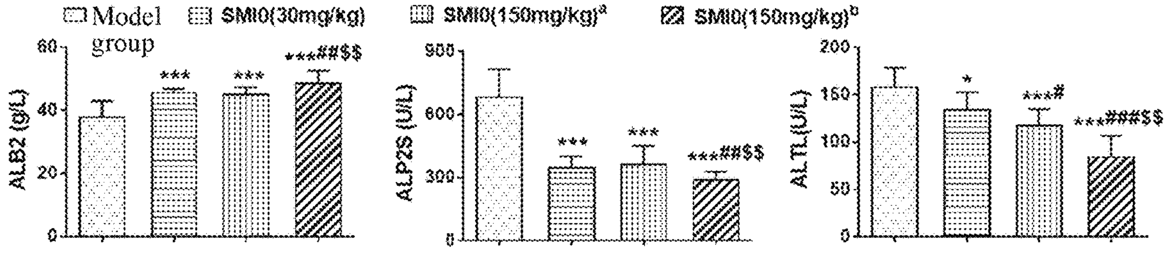
FIG. 13A
FIG. 13B
FIG. 13C
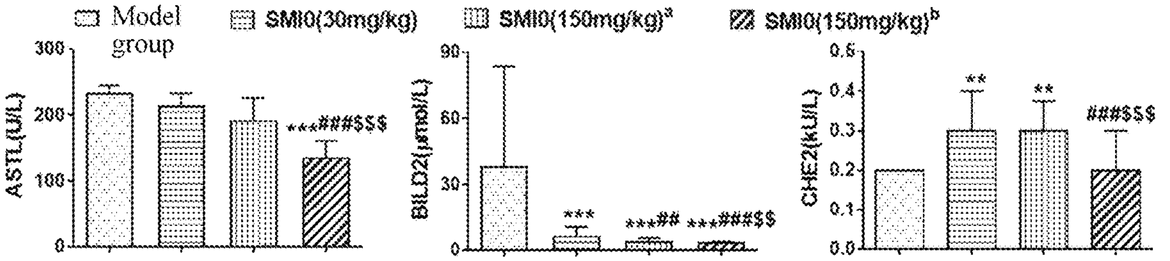
FIG. 13D
FIG. 13E
FIG. 13F
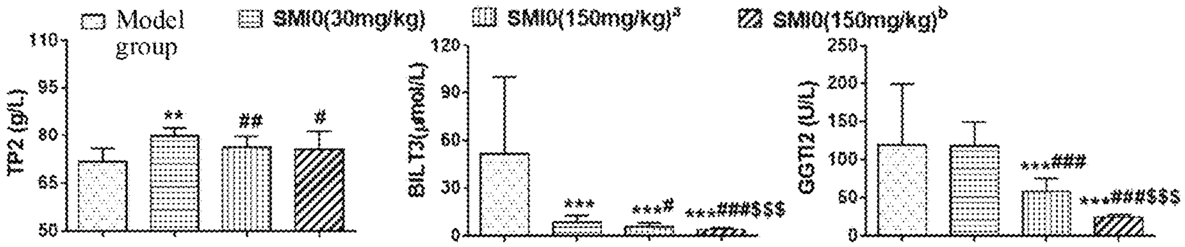
FIG. 13G
FIG. 13H
FIG. 13I

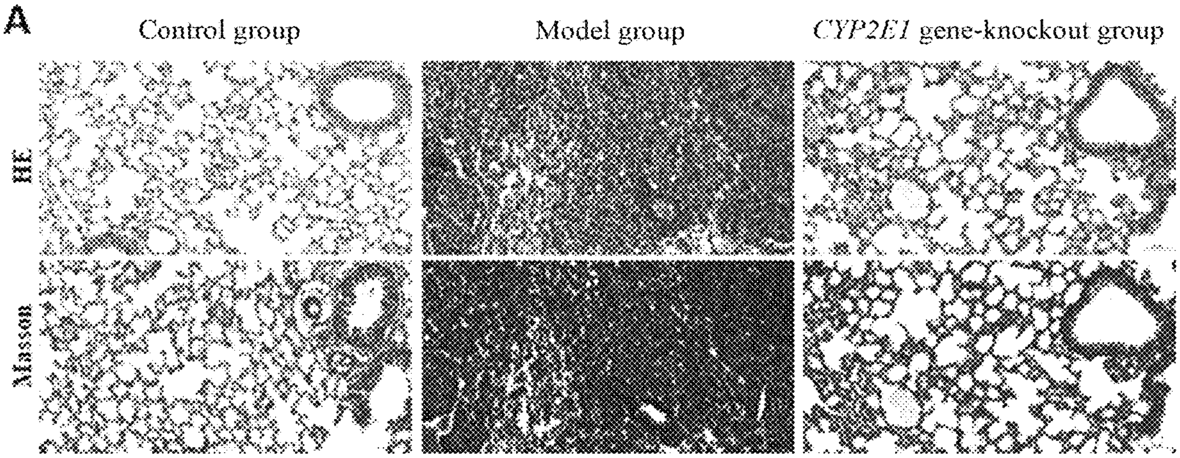
FIG. 20A
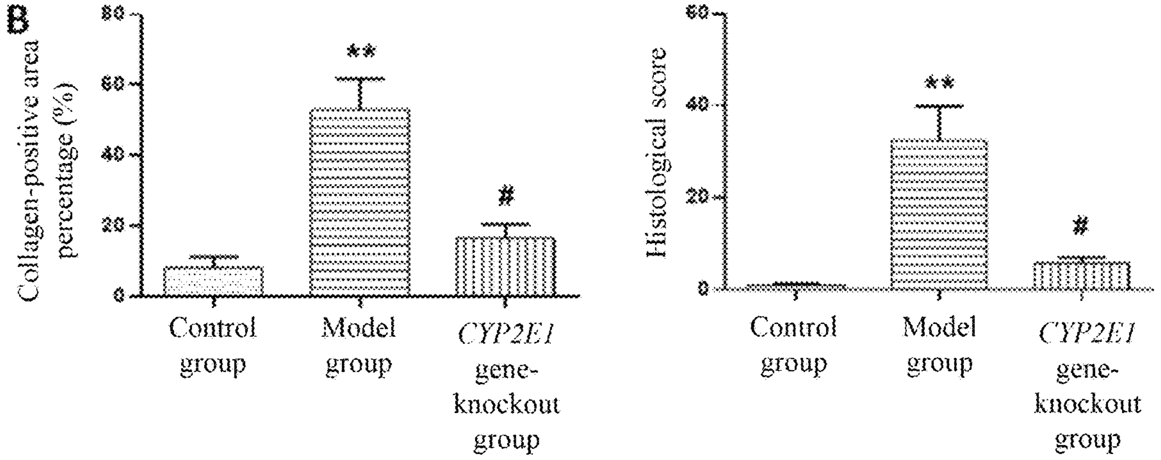
FIG. 20B
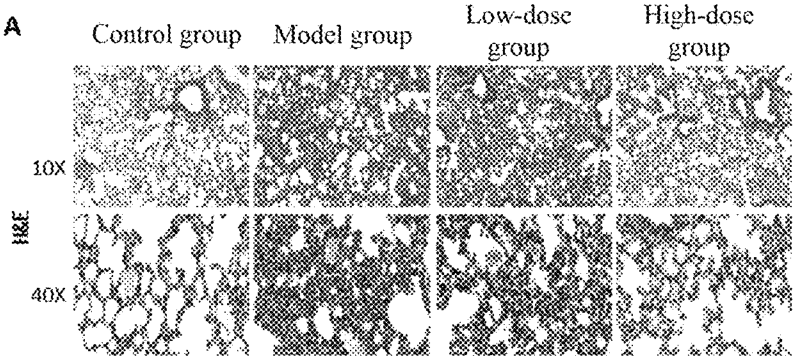
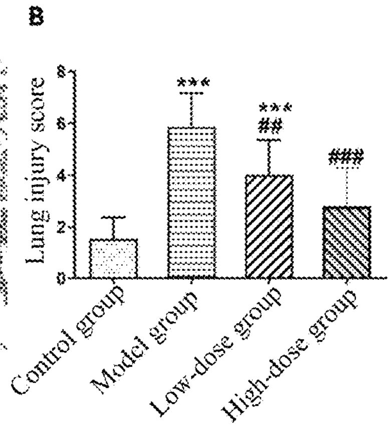
FIG. 21A
FIG. 21B

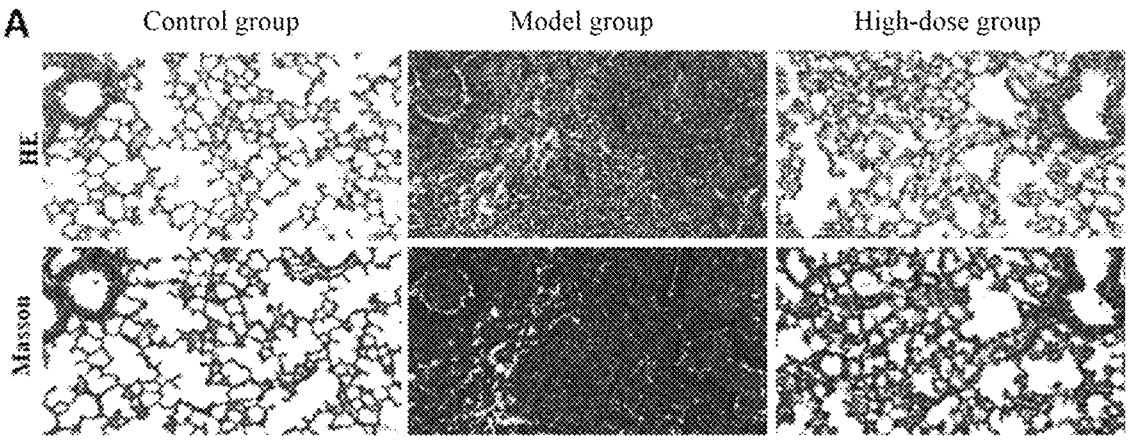
FIG. 22A
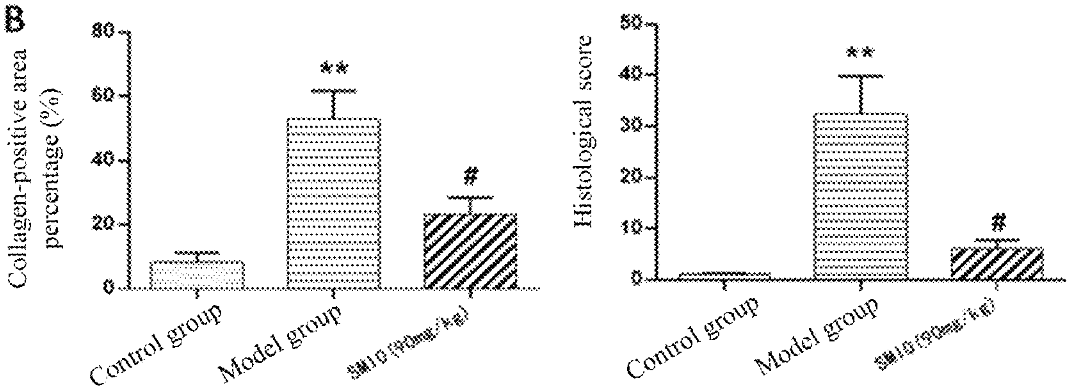
FIG. 22B
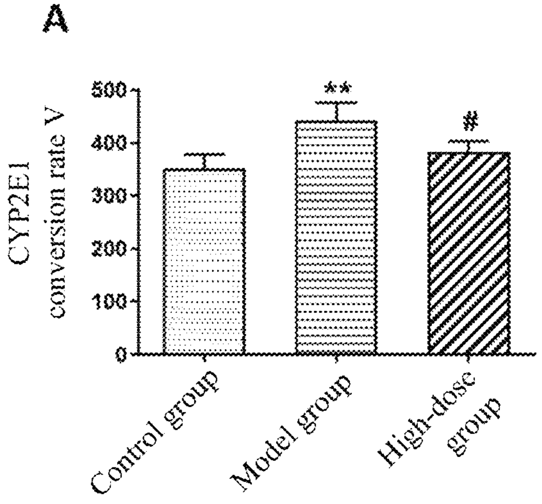
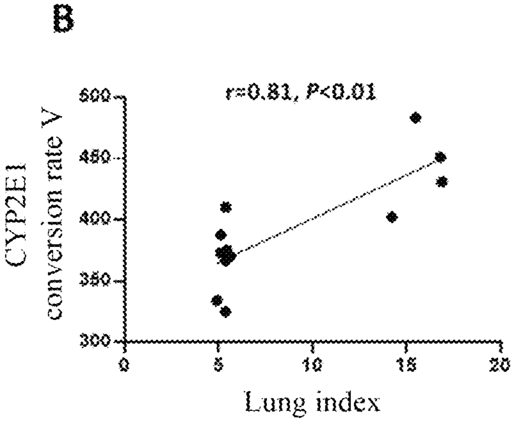
FIG. 23A
FIG. 23B

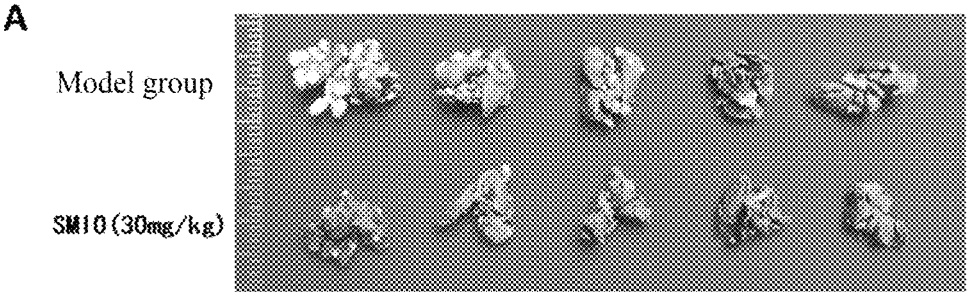
FIG. 31A
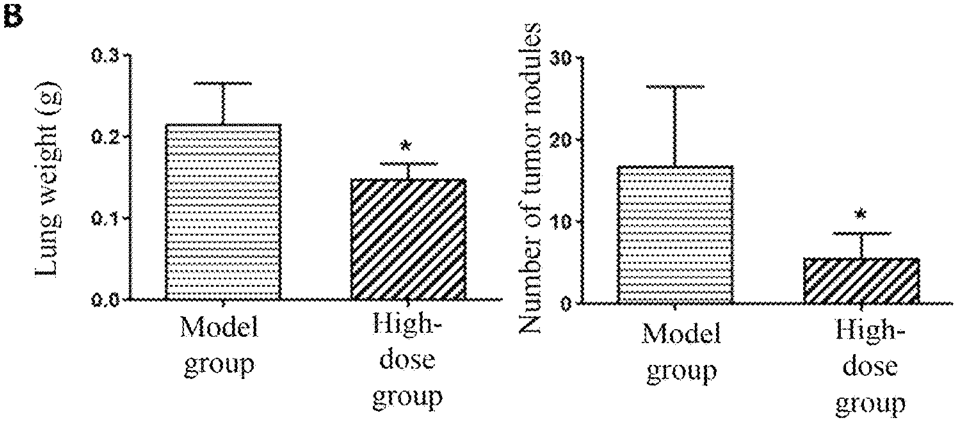
FIG. 31B
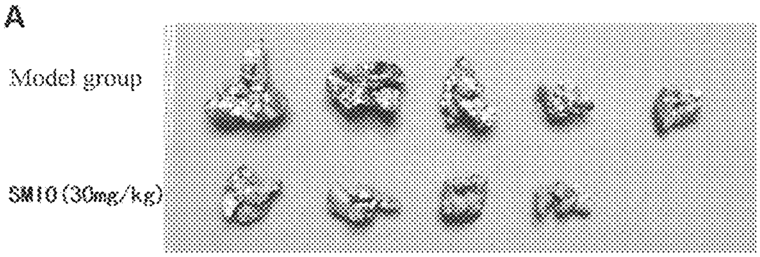
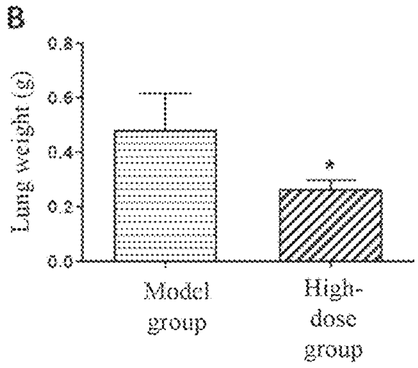
FIG. 32A
FIG. 32B

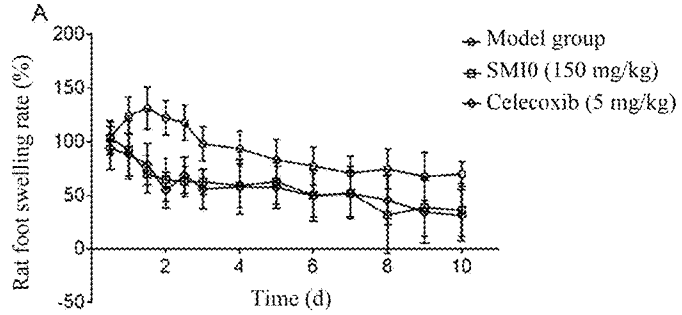
FIG. 60A
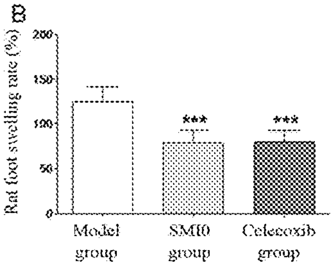
FIG. 60B
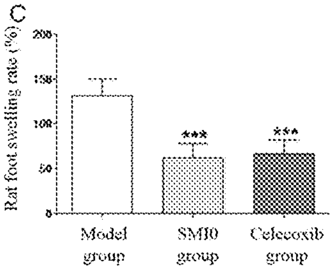
FIG. 60C
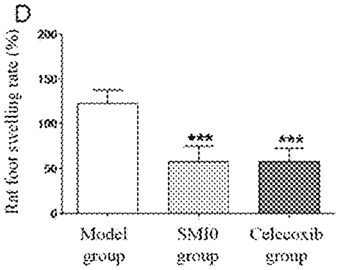
FIG. 60D
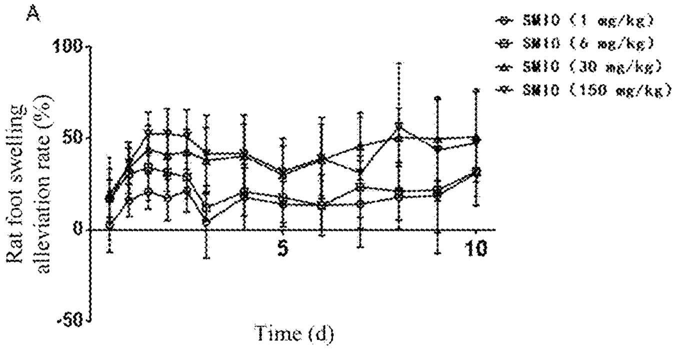
FIG. 61A
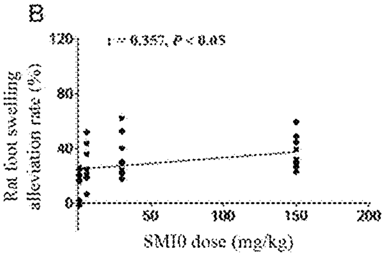
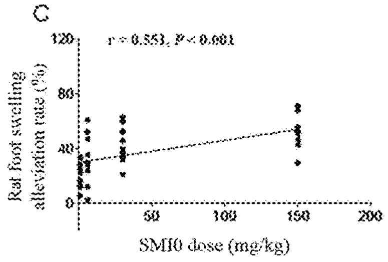
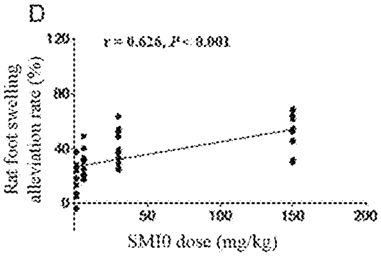
FIG. 61B FIG. 61C FIG. 61D

USE OF COMPOUND AS CYP2E1 INHIBITOR

CROSS REFERENCE TO THE RELATED APPLICATIONS

This application is the national phase entry of International Application No. PCT/CN2021/127710, filed on Oct. 29, 2021, which is based upon and claims priority to Chinese Patent Application No. 202010906508.3, filed on Sep. 1, 2020, the entire contents of which are incorporated herein by reference.

TECHNICAL FIELD

The present disclosure relates to the fields of targets and drugs for the prevention and treatment of inflammation-mediated diseases (IMDs) and specifically relates to a use of a compound as a CYP2E1 inhibitor.

BACKGROUND

It is currently recognized that the occurrence of many diseases is related to inflammation, such as tumors (liver cancer, cervical cancer, nasopharyngeal carcinoma (NPC), colorectal cancer (CRC), glioma, and lung cancer) and non-tumor diseases (Alzheimer's disease (AD), Parkinson's syndrome, stroke, arteriosclerosis, diabetes, liver fibrosis, and pulmonary fibrosis); and the above diseases related to inflammation can be collectively referred to as IMD. It is generally believed that a long-term non-controllable inflammatory microenvironment is associated with the occurrence of IMD. In 2005, on the 125th anniversary of Science's publication, it was written that "inflammation is a major cause for all chronic diseases."

A tumor microenvironment (TME) plays a critical role in the occurrence and development of a tumor, and in the past 10 years, the study of TME has developed rapidly. In 2010, Professor Karin M of the University of California wrote on Cell that the immunity and inflammation in a TME are closely related to the occurrence and development of a tumor. In recent years, breakthroughs have been made in the immunological research of TME, and the immunotherapeutic drugs PD-1 and PD-L1 targeting TME have been successfully used in clinical practice and have become broad-spectrum anti-tumor drugs. The American immunologist James P. Allison and the Japanese immunologist Tasuku Honjo, who had made outstanding original contributions to this field, were awarded the 2018 Nobel Prize in Physiology or Medicine.

Chronic non-controllable inflammation is an important feature of TME. For example, liver cancer usually originates from hepatitis and cirrhosis, hepatic stellate cells (HSCs) are an important constituent part of a general TME in addition to hepatoma extracellular stromal cells, and the activation of HSCs can lead to collagen deposition. Persistent liver damage caused by alcohol abuse, nonalcoholic steatohepatitis (NASH), chronic hepatitis B virus (CHBV) infection, or the like can lead to hypoxia and chronic uncontrolled inflammation, which are important features of a TME of liver cancer.

The occurrence and development of a tumor are closely related to a TME, and TME-targeted drugs have become effective means for treating liver cancer, such as immune checkpoint inhibitors (ICIs) PD-1 and PDL-1 and an angiogenesis inhibitor bevacizumab. The TME-targeted drugs generally have a broad-spectrum anti-tumor effect. For example, the angiogenesis inhibitor bevacizumab can be used to treat CRC, non-small cell lung cancer (NSCLC), renal cell carcinoma (RCC), ovarian cancer, cervical cancer, liver cancer, or the like; and the ICIs PD-1 and PDL-1 can be used to treat melanoma, lung cancer, breast cancer, liver cancer, pancreatic cancer, digestive tract tumor, gynecological tumor, urologic tumor, myeloma, lymphoma, or the like.

The successful development of drugs targeting immunity and angiogenesis in a TME provides a successful reference for tumor research. Admittedly, the traditional anti-inflammatory drugs such as COX-2 inhibitors and other non-steroidal anti-inflammatory drugs (NSAIDs) have played an important role as an antipyretic, analgesic, anti-inflammatory, and anti-rheumatic but have not exhibited satisfactory efficacy for inflammation-associated tumors, and there is currently no anti-tumor drug targeting an inflammatory TME. This may be because there are new targets of inflammation in a chronic uncontrolled inflammatory microenvironment that have not yet been discovered.

Cytochrome P450 2E1 (CYP2E1) is a protein mainly present in the endoplasmic reticulum (ER) of hepatocytes, and the applicants have found that the highest proportion of CYP2E1 in hepatic cytochrome P450 (CYP450) is about 24.8%. CYP2E1 mainly has a function of metabolism and participates in the biotransformation of drugs, procarcinogens, and environmental toxins. For example, CYP2E1 can metabolically activate more than 85 exogenous substances to produce hepatotoxic or carcinogenic substances, including nitrosamines, benzene, 1,3-butadiene, toluene, chloroform, acetone, tobacco-specific carcinogen NNK, or the like.

The metabolic activation of CYP2E1 is closely related to IMDs such as tumors. For example, the occurrence of liver cancer is related to various factors such as hepatitis virus, nitrosamine, aflatoxin, and alcohol. Nitrosamine (N-nitrosamine) is a strong carcinogen, which is metabolically activated by CYP2E1 in vivo to produce a carcinogen and then forms an adduct with DNA to cause liver cancer. The nitrosamine content in most traditional Chinese foods, such as cooked meat products, preserved meat, ham, and pickled vegetables exceeds a given standard; and epidemiological studies have proved that nitrosamine content in food is closely related to the occurrence of liver cancer. Animal experiments have shown that the knockout of a CYP2E1 gene in mice can significantly inhibit diethylnitrosamine (DEN)-induced liver cancer in mice. It suggests that CYP2E1 may affect the occurrence of liver cancer by affecting the metabolic activation of nitrosamine in vivo.

An inflammatory effect of CYP2E1 is closely related to IMIDs such as tumors. CYP2E1 has a significant inflammatory effect and is involved in the occurrence and development of many IMIDs. CYP2E1 is related to inflammation-associated tumors, such as liver cancer, glioma, ovarian cancer, lung cancer, NPC, bladder cancer, and gallbladder cancer, and the occurrence and development of hepatic diseases, such as liver damage, NASH, liver fibrosis, and other IMIDs such as rheumatoid arthritis, sepsis, AD, hyperlipidemia, diabetes, ischemic stroke, and pulmonary fibrosis. CYP2E1 can enhance the release of TNF-α in Kupffer cells, resulting in inflammatory necrosis of hepatocytes. In NASH model mice, the activity of CYP2E1 can be inhibited by reducing the expression of TNF-α, restoring the activity of endothelial nitric oxide synthase (eNOS), or the like. The knockout of the CYP2E1 gene in mice can significantly inhibit an inflammatory response induced by chronic alcohol exposure, and the CYP2E1 inhibitor diallyl sulfide can reduce the release of IL-1β and IL-12 by inhibiting CYP2E1 to prevent and treat NASH.

The inflammatory effect of CYP2E1 is related to the promotion of oxidative stress and lipid peroxidation (LPO). CYP2E1 can promote the generation of reactive oxygen species (ROS), induce oxidative stress and LPO, and cause hepatocellular inflammation, apoptosis, and liver fibrosis. The high expression of CYP2E1 in hepatocytes can promote the generation of ROS. ROS can activate a cell-surface molecule Fas ligand (FasL) of the tumor necrosis factor (TNF) family to produce a protease-linked reaction, thereby causing cell lysis and apoptosis. Apoptotic hepatocytes can promote the aggregation of inflammatory cells and induce the production of inflammatory factors, such as TNF-$\alpha$ and IL-6, thereby causing liver inflammation and steatohepatitis. CYP2E1 can also affect the metabolism of arachidonic acid (AA) and promote the invasion and metastasis of liver cancer cells. Studies have shown that CYP2E1 increases AA toxicity mainly through ROS and LPO products. CYP2E1 can cause the release of $Ca^{2+}$ in cells through ROS peroxidation to activate phospholipase A2 (PLA2), thereby promoting the generation of AA. In liver cancer cells, AA is converted into prostaglandin 2 (PGE2) under the action of cyclooxygenase 2 (COX-2), and PGE2 binds to an EP receptor coupled to G protein on a cell membrane to activate the EGFR/Met signaling pathway, thereby causing the invasion and metastasis of liver cancer cells.

In recent years, the applicants have established a large liver specimen bank including liver specimens of more than 127 healthy individuals and liver specimens of 102 liver cancer patients with liver cirrhosis to systematically investigate the physiology and pathology of CYP450. It has been found that an individual difference of CYP2E1 is about 10 times or more; the metabolic activity of CYP2E1 in a liver cancer patient is significantly increased by about 2.13 times, and a positive rate is about 44.6%; the activity of CYP2E1 is significantly negatively correlated with a postoperative survival period of a patient, and CYP2E1 positive and negative individuals have survival periods of 238 d and 612 d, respectively; and the increase in CYP2E1 activity is an independent risk factor for the occurrence and development of liver cancer. It has been proved by a rat primary hepatocellular carcinoma (PHC) model that the innate activity (before modeling) of CYP2E1 has a prominent causal relationship with the occurrence of liver cancer, that is, the higher the innate activity of CYP2E1, the more prone to liver cancer. It is suggested that CYP2E1 may be a new target for the prevention and treatment of liver cancer, and thus it is speculated that a drug targeting the new target CYP2E1 in an inflammatory TME may have a broad-spectrum prevention and treatment effect for IMDs.

In conclusion, CYP2E1 participates in the occurrence and development of many IMDs through metabolic activation and inflammation, and thus the inhibition of CYP2E1 activity is of great significance for the prevention and treatment of the IMDs. Therefore, the investigation of inhibitors for CYP2E1 has very important theoretical and practical significance.

There are currently no clinical CYP2E1-specific inhibitors. The compounds or drugs with a CYP2E1-inhibiting effect reported in the current study include 4-methylpyrazole, disulfiram, diethyldithiocarbamate (DDTC), isothiocyanic acid, orphenadrine, and chlormethiazole, and most of the compounds or drugs have poor selection specificity for the CYP2E1-inhibiting effect and great toxicity. Therefore, these compounds or drugs are mostly used in basic research. There are currently no clinical CYP2E1-specific inhibitors. Therefore, based on the role of CYP2E1 in the occurrence and development of many diseases such as hepatic diseases, there is an urgent need to conduct the screening and synthesis of CYP2E1 inhibitors.

SUMMARY

An aspect of the present disclosure discloses a use of a compound as a CYP2E1 inhibitor, including: using a compound shown in formula (I) or a salt thereof as an inhibitor to inhibit CYP2E1, where the compound or the salt thereof targets and binds to CYP2E1.

According to a first aspect of the present disclosure, a use of a compound as a CYP2E1 inhibitor is provided.

The use of a compound as a CYP2E1 inhibitor includes: using a compound shown in formula (I) or a salt thereof as an inhibitor to inhibit CYP2E1, where the compound or the salt thereof targets and binds to CYP2E1, formula (I)

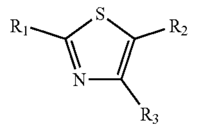

where $R_1$ is any one selected from the group consisting of hydrogen, $C_1$-$C_{10}$ alkyl, and epoxyalkyl;

$R_2$ is any one selected from the group consisting of hydrogen, substituted $C_1$-$C_{10}$ alkyl I, a substituent shown in formula 0-1, a substituent shown in formula 0-2, and a substituent shown in formula 0-3;

formula O-1

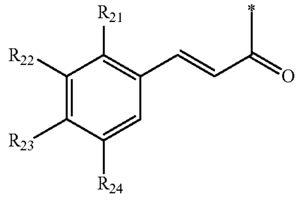

formula O-2

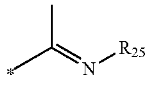

formula O-3

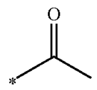

$R_{21}$, $R_{22}$, $R_{23}$, and $R_{24}$ each are independently at least one selected from the group consisting of hydrogen, alkoxy, halogen, $C_1$-$C_3$ alkyl, and $C_6$-$C_{10}$ aryl;

$R_{25}$ is any one selected from the group consisting of hydroxyl and alkoxy; and $R_3$ is at least one selected from the group consisting of hydrogen, $C_1$-$C_{10}$ alkyl, and substituted $C_1$-$C_{10}$ alkyl II.

Preferably, the epoxyalkyl is epoxybutyl.

Preferably, $R_1$ is any one selected from the group consisting of hydrogen, $C_1$-$C_4$ alkyl, and epoxyalkyl.

Preferably, $R_3$ is at least one selected from the group consisting of hydrogen, $C_1$-$C_4$ alkyl, and substituted $C_1$-$C_4$ alkyl II.

Optionally, the use refers to a use of the compound shown in formula I as a CYP2E1 inhibitor.

Optionally, a substituent in the substituted $C_1$-$C_{10}$ alkyl I is at least one selected from the group consisting of substituted amino I, a substituent shown in formula M-1, and a substituent shown in formula M-2:

formula M-1

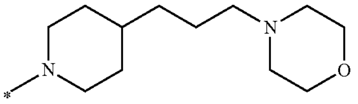

formula M-2

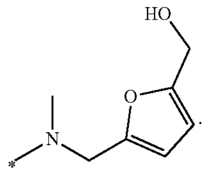

Optionally, a substituent in the substituted amino I is at least one selected from the group consisting of $C_6$-$C_{10}$ aryl and substituted $C_1$-$C_3$ alkyl III.

Preferably, a substituent in the substituted $C_1$-$C_3$ alkyl III is $C_6$-$C_{10}$ aryl.

Optionally, a substituent in the substituted $C_1$-$C_{10}$ alkyl II is at least one selected from the group consisting of substituted amino II, a substituent shown in formula M-3, and a substituent shown in formula M-4:

formula M-3

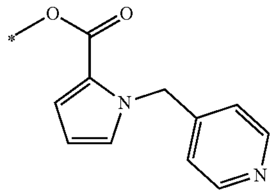

formula M-4

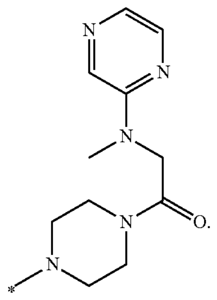

Optionally, a substituent in the substituted amino II is substituted $C_1$-$C_3$ alkyl IV; and a substituent in the substituted $C_1$-$C_3$ alkyl IV is at least one selected from the group consisting of pyridyl and halogen.

Optionally, the inhibitor is a compound shown in formula (I) or a pharmaceutically acceptable salt thereof:

formula (I)

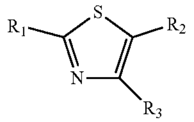

where $R_1$ is at least one selected from the group consisting of hydrogen, $C_1$-$C_{10}$ alkyl, and epoxyalkyl;

$R_2$ is at least one selected from the group consisting of hydrogen, substituted $C_1$-$C_{10}$ alkyl I, substituted carbonyl, and substituted imidyl; and $R_3$ is at least one selected from the group consisting of hydrogen, $C_1$-$C_{10}$ alkyl, and substituted $C_1$-$C_{10}$ alkyl II.

Optionally, a substituent in the substituted $C_1$-$C_{10}$ alkyl I is at least one selected from the group consisting of halogen, substituted amino I, a substituent shown in formula M-1, and a substituent shown in formula M-2:

formula M-1

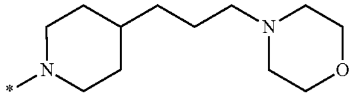

formula M-2

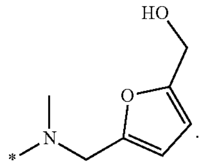

A substituent in the substituted carbonyl is substituted $C_1$-$C_{10}$ alkenyl; and a substituent in the substituted imidyl is at least one selected from the group consisting of hydroxyl and $C_1$-$C_3$ alkoxy.

Optionally, a substituent in the substituted amino I is at least one selected from the group consisting of $C_1$-$C_{10}$ aryl and substituted $C_1$-$C_3$ alkyl III.

Preferably, a substituent in the substituted $C_1$-$C_3$ alkyl III is $C_1$-$C_{10}$ aryl.

Optionally, a substituent in the substituted $C_1$-$C_{10}$ alkenyl is at least one selected from the group consisting of $C_1$-$C_{10}$ aryl and substituted $C_1$-$C_{10}$ aryl.

Preferably, a substituent in the substituted $C_1$-$C_{10}$ aryl is at least one selected from the group consisting of $C_1$-$C_3$ alkoxy, halogen, and $C_1$-$C_3$ alkyl.

Optionally, a substituent in the substituted $C_1$-$C_{10}$ alkyl II is at least one selected from the group consisting of substituted amino II, a substituent shown in formula M-3, and a substituent shown in formula M-4:

formula M-3

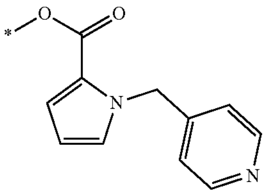

-continued formula M-4

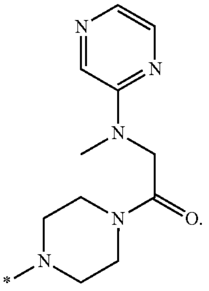

Optionally, a substituent in the substituted amino II is substituted $C_1$-$C_3$ alkyl IV; and a substituent in the substituted $C_1$-$C_3$ alkyl IV is at least one selected from the group consisting of pyridyl and halogen.

Optionally, the use includes: using at least one selected from the group consisting of the following compounds as an inhibitor to inhibit CYP2E1, where the at least one compound targets and binds to CYP2E1:

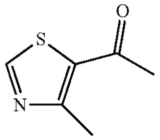
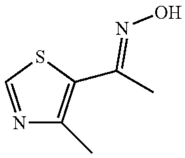
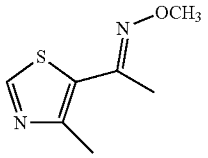

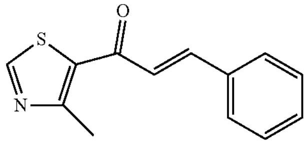

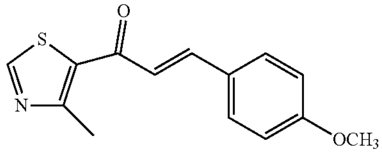

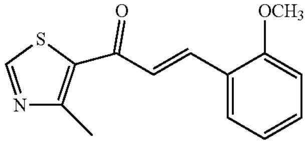

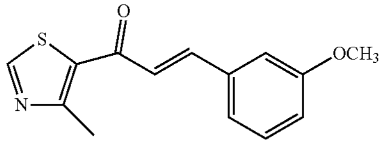

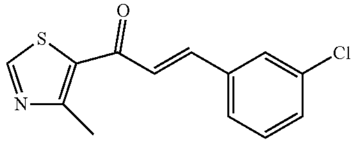

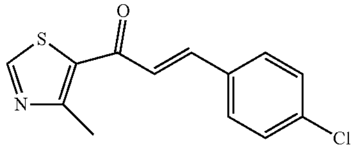

-continued

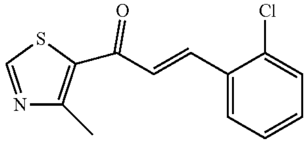

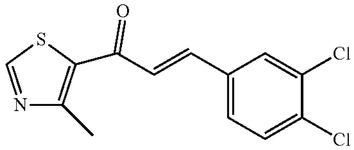

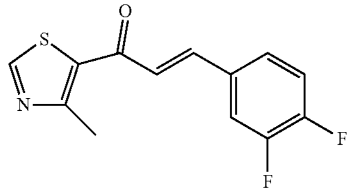

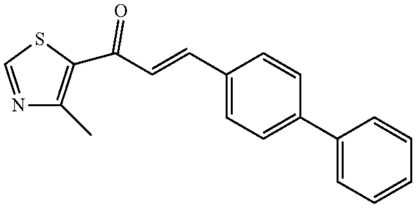

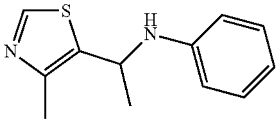

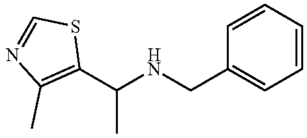

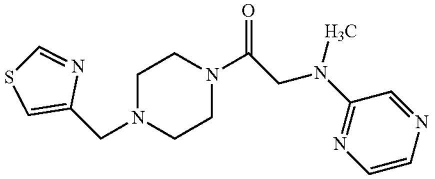

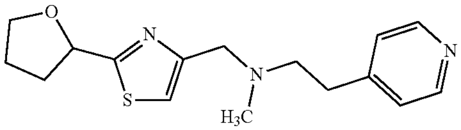

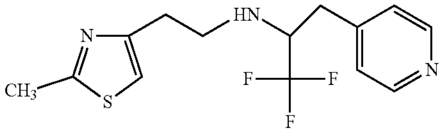

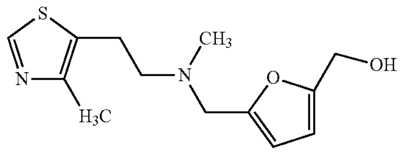

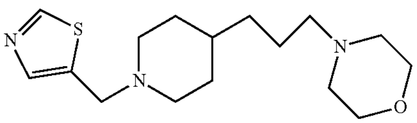

-continued

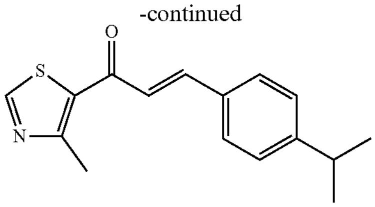

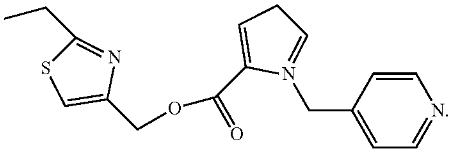

Optionally, the use includes: using at least one selected from the group consisting of the following compounds as an inhibitor to inhibit CYP2E1, where the at least one compound targets and binds to CYP2E1:

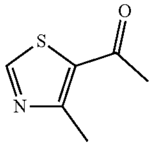

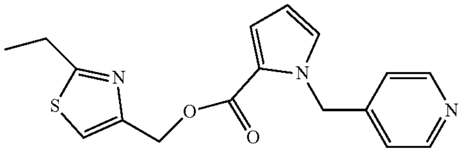

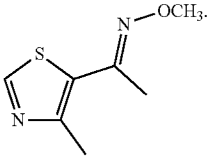

Preferably, the use includes: using at least one selected from the group consisting of the following compounds as an inhibitor to inhibit CYP2E1, where the at least one compound targets and binds to CYP2E1:

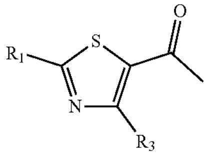

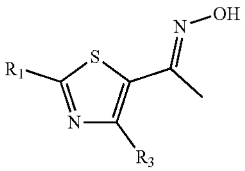

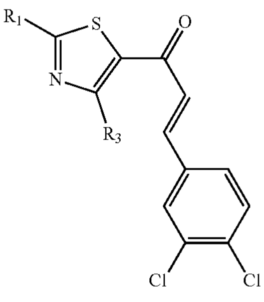

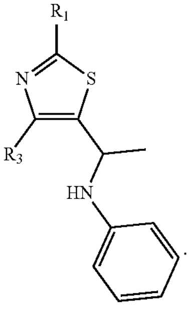

Optionally, the compound shown in formula (I) reacts with an acid to obtain an acid salt of the compound shown in formula (I); and the acid is at least one selected from the group consisting of an inorganic acid and an organic acid.

Optionally, the inorganic acid is at least one selected from the group consisting of hydrochloric acid, hydrobromic acid, hydroiodic acid, sulfuric acid, nitric acid, and phosphoric acid; and the organic acid is at least one selected from the group consisting of acetic acid, oxalic acid, succinic acid, tartaric acid, malic acid, lactic acid, methanesulfonic acid, p-toluenesulfonic acid, citric acid, resin acid, maleic acid, fumaric acid, salicylic acid, and acetylsalicylic acid.

Optionally, the compound shown in formula (I) has a structural formula of

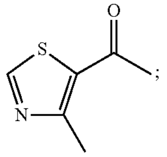

an X-ray powder diffraction (XRPD) pattern of a crystal form A of a hydrochloride of the compound shown in formula (I) includes 3 or more 2θ values selected from the group consisting of 8.4±0.2°, 13.1±0.2°, 14.8±0.2°, 16.6±0.2°, 24.1±0.2°, 27.2±0.2°, 30.5±0.2°, 31.8±0.2°, 33.5±0.2°, 35.4±0.2°, and 35.7±0.2°; and a differential scanning calorimetry-thermogravimetric analyzer (DSC-TGA) pattern of the crystal form A of the hydrochloride of the compound shown in formula (I) includes a significant endothermic peak at 70° C. to 220° C. and shows thermal decomposition at 80° C. to 170° C.

Optionally, the compound shown in formula (I) has a structural formula of

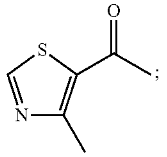

an XRPD pattern of a crystal form B of a sulfate of the compound shown in formula (I) includes 5 or more 2θ values selected from the group consisting of 10.1±0.2°, 15.1±±0.2°, 16.0±0.2°, 16.7±0.2°, 19.2±0.2°, 19.9±0.2°, 23.4±0.2°, 24.0±0.2°, 25.8±0.2°, 26.5 0.2°, 28.9±0.2°, 30.3±0.2°, and 32.2±0.2°; and a DSC-TGA pattern of the crystal form B of the sulfate of the compound shown in formula (I) includes at least one endothermic peak at 30° C. to 85° C., 90° C. to 160° C., or 215° C. to 330° C. and shows thermal decomposition at 150° C. to 350° C.

Optionally, a method for preparing the compound shown in formula (I) as an inhibitor at least includes any one selected from the group consisting of the following methods:

method 1: subjecting a raw material including a compound A, an aprotic solvent, and a Grignard reagent to a reaction at −20° C. to 25° C. for 0.5 h to 3 h to obtain a CYP2E1 inhibitor A, where the compound A is at least one selected from the group consisting of compounds with a structural formula shown in formula II:

formula II

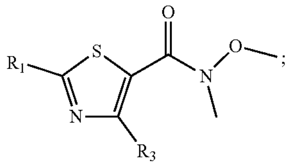

and the CYP2E1 inhibitor A is at least one selected from the group consisting of compounds with a structural formula shown in formula III:

formula III

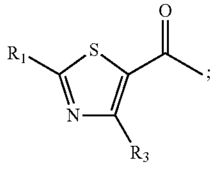

method 2: subjecting a compound with a structural formula shown in formula III and hydroxylamine hydrochloride to a reaction in the presence of an alkali source I to obtain a CYP2E1 inhibitor B, where the CYP2E1 inhibitor B is at least one selected from the group consisting of compounds with a structural formula shown in formula III-1:

formula III-1

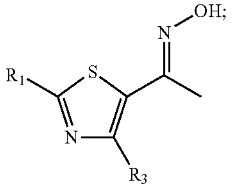

method 3: subjecting a compound with a structural formula shown in formula III and an aromatic aldehyde compound to a reaction at 25° C. to 100° C. for 2 h to 8 h in the presence of an alkali source II to obtain a CYP2E1 inhibitor C, where the CYP2E1 inhibitor C is at least one selected from the group consisting of compounds with a structural formula shown in formula III-2:

formula III-2

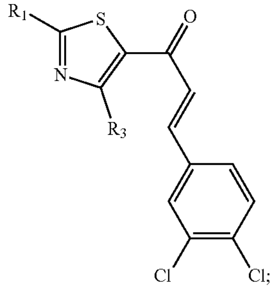

and method 4: subjecting a compound with a structural formula shown in formula III, an amine compound, and a reducing agent to a reaction in the presence of an acid source to obtain a CYP2E1 inhibitor D, where the amine compound is at least one selected from the group consisting of phenylamine and benzylamine; and the CYP2E1 inhibitor D is at least one selected from the group consisting of compounds with a structural formula shown in formula III-3:

formula III-3

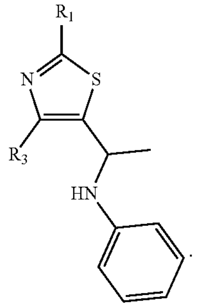

Optionally, the method 2 at least includes the following step: subjecting a compound with a structural formula shown in formula III, ethanol, and hydroxylamine hydrochloride to a reaction in the presence of an alkali source I to obtain a CYP2E1 inhibitor B.

Optionally, in the method 1, the aprotic solvent is at least one selected from the group consisting of tetrahydrofuran (THF) and diethyl ether and the Grignard reagent is at least one selected from the group consisting of methylmagnesium bromide and methylmagnesium chloride;

in the method 2, the alkali source I is at least one selected from the group consisting of potassium hydroxide, sodium hydroxide, sodium carbonate, pyridine, triethylamine (TEA), and N,N-diisopropylethylamine (DIPEA);

in the method 3, the alkali source II is at least one selected from the group consisting of sodium hydroxide, potassium hydroxide, potassium tert-butoxide, sodium methoxide, and potassium fluoride; and the aromatic aldehyde compound is at least one selected from the group consisting of p-methoxybenzaldehyde, o-methoxybenzaldehyde, m-methoxybenzaldehyde, p-chlorobenzaldehyde, o-chlorobenzaldehyde, m-chlorobenzaldehyde, p-phenylbenzaldehyde, p-isopropylbenzaldehyde, and 3,4-difluorobenzaldehyde; and in the method 4, the acid source is at least one selected from the group consisting of formic acid, acetic acid, and hydrochloric acid; and the reducing agent is at least one selected from the group consisting of sodium cyanoborohydride, sodium borohydride, and lithium aluminum hydride (LAH).

Optionally, in the method 1, a molar ratio of the compound A to the Grignard reagent is 1:1 to 1:3;

in the method 2, a molar ratio of the compound with the structural formula shown in formula III to the hydroxylamine hydrochloride is 1:1 to 1:6;

in the method 3, a molar ratio of the compound with the structural formula shown in formula III to the aromatic aldehyde compound is 1:1 to 1:5; and in the method 4, a molar ratio of the compound with the structural formula shown in formula III to the reducing agent is 1:1 to 1:5.

Optionally, the compound A is prepared through the following process:

subjecting a raw material including a compound A-1, a condensing agent, N,O-dimethylhydroxylamine hydrochloride, and an aprotic solvent to a reaction at 20° C. to 60° C. for 10 h to 20 h in a presence of an alkali source III to obtain the compound A, where the compound A-1 is at least one selected from the group consisting of compounds with a structural formula shown in formula II-1:

formula II-1

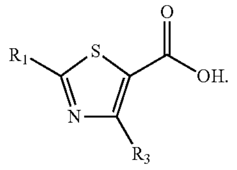

Optionally, the condensing agent is at least one selected from the group consisting of 1-ethyl-(3-dimethylaminopropyl) carbodiimide hydrochloride, didodecyl carbonate, N,N-carbonyldiimidazole, dicyclohexylcarbodiimide, and N-(4-carboxyphenyl) maleimide (CPMI); and the alkali source III is at least one selected from the group consisting of sodium hydroxide, potassium hydroxide, calcium hydroxide, sodium carbonate, potassium carbonate, pyridine, TEA, and DIPEA.

Optionally, the compound A-1, the condensing agent, and the N,O-dimethylhydroxylamine hydrochloride are in a molar ratio of 1:1:1 to 1:5:5.

Optionally, the preparation of the compound A-1 at least includes the following steps: subjecting a raw material including a compound A-2 to hydrolysis in the presence of an alkali source IV to obtain a mixture, and adjusting a pH of the mixture with an acid source to 2 to 3 to obtain the compound A-1, where the compound A-2 is at least one selected from the group consisting of compounds with a structural formula shown in formula II-2:

formula II-2

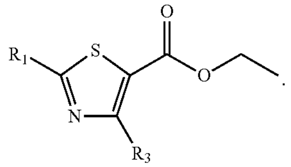

Optionally, the alkali source IV is at least one selected from the group consisting of sodium hydroxide, potassium hydroxide, calcium hydroxide, sodium carbonate, and potassium carbonate.

Optionally, the acid source is concentrated hydrochloric acid; and the adjusting a pH of the mixture with an acid source to 2 to 3 is conducted at 10° C. to 50° C.

Optionally, a preparation method of an acid salt of the compound shown in formula (I) at least includes:

subjecting a material including the compound shown in formula (I) and a solvent A to a reaction at −20° C. to 80° C. for 0.5 h to 10 h to obtain the acid salt of the compound shown in formula (I).

Preferably, the preparation method of the acid salt of the compound shown in formula (I) at least includes:

subjecting the material including the compound shown in formula (I) and the solvent A to a reaction at − 15° C. to 60° C. for 1 h to 4 h to obtain the acid salt of the compound shown in formula (I).

Further preferably, the preparation method of the acid salt of the compound shown in formula (I) at least includes:

subjecting the material including the compound shown in formula (I) and the solvent A to a reaction at −10° C. to 40° C. for 1 h to 4 h to obtain the acid salt of the compound shown in formula (I).

The present disclosure also provides an acid salt of a CYP2E1 inhibitor SMI0, and the acid salt is prepared through a reaction of SMI0 with an organic acid or an inorganic acid.

Optionally, the organic acid is one selected from the group consisting of acetic acid, oxalic acid, succinic acid, tartaric acid, malic acid, lactic acid, methanesulfonic acid, p-toluenesulfonic acid, citric acid, resin acid, maleic acid, fumaric acid, salicylic acid, and acetylsalicylic acid.

Optionally, the inorganic acid is one selected from the group consisting of hydrochloric acid, hydrobromic acid, hydroiodic acid, sulfuric acid, nitric acid, and phosphoric acid.

The present disclosure also provides a preparation method of the acid salt of the CYP2E1 inhibitor SMI0, including the following steps: preparing a solution system of SMI0 in a soluble solvent and a solution system of an acid in a soluble solvent, where a molar ratio of the SMI0 to the acid is 1:(0.5-3); mixing the two solution systems, and conducting a reaction at − 20° C. to 80° C. for 0.5 h to 10 h to produce a target product; and spin-drying under reduced pressure to remove the solvent to obtain the acid salt of the SMI0.

Optionally, an organic solvent used in the reaction includes one or a mixture of two or more selected from the group consisting of an ether, an alcohol, an ester, a nitrile, a ketone, a haloalkane, an alkane, and an aromatic solvent. Preferably, the soluble solvent is selected from the group consisting of methanol, acetonitrile, acetone, ethyl acetate, ethanol, and diethyl ether.

Optionally, the molar ratio of the SMI0 to the acid in the reaction is 1:(0.5-3) and preferably 1(1-2).

Optionally, a reaction temperature of the reaction changes with the reagent or solvent, but the reaction temperature is usually −20° C. to 80° C., preferably −15° C. to 60° C., and more preferably −10° C. to 40° C.; and a reaction time of the reaction also changes with the reagent or temperature, but the reaction time is usually 0.5 h to 10 h and preferably 1 h to 4 h.

The present disclosure also provides a crystal form A of a hydrochloride of the CYP2E1 inhibitor SMI0; an XRPD pattern of the crystal form A includes 3 or more 2θ values selected from the group consisting of 8.4±0.2°, 13.1±0.2°, 14.8±0.2°, 16.6±0.2°, 24.1±0.2°, 27.2±0.2°, 30.5±0.2°, 31.8±0.2°, 33.5±0.2°, 35.4±0.2°, and 35.7±0.2°; and a DSC-TGA pattern of the crystal form A includes a significant endothermic peak at 70° C. to 220° C. and shows thermal decomposition at 80° C. to 170° C.

The present disclosure also provides a crystal form B of a sulfate of the CYP2E1 inhibitor SMI0; an XRPD pattern of the crystal form B includes 5 or more 2θ values selected from the group consisting of 10.1±0.2°, 15.1±0.2°, 16.0±0.2°, 16.7±0.2°, 19.2±0.2°, 19.9±0.2°, 23.4±0.2°, 24.0±0.2°, 25.8±0.2°, 26.5±0.2°, 28.9±0.2°, 30.3±0.2°, and 32.2±0.2°; and a DSC-TGA pattern of the crystal form B includes at least one endothermic peak at 30° C. to 85° C., 90° C. to 160° C., or 215° C. to 330° C. and shows thermal decomposition at 150° C. to 350° C.

Optionally, the CYP2E1 inhibitor is used as an active substance in a drug for treating liver damage, fatty liver, hepatitis, and liver fibrosis.

Optionally, the CYP2E1 inhibitor is used in a kit for preventing and treating a hepatic disease.

Optionally, the CYP2E1 inhibitor is used in an active ingredient of a drug for treating or preventing an inflammation-associated tumor; and the inflammation-associated tumor includes at least one selected from the group consisting of liver cancer, glioma, ovarian cancer, lung cancer, bladder cancer, and gallbladder cancer.

Optionally, the CYP2E1 inhibitor is used in an active ingredient of a drug for treating or preventing an IMD; and the IMD includes at least one selected from the group consisting of liver damage, fatty liver, hepatitis, liver fibrosis, pulmonary fibrosis, rheumatic and rheumatoid arthritis, sepsis, AD, ischemic stroke, Parkinson's disease (PD), hyperlipidemia, atherosclerosis (AS), coronary heart disease (CHD), and diabetes.

The preferred CYP2E1 inhibitors in the present disclosure are shown in the table below:

| No. | Compound structure |
|---|---|
| SMI0 | 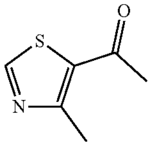 |

-continued

| No. | Compound structure |
|---|---|
| SMI1 | 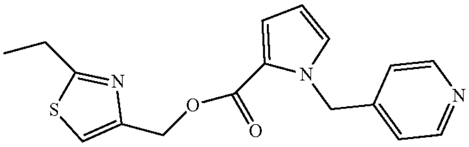 [SMILES: CCc1nc(COC(=O)c2cccn2Cc2ccncc2)cs1] |
| SMI7 | 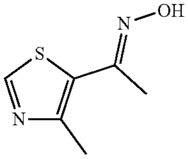 |

Optionally, the CYP2E1 inhibitors

SMI0

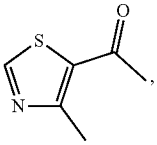,

SMI7

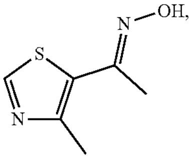,

SMI16

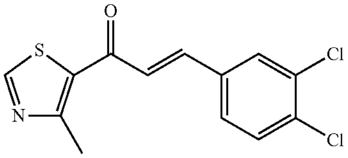

and

SMI20

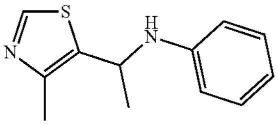

in the present disclosure are synthesized through the following synthesis route:

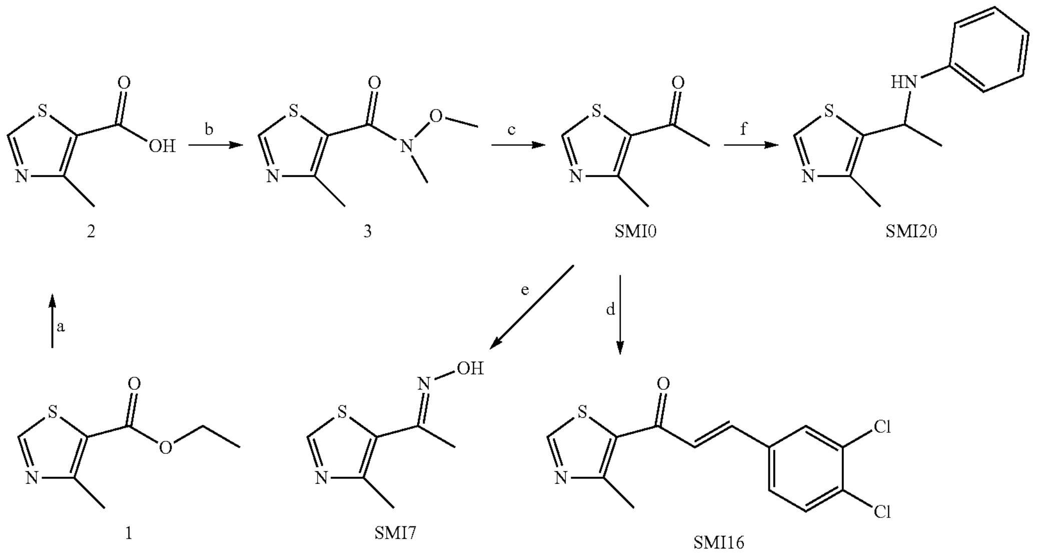

2 3 SMI0 SMI20 1 SMI7 SMI16 where reaction conditions are as follows: a. hydrolysis is conducted under alkaline conditions, and acidification is conducted;

b. the reaction with N,O-dimethylhydroxylamine hydrochloride is conducted in the presence of an alkali and a condensing agent;

c. the reaction with the Grignard reagent is conducted in an anhydrous aprotic solvent at a low temperature;

d. the aldol condensation reaction with the aromatic aldehyde is conducted under heating and alkaline conditions;

e. the reaction with ammonia is conducted under alkaline conditions; and f. the reaction with the amine is conducted in the presence of a weak acid and a reducing agent.

Optionally, in condition a, an alkali used may be one selected from the group consisting of sodium hydroxide, potassium hydroxide, calcium hydroxide, sodium carbonate, and potassium carbonate; an acid used may be one or a mixture of two or more selected from the group consisting of hydrochloric acid, sulfuric acid, nitric acid, phosphoric acid, and acetic acid; a solvent used is a mixture of one selected from the group consisting of water-soluble solvents such as methanol, ethanol, and propanol with water; and the reaction is conducted at 10° C. to 50° C.

Optionally, in condition b, the alkali may be one selected from the group consisting of sodium hydroxide, potassium hydroxide, calcium hydroxide, sodium carbonate, potassium carbonate, pyridine, TEA, and DIPEA; the condensing agent may be one selected from the group consisting of 1-ethyl-(3-dimethylaminopropyl)carbodiimide hydrochloride, didodecyl carbonate, N,N-carbonyldiimidazole, and CPMI; the reaction is conducted at 20° C. to 60° C.; and a solvent used is one selected from the group consisting of aprotic solvents such as THF and diethyl ether.

Optionally, in condition c, the reaction is conducted at −20° C. to 25° C.; a solvent used is one selected from the group consisting of aprotic solvents such as THF and diethyl ether; and an equivalent ratio of the compound 3 to the Grignard reagent is 1:1 to 1:3.

Optionally, in condition d, an alkali used may be one selected from the group consisting of sodium hydroxide, potassium hydroxide, potassium tert-butoxide, sodium methoxide, and potassium fluoride; the reaction is conducted at 25° C. to 100° C.; and a solvent used is one selected from the group consisting of water-soluble solvents such as methanol, ethanol, and propanol.

Optionally, in condition e, an alkali used may be one selected from the group consisting of potassium hydroxide, sodium hydroxide, sodium carbonate, pyridine, TEA, and DIPEA; and a solvent used is a mixture of one selected from the group consisting of water-soluble solvents such as methanol and ethanol with water.

Optionally, in condition f, an acid used may be one or a mixture of two or more selected from the group consisting of organic or inorganic acids such as formic acid, acetic acid, and hydrochloric acid; and a solvent used is one selected from the group consisting of water-soluble solvents such as methanol, ethanol, and propanol.

In the present disclosure, $C_1$-$C_{10}$ refers to a number of carbon atoms in a group. A number of carbon atoms in "substituted alkyl" or "substituted aryl" refers to a number of carbon atoms in alkyl or aryl itself, and does not refer to a number of carbon atoms after substitution. For example, $C_1$-$C_{10}$ substituted alkyl refers to alkyl with 1 to 10 carbon atoms in which at least one hydrogen atom is substituted by a substituent.

In the present disclosure, the "alkyl" is a group obtained by removing any hydrogen atom on an alkane molecule. The alkane includes a linear alkane, a branched alkane, a cycloalkane, and a branched chain-containing cycloalkane.

In the present disclosure, the "alkenyl" is a group obtained by removing any hydrogen atom on an alkene molecule. The alkene includes a linear alkene, a branched alkene, a cycloalkene, and a branched chain-containing cycloalkene.

In the present disclosure, the "aryl" is a group obtained by removing a hydrogen atom on an aromatic ring of an aromatic molecule, such as p-methylphenyl obtained by removing a hydrogen atom at a para position of methyl on a benzene ring of toluene.

In the present disclosure, the "furyl" is a group obtained by removing any hydrogen atom on a furan molecule.

In the present disclosure, the "imidyl" is a divalent group left after two hydrogen atoms are removed from an ammonia molecule, and has a structural formula of .

In the present disclosure, the "pyridyl" is a group obtained by removing any hydrogen atom on a pyridine molecule.

In the present disclosure, the "epoxyalkyl" is a group obtained by removing any hydrogen atom on an epoxy molecule.

BRIEF DESCRIPTION OF THE DRAWINGS

FIGS. 13A-13I show inhibitory effects of the compound SMI0 on DEN-induced rat liver damage models;

FIG. 14A shows representative pictures of mouse livers in each hepatitis model group; FIG. 14B shows inflammation-associated histopathological manifestations; H&E refers to hematoxylin and eosin staining; Masson refers to Masson staining; Oil red refers to oil red O staining; and LCA refers to leukocyte common antigen staining;

FIG. 15A shows a liver coefficient of animals in each hepatitis model group; FIG. 15B shows a steatosis score of animals in each group; FIG. 15C shows a Masson staining score of animals in each group; FIG. 15D shows a percentage of an oil red O staining area of animals in each group; and FIG. 15E shows an LCA staining score of animals in each group;

FIG. 16A shows representative pictures of mouse livers in each liver fibrosis model group; FIG. 16B shows inflammation and liver fibrosis-associated histopathological manifestations; H&E refers to hematoxylin and eosin staining; Masson refers to Masson staining; and Oil red refers to oil red O staining;

FIG. 17A shows a liver coefficient of animals in each liver fibrosis model group; FIG. 17B shows a steatosis score of animals in each group; FIG. 17C shows a Masson staining score of animals in each group; and FIG. 17D shows a percentage of an oil red O staining area of animals in each group;

FIG. 18A shows representative pictures of rat livers in each liver fibrosis model group; FIG. 18B shows liver fibrosis-associated histopathological manifestations; H&E refers to hematoxylin and eosin staining; Masson refers to Masson staining; α-SMA refers to α-smooth muscle actin; and collagen I refers to type I collagen;

FIG. 19A shows a liver coefficient of animals in each liver fibrosis model group; FIG. 19B shows a Ishark score of animals in each group; FIG. 19C shows a Masson staining score of animals in each group; FIG. 19D shows a α-SMA histochemical score of animals in each group; and FIG. 19E shows a collagen I histochemical score of animals in each group;

FIGS. 20A-20B show inhibitory effects of CYP2E1 gene knockout on lipopolysaccharide (LPS)-induced mouse pulmonary fibrosis models, where FIG. 20A shows HE and Masson staining results of a mouse lung tissue in each group; and FIG. 20B shows a collagen-positive area percentage and a histological score of a mouse lung tissue in each group;

FIGS. 21A-21B show inhibitory effects of the compound SMI0 on LPS-induced mouse lung injury, where FIG. 21A shows HE staining results of a mouse lung tissue in each group; and FIG. 21B shows a lung injury score of mice in each group;

FIGS. 22A-22B show inhibitory effects of the compound SMI0 on LPS-induced mouse pulmonary fibrosis models, where FIG. 22A shows HE and Masson staining results of a mouse lung tissue in each group; and FIG. 22B shows a collagen-positive area percentage and a histological score of a mouse lung tissue in each group;

FIGS. 23A-23B show a change of CYP2E1 activity and a correlation of CYP2E1 activity with a pulmonary fibrosis severity in LPS-induced mouse pulmonary fibrosis models, where FIG. 23A shows a change of CYP2E1 activity of mice in each group; and FIG. 23B shows a correlation between CYP2E1 activity and a lung index in mice;

FIG. 24A shows MPO staining results of a mouse lung tissue in each group; and FIG. 24B shows an MPO-positive staining area percentage in a mouse lung tissue in each group;

FIG. 25A shows a relative expression level of TNF-α in a mouse lung tissue in each group; and FIG. 25B shows a relative expression level of IL-1β in a mouse lung tissue in each group;

FIG. 26A shows an oxidative stress index CAT level in a mouse lung tissue in each group; FIG. 26B and FIG. 26C show Western Blot (WB) results of the expression of epithelial cell marker E-cadherin and apoptosis-associated proteins in a mouse lung tissue in each group; and FIG. 26D, FIG. 26E, and FIG. 26F show quantification results of the expression of epithelial cell marker E-cadherin and apoptosis-associated proteins in a mouse lung tissue in each group;

FIG. 27A and FIG. 27C show TGF-β1 and α-SMA staining results of a mouse lung tissue in each group; and FIG. 27B and FIG. 27D show TGF-β1 and α-SMA-positive staining area percentages in each group;

FIG. 29A is a general picture illustrating a lung tumor in each mouse; and FIG. 29B shows a weight of a lung tumor in each mouse;

FIG. 30A shows a representative picture of a tumor-bearing lung tissue of mice in each group; FIG. 30B is a general picture illustrating a lung tumor in each mouse; and FIG. 30C shows a weight of a lung tumor in each mouse;

FIGS. 31A-31B show inhibitory effects of the compound SMI0 on lung metastasis models constructed through tail vein injection of CRC cells CT26, where FIG. 31A is a general picture illustrating a tumor-bearing lung tissue of each mouse; and FIG. 31B shows a weight of a lung of each mouse;

FIGS. 32A-32B show inhibitory effects of the compound SMI0 on lung metastasis models constructed through tail vein injection of melanoma cells B16-F10, where FIG. 32A is a general picture illustrating a tumor-bearing lung tissue of each mouse; and FIG. 32B shows a weight of a lung of each mouse;

FIG. 34A shows WB results of the expression of inflammatory factors and related signaling pathway proteins in a paracancerous lung tissue of mice in each group; and FIG. 34B shows quantification results of the expression of inflammatory factors and related signaling pathway proteins in a paracancerous lung tissue of mice in each group;

FIG. 35A shows WB results of apoptosis and expression of autophagy-associated proteins in lung cancer tissues of mice in each group; and FIG. 35B shows quantification results of apoptosis and expression of autophagy-associated proteins in lung cancer tissues of mice in each group;

FIG. 36A is for Lewis lung cancer cells; and FIG. 36B is for A549 lung cancer cells;

FIG. 39A is a representative picture illustrating tumor-bearing livers of rats in each group; FIG. 39B shows liver tumors of rats in each group; and FIG. 39C shows a total tumor weight and a maximum tumor diameter in the liver of each rat;

FIG. 40A is a representative picture illustrating tumor-bearing livers of mice in each group; FIG. 40B shows liver tumors of mice in each group; and FIG. 40C shows a total tumor weight and a maximum tumor diameter in the liver of each mouse;

FIG. 41A shows WB results of the expression of inflammatory factors and related signaling pathway proteins in a paracancerous liver tissue of mice in each group; and FIG. 41B shows quantification results of the expression of inflammatory factors and related signaling pathway proteins in a paracancerous liver tissue of mice in each group;

FIG. 42A shows WB results of apoptosis and expression of related signaling pathway proteins in liver cancer tissues of mice in each group; and FIG. 42B shows quantification results of apoptosis and expression of related signaling pathway proteins in liver cancer tissues of mice in each group;

FIG. 43A is for HepG2 liver cancer cells; and FIG. 43B is for H22 liver cancer cells;

FIGS. 44A-44C show the influence of SMI0 on apoptosis, migration, and proliferation of HepG2 liver cancer cells co-cultivated with macrophages; and FIGS. 44D-44E show quantification results of the influence of SMI0 on apoptosis and migration of HepG2 liver cancer cells co-cultivated with macrophages;

FIG. 45A shows immunohistochemical results; and FIG. 45B shows qPCR results;

FIG. 47A is a general picture illustrating brains of mice in each group; FIG. 47B shows representative pictures of HE staining of mouse brain tissues in each group; FIG. 47C shows a tumor volume of mice in each group; and FIG. 47D shows an in vitro inhibitory effect of SMI0 on GL261 cells;

FIG. 50A and FIG. 50C show the inhibition on proliferation of tumor cells; and FIG. 50B and FIG. 50D show the promotion on apoptosis of tumor cells;

FIG. 51A shows the inhibition on proliferation of tumor cells; and FIG. 51B shows the promotion on apoptosis of tumor cells;

FIG. 54A shows a total tumor weight of mice in each group; FIG. 54B shows an ascites weight of mice in each group; and FIG. 54C shows an in vitro inhibitory effect of SMI0 on ID-8 cells;

FIG. 55A shows a total tumor weight of mice in each group; and FIG. 55B shows an ascites weight of mice in each group;

FIG. 56A shows general representative pictures of feet in each group; and FIG. 56B shows the hindfoot score, hindfoot thickness, and hindfoot volume of rats in each group;

FIG. 57A shows the foot swelling coefficient of rats in each group; and FIG. 57B shows the total score, foot thickness, and foot volume of rats in each group;

FIG. 58A shows a foot swelling recovery rate of rats in SMI0 groups of different doses; and FIG. 58B shows a correlation between a SMI0 dose and a rat foot swelling recovery rate on day 2, day 8, and day 20;

FIGS. 60A-60B show quantification results of relevant parameters of the inhibition of the compound SMI0 on CFA-induced rat rheumatoid arthritis models, where FIG. 60A shows foot swelling rates of rats in each group at different time points; FIG. 60B shows a rat foot swelling rate at 24 h; FIG. 60C shows a rat foot swelling rate at 36 h; and FIG. 60D shows a rat foot swelling rate at 48 h;

FIGS. 61A-61D show a dose-response relationship of the inhibition of the compound SMI0 on CFA-induced rat rheumatoid arthritis models, where FIG. 61A shows dose-response relationships for a rat foot swelling rate at different time points; FIG. 61B shows a dose-response relationship at 24 h; FIG. 61C shows a dose-response relationship at 36 h; and FIG. 61D shows a dose-response relationship at 48 h;

FIG. 62A shows a change of CYP2E1 activity in rheumatoid arthritis rat models; and FIG. 62B shows a correlation between CYP2E1 activity and foot swelling severity in rats;

FIG. 63A shows body temperatures of rats in each group at different time points; FIG. 63B shows a body temperature of rats in each group at 4 h.

FIG. 64A shows body temperatures of mice in each group at different time points; FIG. 64B shows a body temperature of mice in each group at 6 h;

FIG. 64C shows a body temperature of mice in each group at 12 h; and FIG. 64D shows a body temperature of mice in each group at 24 h;

FIG. 65A shows a serum urea nitrogen level of mice in each group at 24 h; FIG. 65B shows a serum creatinine level of mice in each group at 24 h; FIG. 65C shows a creatine kinase (CK) level of mice in each group at 24 h; and FIG. 65D shows a serum lactate dehydrogenase (LDH) level of mice in each group at 24 h;

FIG. 66A shows incubation periods of rats in each group at different training time points; FIG. 66B shows a time spent in the platform quadrant of rats in each group; and FIG. 66C shows a number of platform crossings of rats in each group;

FIG. 68A shows a cerebral infarction rate in rats; and FIG. 68B shows a cerebral edema rate in rats;

FIG. 70A shows a total plaque area of animals in each group; and FIG. 70B shows a percentage of an oil red O area in a total plaque area of animals in each group;

FIG. 71A shows a fasting blood glucose (FBG) level of rats in each group; FIG. 71B shows blood glucose levels of rats in each group at different time points during a glucose tolerance test; and FIG. 71C shows an area under the curve (AUC) for rats in each group during a glucose tolerance test;

DETAILED DESCRIPTION OF THE EMBODIMENTS

The present disclosure will be described in detail below with reference to examples, but the present disclosure is not limited to these examples.

The synthesis of the CYP2E1 inhibitors in Examples 2, 3, 4, and 5 of the present disclosure adopts a high-resolution mass spectrometer of American Waters, with a model of Q-Tof micro.

The synthesis of the CYP2E1 inhibitors in Examples 2, 3, 4, and 5 of the present disclosure adopts a nuclear magnetic resonance (NMR) instrument of German Bruker, with a model of DPX-400.

In Examples 8, 9, and 10 of the present disclosure, the in vivo and in vitro CYP2E1 inhibitory effects are determined by a high performance liquid chromatograph of Agilent Technologies Inc., with a model of Agilent 1260.

In Example 17 of the present disclosure, a mouse glioma model is prepared by a brain stereotaxic instrument of Shanghai Puxin Instrument Technology Co., Ltd., with a model of ZR-09.

Example 1 Preparation of a Human Liver Microsome

Differential centrifugation was adopted. A liver specimen was taken out, thawed, weighed, and mixed with a 50 mM Tris-HCl buffer (pH=7.0) (including 150 mM KCl and 2 mM EDTA) in a ratio of 1:4 (W/V), and a resulting mixture was ground with a glass homogenizer to obtain a liver homogenate; the liver homogenate was centrifuged at 4° C. and 9,000×g for 20 min, and a resulting supernatant was centrifuged at 4° C. and 100,000×g for 60 min; a resulting precipitate was resuspended in 4 mL of 0.15 M Tris-HCl (pH=7.6), and a resulting suspension was centrifuged at 100,000 g and 4° C. for 60 min; a resulting precipitate was added to a 0.25 M sucrose suspension in a ratio of 1:2 (W/V) to finally obtain 2 mL of a microsome suspension per g of the liver tissue; and the microsome suspension was dispensed, stored in liquid nitrogen overnight, and then transferred to −80° C. the next day for long-term storage. All of the above operations were conducted in an ice bath. A protein content (mg/mL) in a microsome was determined by the Bradford method.

Liver microsomes in both liver damage patients and healthy individuals were prepared by this method.

Example 2 Synthesis of SMI0

Figure 1:
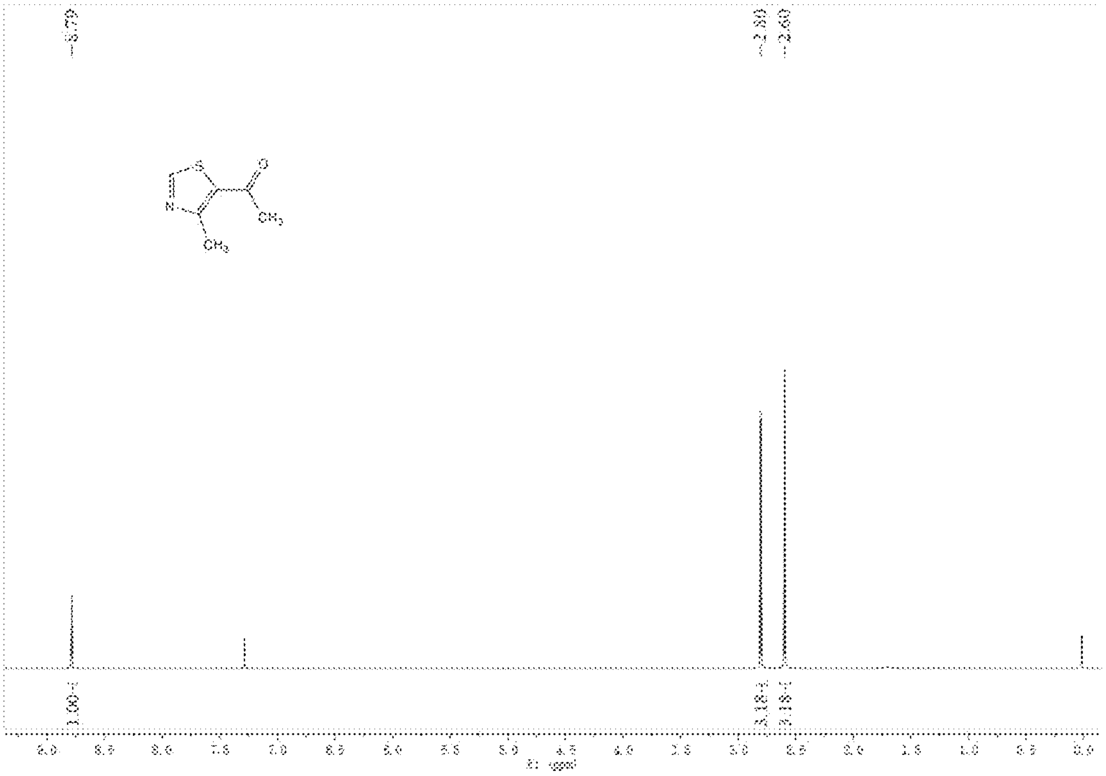
FIG. 1 is a hydrogen nuclear magnetic resonance (HNMR) spectrum of the compound SMI0.

Ethyl 4-methylthiazole-5-carboxylate (1 mol) and NaOH (1.6 mol) were mixed in a mixed solution of ethanol and water, and a reaction was conducted overnight at room temperature; when it was detected by thin layer chromatography (TLC) (pure ethyl acetate) that the reaction was completed, the ethanol was completely evaporated under reduced pressure, a pH was adjusted with concentrated sulfuric acid to 2 to 3, and a resulting system was subjected to suction filtration to obtain a solid; the solid was washed and dried; 4-methylthiazole-5-carboxylic acid (1 mol) and DDC (1 mol) were added to anhydrous THF, and a resulting mixture was stirred at room temperature and subjected to activation for 2 h to 3 h; dimethylhydroxylamine hydrochloride (1.2 mol) was added, TEA (1.5 mol) was added dropwise, and a resulting mixture was stirred overnight at room temperature; when it was detected by TLC (PE:EA=3:1) that the reaction was completed, THF was completely evaporated under reduced pressure, and extraction was conducted three times with ethyl acetate; a resulting organic phase was washed two times with a saturated sodium bicarbonate aqueous solution, dried with anhydrous magnesium sulfate, subjected to suction filtration, and subjected to evaporation under reduced pressure; a product (1 mol) was dissolved in anhydrous THF and then pre-cooled in a cold trap under nitrogen protection, and a Grignard reagent $CH_3MgCl$ (1.5 mol) was added dropwise at −10° C. to 15° C.; when it was detected by TLC (PE:EA=3:1) that the reaction was completed, a resulting reaction system was quenched with saturated $NH_4Cl$, and extraction was conducted with ethyl acetate; a resulting organic phase was dried with anhydrous magnesium sulfate, subjected to suction filtration, and subjected to vacuum evaporation; and a crude product was subjected to vacuum distillation to obtain a pure product. NMR data for the product were as follows (as shown in FIG. 1):

$^1H$ NMR (400 MHz, $CDCl_3$) δ 8.79 (s, 1H), 2.80 (s, 3H), 2.60 (s, 3H).

Example 3 Synthesis of Compound SMI7

Figure 2:
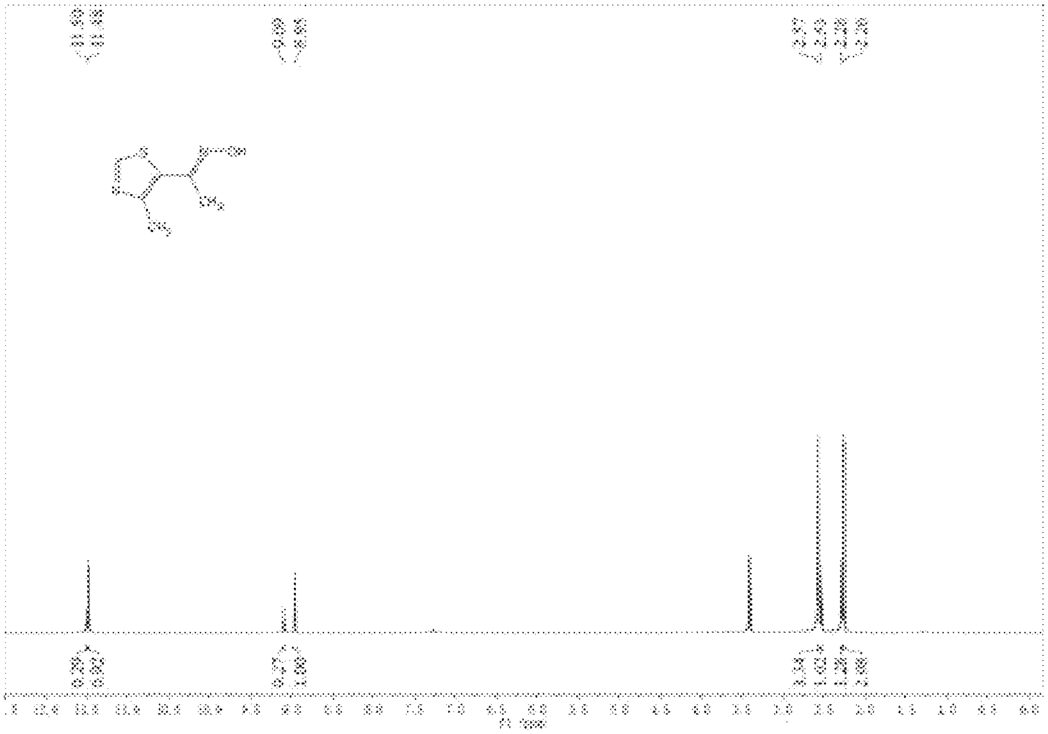
FIG. 2 is an HNMR spectrum of the compound SMI7.

Hydroxylamine hydrochloride (3 mmol) was added to a round-bottom flask, then 3 mL of ethanol was added, and a resulting mixture was stirred at 25° C. for 10 min; then 3 mL of a 1 M NaOH solution was added, then SMI0 (3 mmol) was added, and a reaction was conducted in an 80° C. oil batch under reflux; when it was detected by TLC that the reaction was completed, a resulting reaction system was neutralized with 10% dilute hydrochloric acid, and extraction was conducted with water and ethyl acetate; resulting organic phases were combined, dried with anhydrous magnesium sulfate, and subjected to suction filtration to remove the magnesium sulfate; and a filtrate was subjected to vacuum concentration and then to silica gel column chromatography with petroleum ether and ethyl acetate in a ratio of 1:2 as an eluent to obtain a compound SMI7. NMR data of the product were as follows (as shown in FIG. 2):

$^1H$ NMR (400 MHz, DMSO) δ 11.50 (s, 2/3H), 11.48 (s, 1/3H), 9.09 (s, 1/3H), 8.95 (s, 2/3H), 2.57 (s, 2/3H), 2.53 (s, 1/3H), 2.28 (s, 1/3H), 2.26 (s, 2/3H).

Example 4 Synthesis of Compound SMI16

Figure 3:
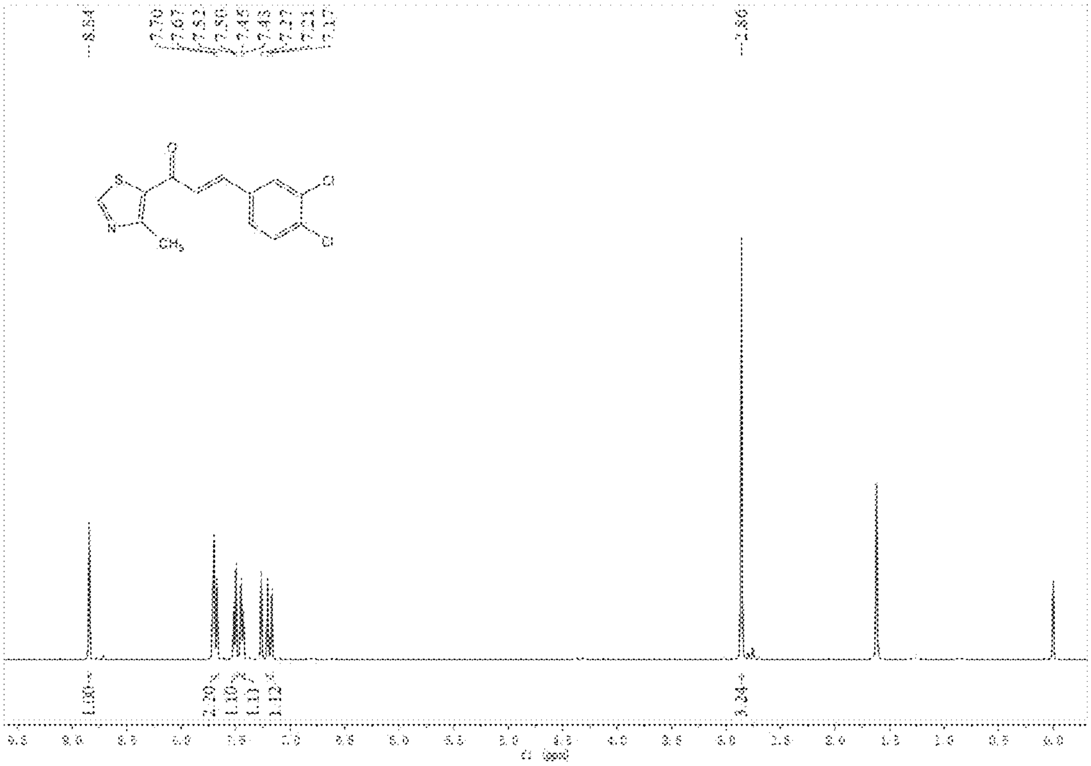
FIG. 3 is an HNMR spectrum of the compound SMI16.

3,4-Dichlorobenzaldehyde (1 mmol) was added to a round-bottom flask, 2 mL of absolute ethanol was added, and a resulting mixture was stirred at 50° C. for dissolution; 30 μL of a 3 M KOH solution was added, then SMI0 (1 mmol) was added, and a resulting mixture was stirred at 50° C.; when it was detected by TLC that the reaction was completed, a resulting reaction system was neutralized with 10% dilute hydrochloric acid, and extraction was conducted with water and ethyl acetate; resulting organic phases were combined, dried with anhydrous magnesium sulfate, and subjected to suction filtration to remove the magnesium sulfate; and a filtrate was subjected to vacuum concentration and then to silica gel column chromatography with petroleum ether and ethyl acetate in a ratio of 2:1 as an eluent to obtain a compound SMI16. NMR data of the product were as follows (as shown in FIG. 3):

$^1$H NMR (400 MHz, $CDCl_3$) δ 8.84 (s, 1H), 7.68 (d, J=11.2 Hz, 2H), 7.51 (d, J=8.3 Hz, 1H), 7.44 (d, J=8.2 Hz, 1H), 7.19 (d, J=15.5 Hz, 1H), 2.86 (s, 3H).

Example 5 Synthesis of Compound SMI20

Figure 4:
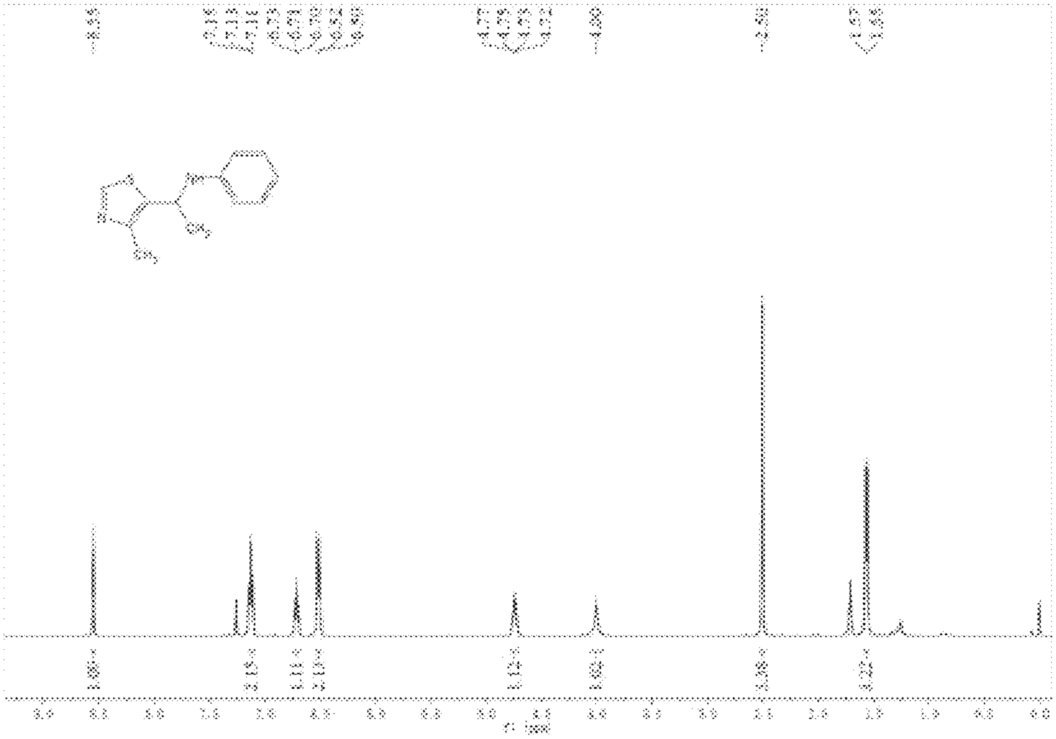
FIG. 4 is an HNMR spectrum of the compound SMI20.

Phenylamine (2 mmol) and SMI0 (2 mmol) were added to a round-bottom flask, 3 mL of absolute ethanol was added, and a resulting mixture was stirred at 25° C. for 10 min; $BH_3CNNa$ (2 mmol) and acetic acid (1 mmol) were added, and a resulting mixture was stirred at 25° C.; when it was detected by TLC that the reaction was completed, a resulting reaction system was neutralized with 10% dilute hydrochloric acid, and extraction was conducted with water and ethyl acetate; resulting organic phases were combined, dried with anhydrous magnesium sulfate, and subjected to suction filtration to remove the magnesium sulfate; and a filtrate was subjected to vacuum concentration and then to silica gel column chromatography with petroleum ether and acetone in a ratio of 4:1 as an eluent to obtain a compound SMI20. NMR data of the product were as follows (as shown in FIG. 4):

$^1$H NMR (400 MHz, $CDCl_3$) δ 8.55 (s, 1H), 7.13 (t, J=7.7 Hz, 2H), 6.71 (t, J=7.2 Hz, 1H), 6.51 (d, J=7.9 Hz, 2H), 4.74 (q, J=6.2 Hz, 1H), 4.00 (s, 1H), 2.50 (s, 3H), 1.56 (d, J=6.6 Hz, 3H).

Example 6 Synthesis of a Hydrochloride of SMI0

Figure 5:
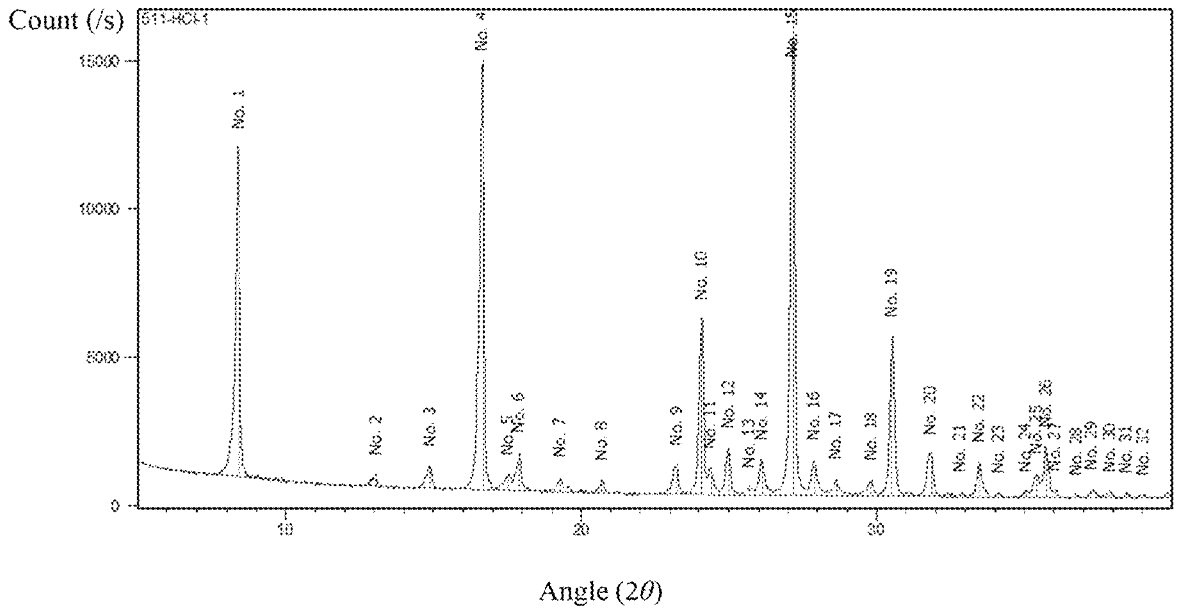
FIG. 5 is an XRPD pattern of a crystal form A of a hydrochloride of SMI0.
Figure 6:
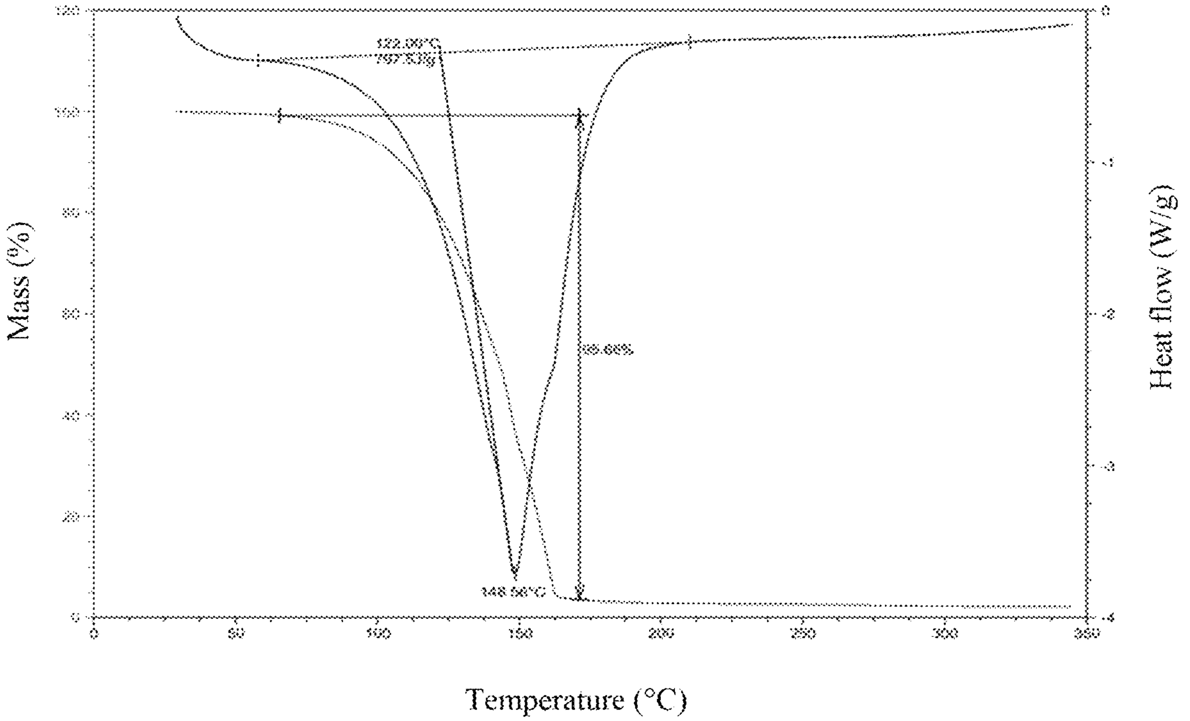
FIG. 6 is a DSC-TGA pattern of a crystal form A of a hydrochloride of SMI0.

SMI0 (1 g, 7.08 mmol) was added to a round-bottom flask, then 5 mL of ethanol was added for dissolution, and 11 mL of a 1 mol/L hydrochloric acid-ethanol solution was slowly added dropwise under stirring to allow a reaction for 1 h at room temperature; a resulting reaction system was subjected to vacuum concentration and cooled for crystallization, and a resulting mixture was filtered; and a filter cake was washed with 0.5 mL of cold absolute ethanol and then dried to obtain 1.06 g of a white solid, with a yield of 85%, a purity of 99.8% (HPLC), and a melting range of 160° C. to 162° C. An XRPD pattern of a crystal form A of the hydrochloride of SMI0 was shown in FIG. 5; and a DSC-TGA pattern of the crystal form A was shown in FIG. 6.

Example 7 Synthesis of a Sulfate of SMI0

Figure 7:
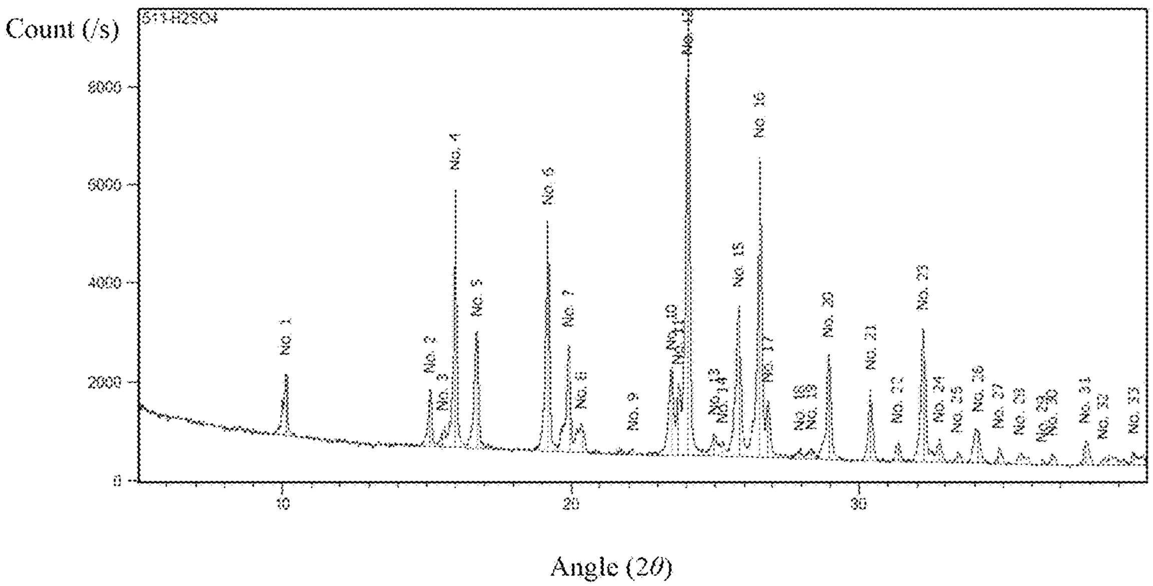
FIG. 7 is an XRPD pattern of a crystal form B of a sulfate of SMI0.
Figure 8:
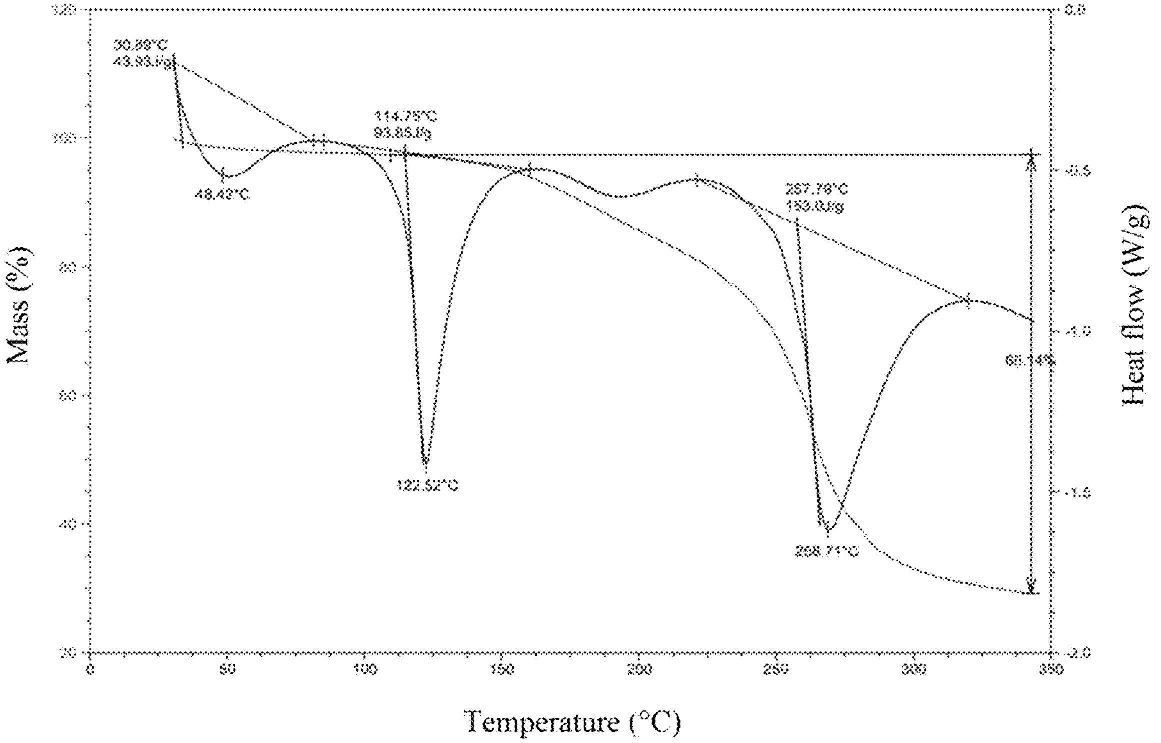
FIG. 8 is a DSC-TGA pattern of a crystal form B of a sulfate of SMI0.

SMI0 (1 g, 7.08 mmol) was added to a round-bottom flask, then 5 mL of ethanol was added for dissolution, and 8 mL of a 1 mol/L sulfuric acid-ethanol solution was slowly added dropwise under stirring to allow a reaction for 1 h at room temperature; and the solvent was completely evaporated, and then recrystallization was conducted with a small amount of methanol to obtain 0.85 g of a yellow solid, with a yield of 70% and a purity of 99.5% (HPLC). An XRPD pattern of a crystal form B of the sulfate of SMI0 was shown in FIG. 7; and a DSC-TGA pattern of the crystal form B was shown in FIG. 8.

Example 8 Determination of an Inhibitory Effect on Metabolic Activity of CYP2E1

CZX was used as a probe substrate to detect an inhibitory effect of an inhibitor to be tested on the metabolic activity of a mixed liver microsome CYP2E1 of a healthy individual ($IC_{50}$: half inhibition concentration; $K_i$: inhibition constant; the smaller the $IC_{50}$ and the smaller the $K_i$, the higher the inhibition intensity of the inhibitor), thereby determining an inhibitory effect of the inhibitor to be tested on the human liver microsome CYP2E1.

Determination of $IC_{50}$ for a CYP2E1 Inhibitory Effect

An incubation system in a total volume of 100 μL was adopted, including a substrate, an inhibitor of different concentrations, a liver microsomal protein, and phosphate-buffered saline (PBS). The incubation system was pre-incubated in a 37° C. water bath for 5 min, reduced coenzyme was added to allow a reaction for 30 min, and then the reaction was terminated in an ice bath. In a specific experiment, a concentration of an inhibitor can be selected as required.

In this example, the incubation system includes 62.5 μM CZX, 100 mM (pH=7.4) PBS, 0.3 mg/mL liver microsomal protein, and 1 mM NADPH.

In other preferred examples, the incubation system may include 7.8 μM to 1,000 μM CZX as a substrate. A concentration of the liver microsomal protein may be 0.1 mg/mL to 0.5 mg/mL. 50 mM to 100 mM PBS or 50 mM to 100 mM Tris-HCL buffer can be used as required.

An NADPH regeneration system can also be used. Preferably, the incubation system includes 62.5 μM CZX, 100 mM (pH=7.4) PBS, 0.3 mg/mL liver microsomal protein, and 1 mM NADPH.

In this example, the reaction is terminated with 1 mL of ethyl acetate. In other preferred examples, the reaction may also be terminated with 1 mL of methyl tert-butyl ether (MTBE), 1 mL of diethyl ether, or 100 μL of methanol.

Determination of $K_i$ for a CYP2E1 Inhibitory Effect

When it was determined that an inhibitor had a prominent inhibitory effect on CYP2E1, different concentrations of a substrate and different concentrations of the inhibitor were selected to conduct an in vitro metabolic incubation inhibition test, and an inhibition constant $K_i$ of the inhibitor for the metabolism of CZX by CYP2E1 was calculated.

An incubation system in a total volume of 100 μL was adopted, including a substrate, an inhibitor of different concentrations, a liver microsomal protein, and PBS. The incubation system was pre-incubated in a 37° C. water bath for 5 min, reduced coenzyme was added to allow a reaction for a specified time, and then the reaction was terminated in an ice bath.

In this example, the incubation system includes 15.6 μM, 31.25 μM, 62.5 μM, 125 μM, or 250 μM CZX; an inhibitor of a specified concentration determined based on the determined $IC_{50}$ according to a ratio of 1/4 to 4; 100 mM (pH=7.4) PBS; 0.3 mg/mL liver microsomal protein; and 1 mM NADPH.

In other preferred examples, the incubation system may include 7.8 μM to 1,000 μM CZX as a substrate, and more preferably, the incubation system may include 15.6 μM to 250 μM (15.6 μM, 31.25 μM, 62.5 μM, 125 μM, and 250 μM) CZX. A concentration of the liver microsomal protein may be 0.1 mg/mL to 0.5 mg/mL. 50 mM to 100 mM PBS or 50 mM to 100 mM Tris-HCL buffer can be used as required.

1 mM NADPH or an NADPH regeneration system can also be used. The NADPH regeneration system includes 1.3 mM $NADP^+$, 3.3 mM glucose-6-phosphate, 0.4 U/mL glucose dehydrogenase (GDH), and 3.3 mM magnesium chloride.

In this example, the reaction is terminated with 1 mL of ethyl acetate. In other preferred examples, the reaction may also be terminated with 1 mL of MTBE, 1 mL of diethyl ether, or 100 μL of methanol.

Determination of Selectivity of a CYP2E1 Inhibitor

With a mixed liver microsome of a healthy individual as a research object, probe drugs CYP1A2, CYP2A6, CYP2B6, CYP2C8, CYP2C9, CYP2C19, CYP2D6, CYP2E1, and CYP3A4 were selected to determine an in vitro inhibitory effect of an inhibitor to be tested on the metabolism of the probe drugs CYP1A2, CYP2A6, CYP2B6, CYP2C8, CYP2C9, CYP2C19, CYP2D6, CYP2E1, and CYP3A4 for the mixed liver microsome of the healthy human, and the selectivity of the inhibitor to be tested for a CYP2E1 inhibitory effect was evaluated.

The CYP1A2 probe is 6.25 μM to 800 μM phenacetin or 27.5 μM to 12,520 μM caffeine;

- the CYP2A6 probe is 0.156 μM to 20 μM coumarin or 12.5 μM to 2,000 μM nicotine;
- the CYP2B6 probe is 7.8 μM to 500 μM bupropion or 0.25 mM to 30 mM cyclophosphamide;
- the CYP2C8 probe is 2.5 μM to 80 μM paclitaxel or 0.125 μM to 128 μM amodiaquine;
- the CYP2C9 probe is 31.25 μM to 2,000 μM tolbutamide or 0.1 μM to 200 μM diclofenac;
- the CYP2C19 probe is 3.9 μM to 500 μM omeprazole or 1.95 μM to 1,000 μM mephenytoin;
- the CYP2D6 probe is 0.625 μM to 96 μM dextromethorphan or 0.0195 μM to 80 M propafenone; and
- the CYP3A4 probe is 0.39 μM to 50 μM midazolam or 1.98 μM to 1,000 μM testosterone.

An incubation system in a total volume of 100 μL was adopted, including a substrate, an inhibitor of different concentrations, a liver microsomal protein, and PBS. The incubation system was pre-incubated in a 37° C. water bath for 5 min, reduced coenzyme was added to allow a reaction for a specified time, and then the reaction was terminated in an ice bath.

In this example, the incubation system includes at least one selected from the group consisting of 62.5 μM phenacetin, 2.5 μM coumarin, 62.5 μM bupropion, 10 μM paclitaxel, 250 μM tolbutamide, 62.5 μM omeprazole, 20 μM dextromethorphan, 62.5 μM CZX, and 1.56 μM midazolam; 100 mM (pH=7.4) PBS; 0.3 mg/mL liver microsomal protein; and 1 mM NADPH.

In other preferred examples, the incubation system may include 7.8 μM to 1,000 μM CZX as a substrate. A concentration of the liver microsomal protein may be 0.1 mg/mL to 0.5 mg/mL. The buffer may be one selected from the group consisting of 50 mM PBS, 100 mM PBS, 50 mM Tris-HCL buffer, and 100 mM Tris-HCL buffer. 1 mM NADPH or an NADPH regeneration system can also be used.

In this example, the reaction is terminated with 1 mL of ethyl acetate. In other preferred examples, the reaction may also be terminated with 1 mL of MTBE, 1 mL of diethyl ether, or 100 L of methanol.

Example 9 In Vitro Screening Test Results of CYP2E1 Inhibitors

SMI0 ($IC_{50}$ for 2E1 inhibition: 1.64 μM; $IC_{50}$ for 2A6 inhibition: 76.20 μM; and no significant inhibitory effect for other CYP enzymes):

SMI0

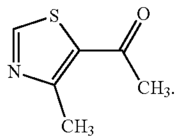

Figure 9:
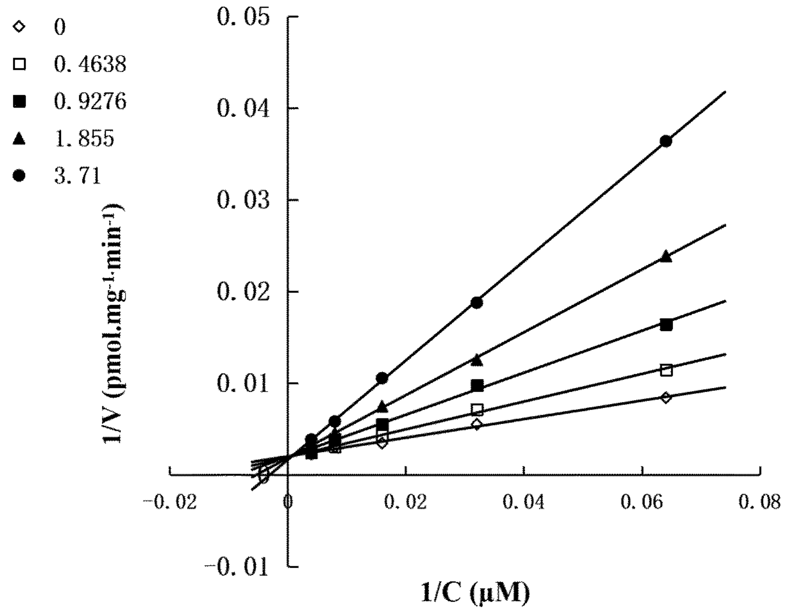
FIG. 9 is a double-reciprocal plot of an inhibitory effect of the compound SMI0 on human hepatic metabolism of chlorzoxazone (CZX)

As shown in FIG. 9, a 100 μL incubation system is adopted for all reactions, with CZX concentrations of 15.6 μM, 31.2 μM, 62.5 μM, 125 μM, and 250 μM and SMI0 series concentrations of 0 μM, 0.4638 μM, 0.9276 μM, 1.855 μM, and 3.710 μM. All experimental data are derived from a mean of three independent experiments. FIG. 9 is a double-reciprocal plot of an inhibitory effect of the compound SMI0 on human hepatic metabolism of CZX. It indicates that the compound SMI0 is a hybrid inhibitor for CYP2E1.

Figure 10:
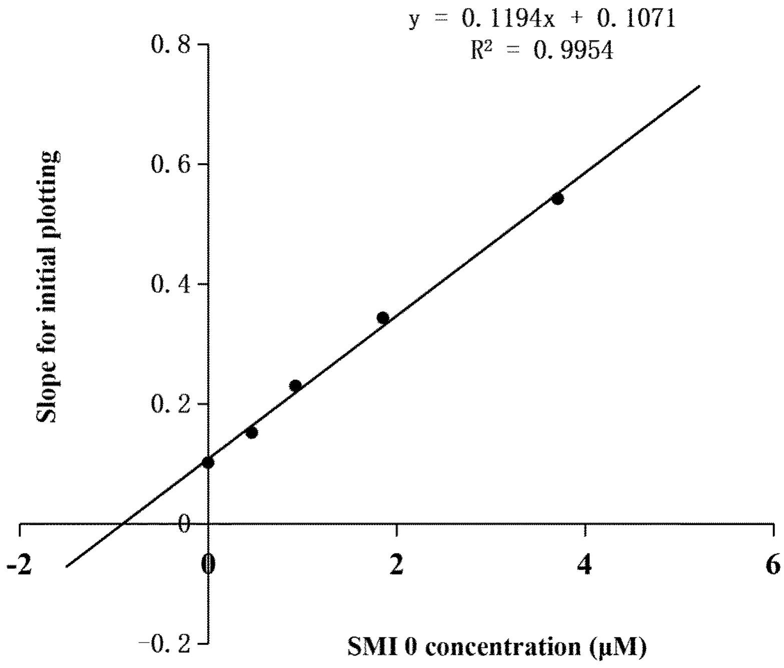
FIG. 10 is a secondary plot based on the double-reciprocal plot of an inhibitory effect of the compound SMI0 on metabolism of CZX by human hepatic CYP2E1.

FIG. 10 is a secondary plot based on the double-reciprocal plot of an inhibitory effect of the compound SMI0 on metabolism of CZX by human hepatic CYP2E1. The series concentrations of SMI0 (0 μM, 0.4638 μM, 0.9276 μM, 1.855 μM, and 3.710 μM) were subjected to linear regression with slopes of different inhibition curves, and an absolute value of an intersection point between a straight line and a horizontal axis was $K_i$, which was 0.8970 μM.

Figure 11A:
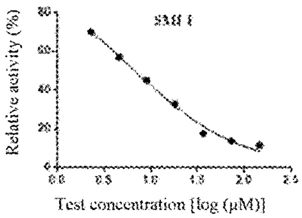
FIGS. 11A-11U show inhibitory effects of 21 small molecule compounds on the in vitro metabolic activity of CYP2E1.
Figure 11B:
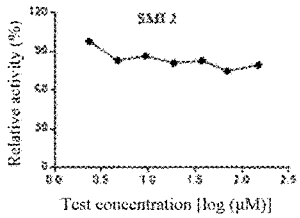
Figure 11C:
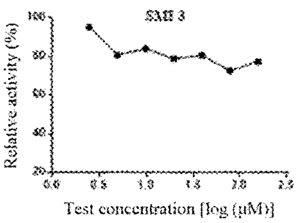
Figure 11D:
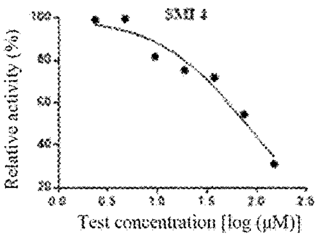
Figure 11E:
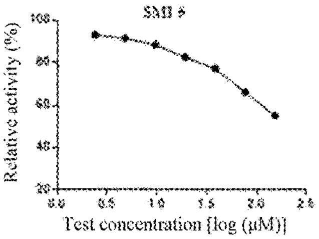
Figure 11F:
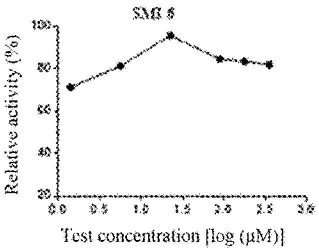
Figure 11G:
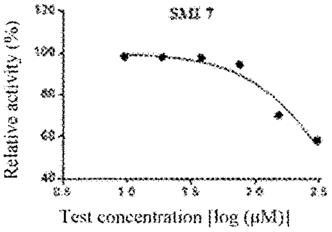
Figure 11H:
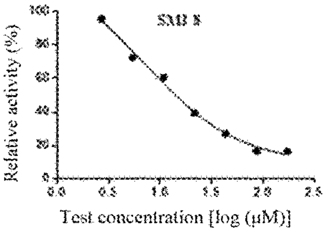
Figure 11I:
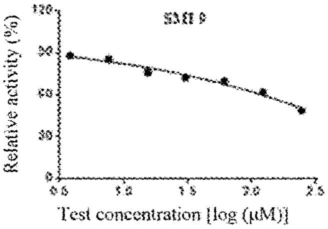
Figure 11J:
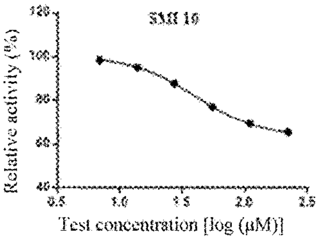
Figure 11K:
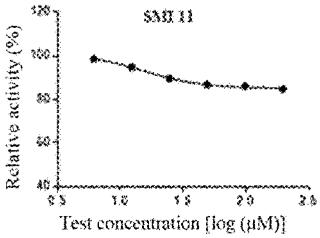
Figure 11L:
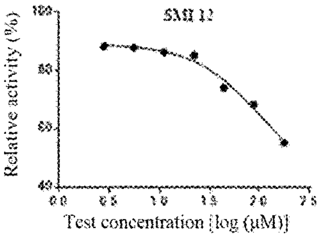
Figure 11M:
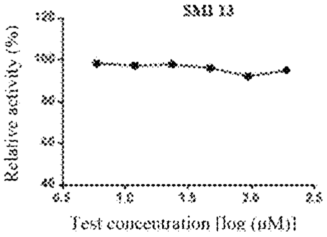
Figure 11N:
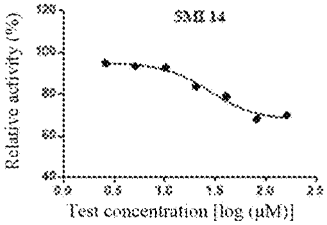
Figure 11O:
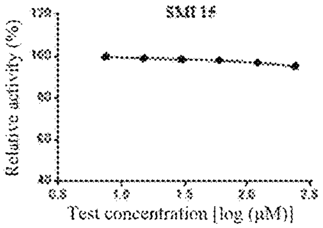
Figure 11P:
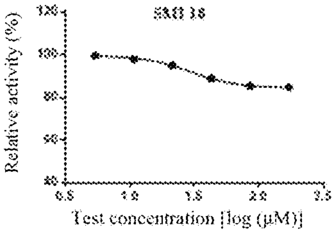
Figure 11Q:
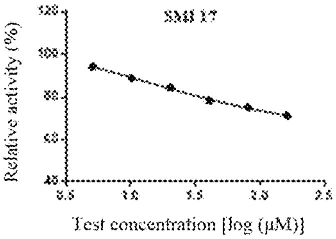
Figure 11R:
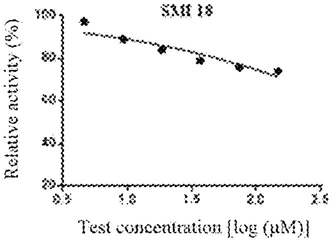
Figure 11S:
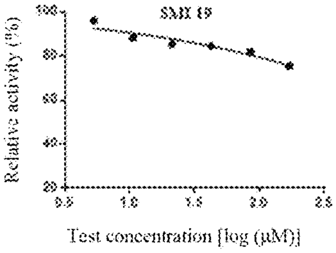
Figure 11T:
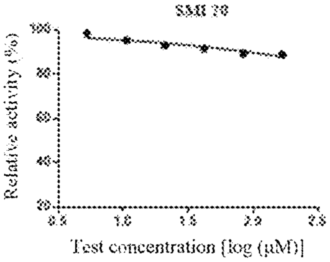
Figure 11U:
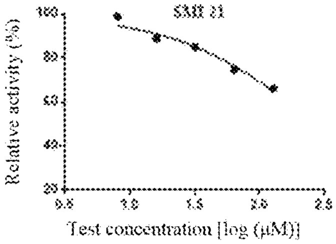

With reference to the specific research method in Example 8, inhibitory effects of 21 small molecule compounds (Table 1) on CYP2E1 were tested in vitro. Results showed that SMI1 and SMI8 each had a significant inhibitory effect on CYP2E1, and $IC_{50}$ values of SMI1 and SMI8 for CYP2E1 inhibition were 7.99 μM and 17.03 μM, respectively; SMI10 had a slight inhibitory effect on CYP2E1, with $IC_{50}$ of 114.5 μM; and compared with SMI0, SMI1, SMI8, and SMI10, other small molecules had a weak inhibitory effect on CYP2E1 (as shown in FIGS. 11A-11U).

In addition, selectivity studies showed that $IC_{50}$ of the inhibition of SMI1 for CYP2A6 was 55.63 μM and $IC_{50}$ of the inhibition of SMI1 for CYP2C9 was 1.86 μM. Structures of the 21 small molecules were shown in Table 1.

TABLE 1

| No. | Structural formula |
|---|---|
| SMI1 | 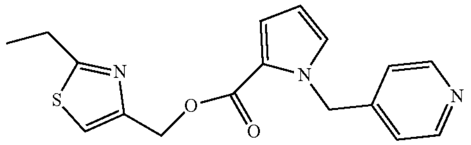 [SMILES: CCc1nc(COC(=O)c2cccn2Cc2ccncc2)cs1] |
| SMI2 | 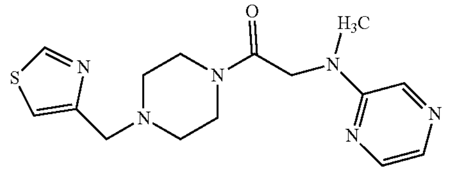 [SMILES: CN(CC(=O)N1CCN(Cc2cscn2)CC1)c1cnccn1] |
| SMI3 | 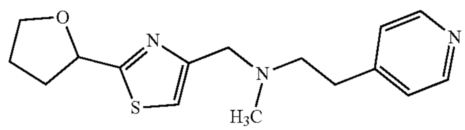 [SMILES: CN(CCc1ccncc1)Cc1csc(C2CCCO2)n1] |
| SMI4 | 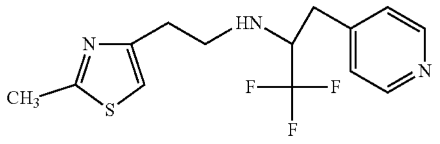 [SMILES: Cc1nc(CCNC(Cc2ccncc2)C(F)(F)F)cs1] |
| SMI5 | 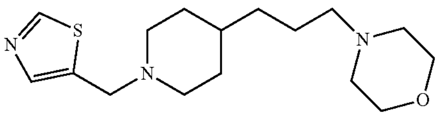 [SMILES: c1ncc(CN2CCC(CCCN3CCOCC3)CC2)s1] |

TABLE 1-continued

| No. | Structural formula |
|---|---|
| SMI6 | 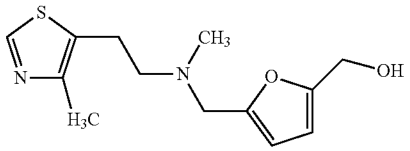 [SMILES: Cc1ncsc1CCN(C)Cc1ccc(CO)o1] |
| SMI7 | 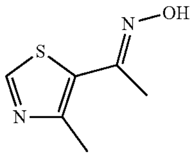 |
| SMI8 | 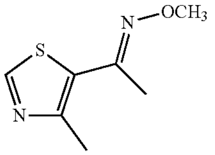 |
| SMI9 | 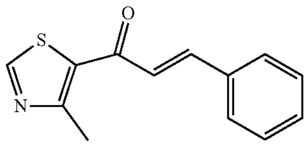 [SMILES: Cc1ncsc1C(=O)/C=C/c1ccccc1] |
| SMI10 | 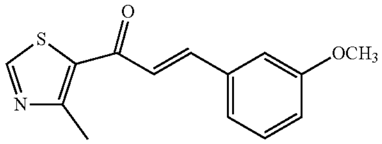 [SMILES: COc1cccc(/C=C/C(=O)c2scnc2C)c1] |
| SMI11 | 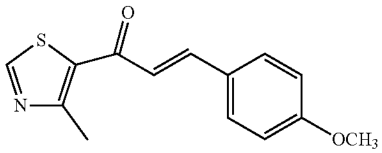 [SMILES: COc1ccc(/C=C/C(=O)c2scnc2C)cc1] |
| SMI12 | 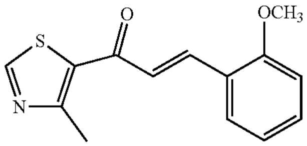 [SMILES: COc1ccccc1/C=C/C(=O)c1scnc1C] |
| SMI13 | 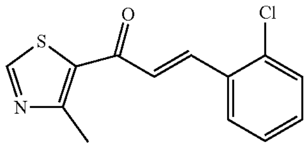 [SMILES: Cc1ncsc1C(=O)/C=C/c1ccccc1Cl] |
| SMI14 | 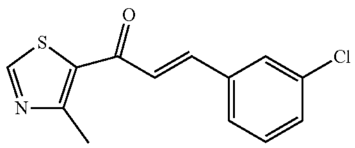 [SMILES: Cc1ncsc1C(=O)/C=C/c1cccc(Cl)c1] |
| SMI15 | 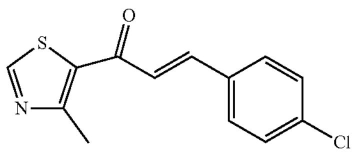 [SMILES: Cc1ncsc1C(=O)/C=C/c1ccc(Cl)cc1] |

TABLE 1-continued

| No. | Structural formula |
|---|---|
| SMI16 | 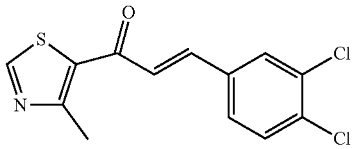 [SMILES: Cc1ncsc1C(=O)/C=C/c1ccc(Cl)c(Cl)c1] |
| SMI17 | 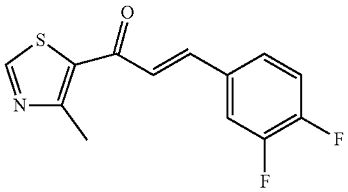 [SMILES: Cc1ncsc1C(=O)/C=C/c1ccc(F)c(F)c1] |
| SMI18 | 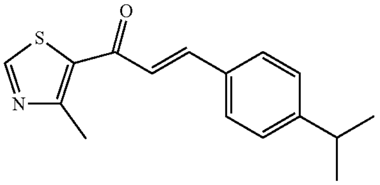 [SMILES: Cc1ncsc1C(=O)/C=C/c1ccc(C(C)C)cc1] |
| SMI19 | 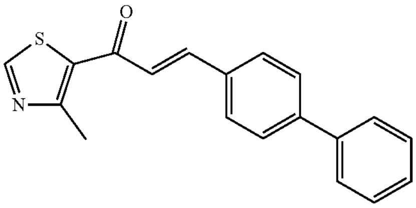 [SMILES: Cc1ncsc1C(=O)/C=C/c1ccc(-c2ccccc2)cc1] |
| SMI20 | 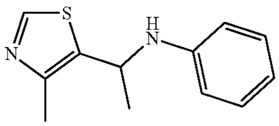 |
| SMI21 | 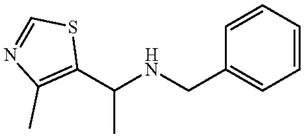 [SMILES: Cc1ncsc1C(C)NCc1ccccc1] |

Example 10 In Vivo Inhibition Test Results of the Compound SMI0 for CYP2E1

Experimental method: An inhibitory effect of the compound SMI0 on CYP2E1 in rats was investigated by a self-controlled crossover experiment design. In a first round of experiments, DEN alone was intraperitoneally injected at 50 mg/kg (30 SD rats in total) in the first week; after a one-week interval, a second round of experiments were conducted as follows: each rat was first intragastrically administered with the compound SMI0 at a low, medium, or high dose (6 mg/kg, 30 mg/kg, or 150 mg/kg), and 5 min later, each rat was intraperitoneally injected with DEN at 50 mg/kg (10 rats were set for each of low, medium, and high doses); blood was collected at 2 min, 7 min, 15 min, and 30 min and 1 h, 2 h, 4 h, 6 h, 9 h, 12 h, 24 h, 36 h, 48 h, and 60 h; a DEN concentration in plasma was determined at different blood collection time points, and a toxicokinetic parameter of DEN was calculated; and plasma DEN was detected by high performance liquid chromatography (HPLC) as follows: 100 μL of plasma was added to 10 μL of perchloric acid, a resulting mixture was vortexed for 3 min and then centrifuged at 12,000 rpm for 10 min, and 10 μL of a resulting supernatant was collected and injected into an instrument, where the HPLC was conducted with methanol:water=50:50 as a mobile phase and a detection wavelength of 240 nm.

Figure 12:
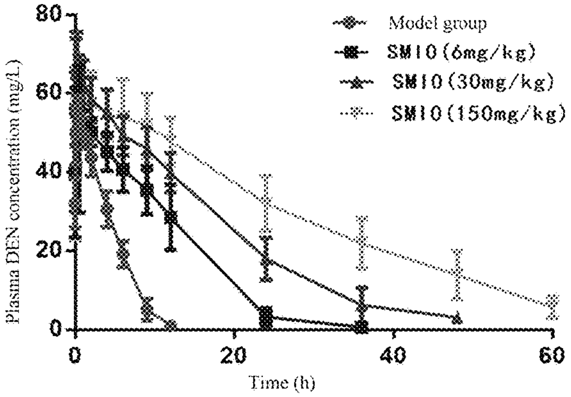
FIG. 12 shows inhibitory effects of the compound SMI0 on the metabolism of DEN by CYP2E1 in rats.
Figure 14A:
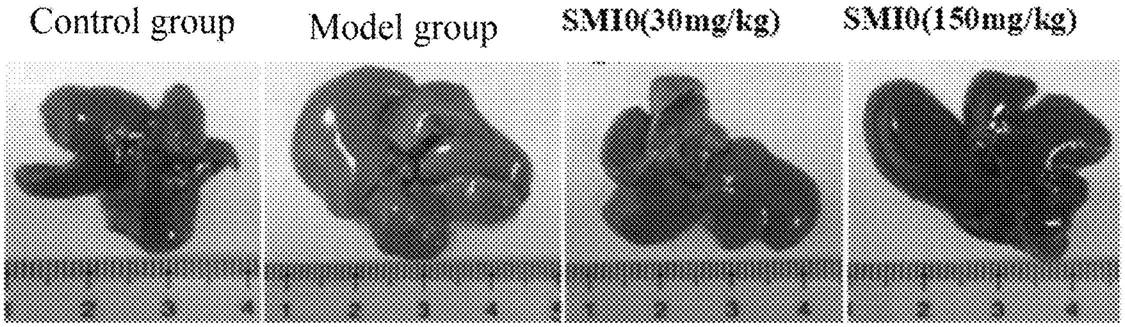
FIGS. 14A-14B show inhibitory effects of the compound SMI0 on mouse liver steatosis and hepatitis models induced by a high-fat diet, where
Figure 14B:
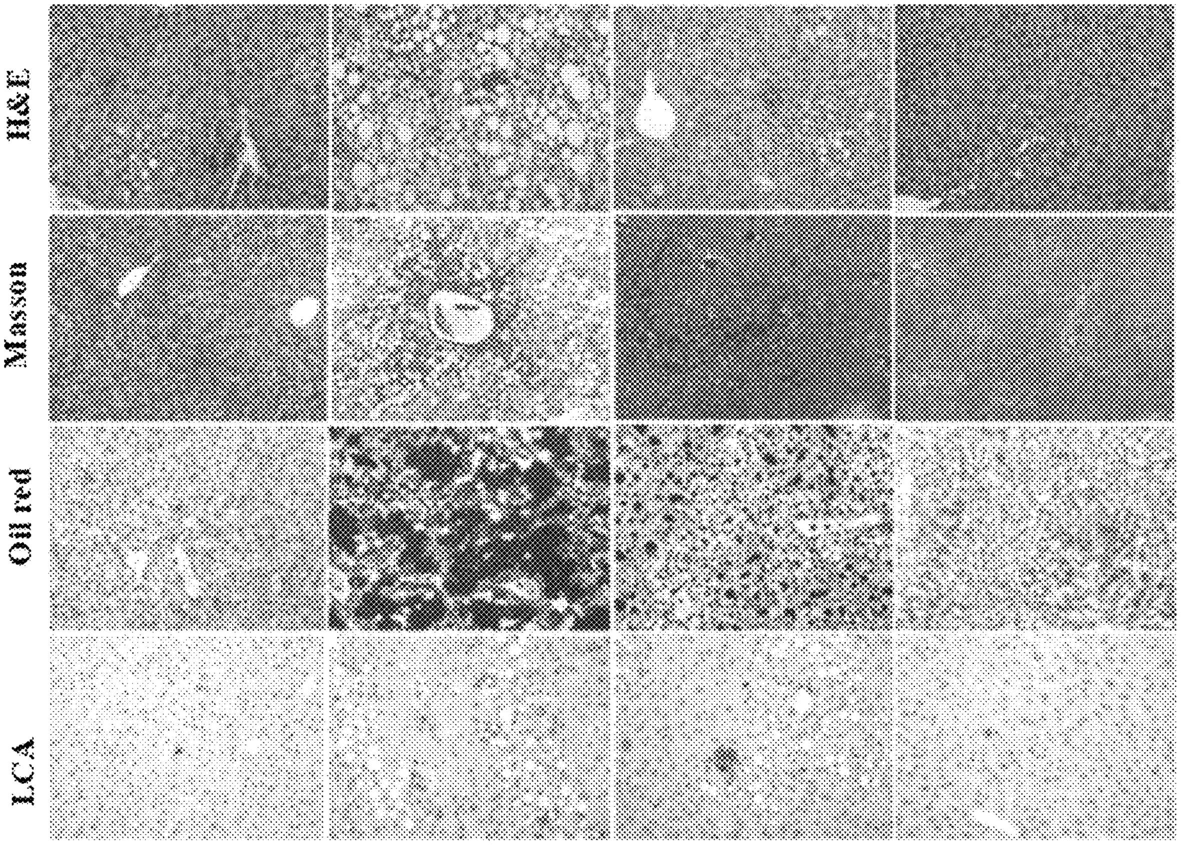
Figure 15A:
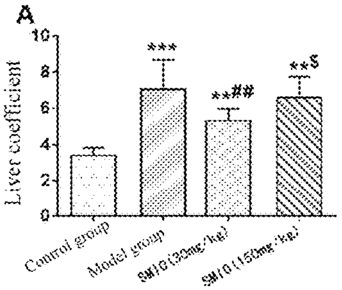
FIGS. 15A-15E show quantitative plotting results of relevant parameters of the inhibition of the compound SMI0 on mouse liver steatosis and hepatitis models induced by a high-fat diet, where
Figure 15B:
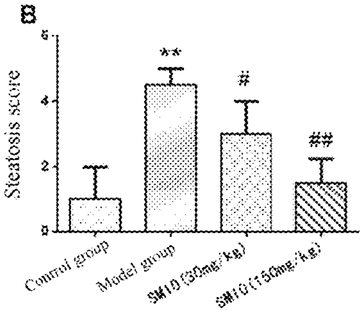
Figure 15C:
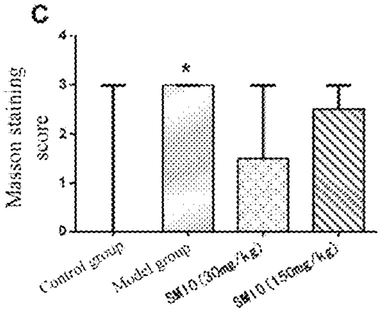
Figure 15D:
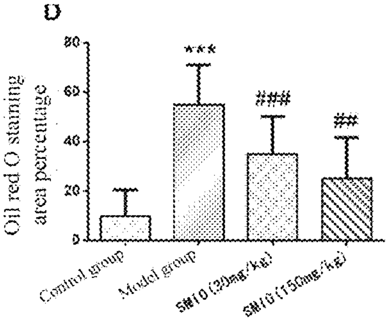
Figure 15E:
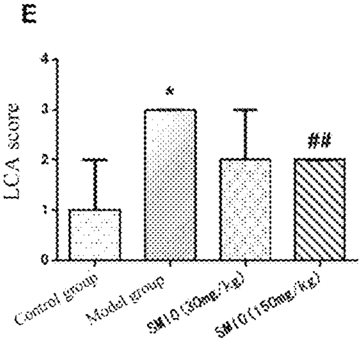
Figure 16A:
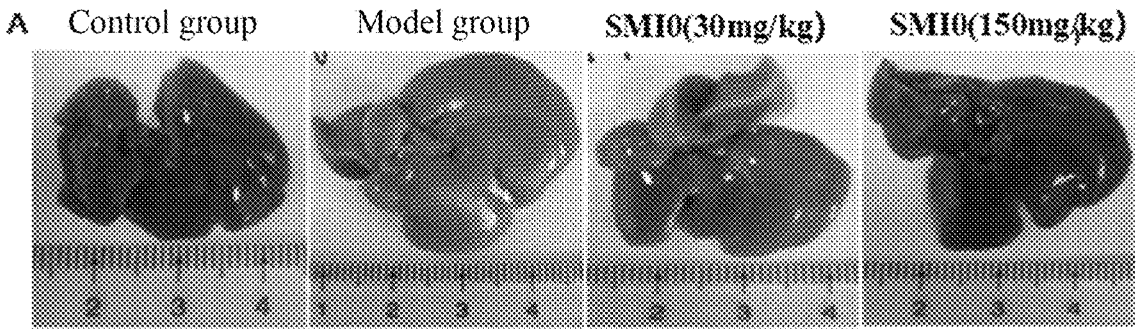
FIGS. 16A-16B show inhibitory effects of the compound SMI0 on mouse liver fibrosis models induced by a high-fat diet, where
Figure 16B:
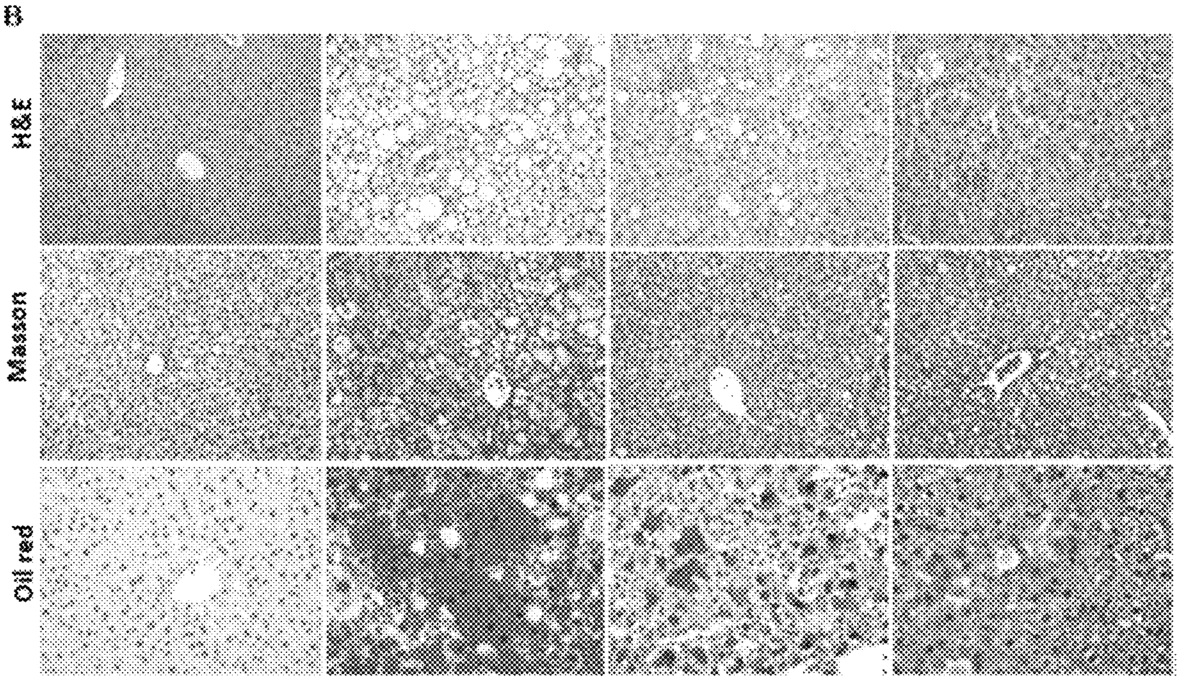
Figure 17A:
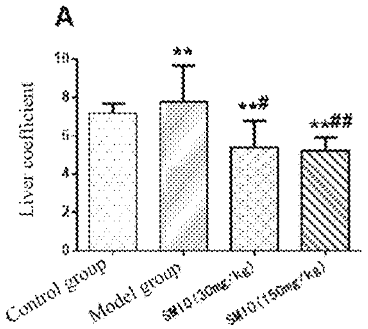
FIGS. 17A-17D show quantitative plotting results of relevant parameters of the inhibition of the compound SMI0 on mouse liver fibrosis models induced by a high-fat diet, where
Figure 17B:
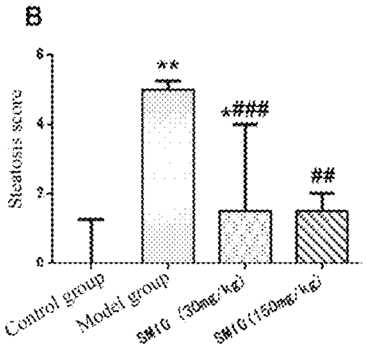
Figure 17C:
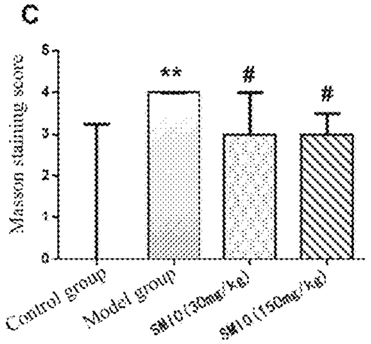
Figure 17D:
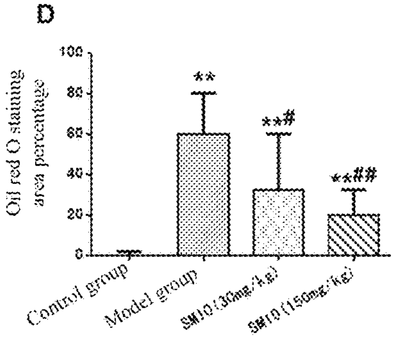
Figure 18A:
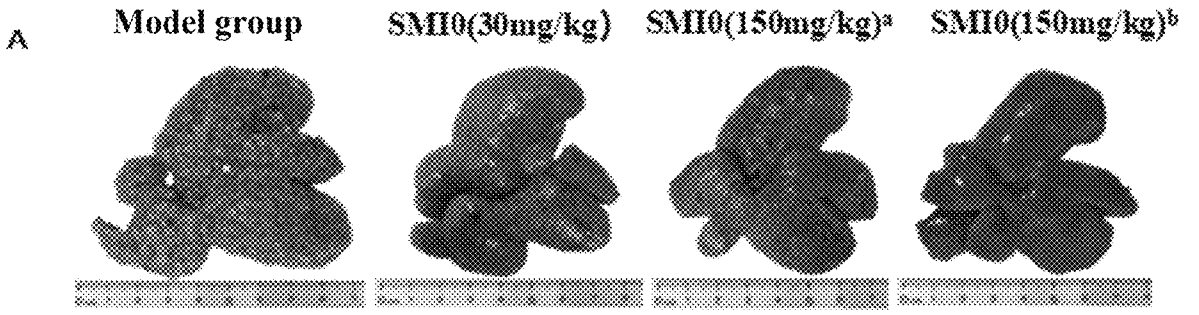
FIGS. 18A-18B show inhibitory effects of the compound SMI0 on DEN-induced rat liver fibrosis models, where
Figure 18B:
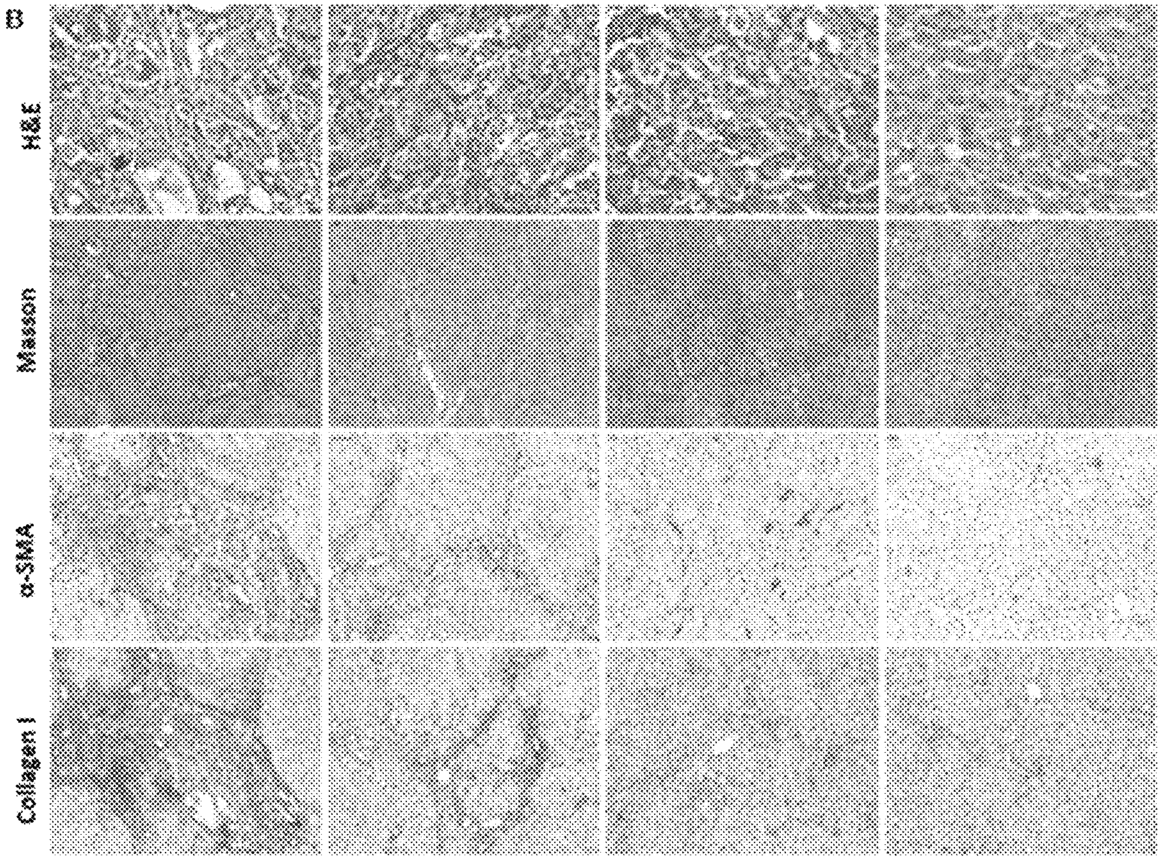
Figure 19A:
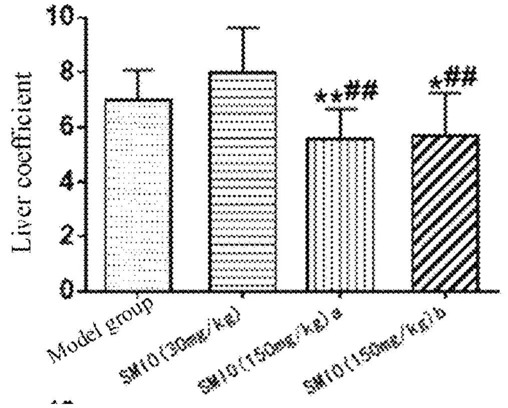
FIGS. 19A-19E show quantitative plotting results of relevant parameters of the inhibition of the compound SMI0 on DEN-induced rat liver fibrosis models, where
Figure 19B:
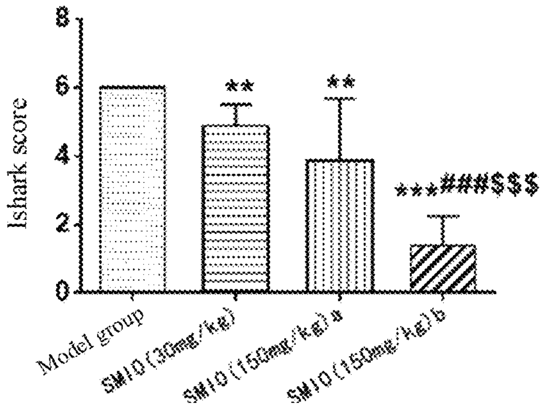
Figure 19C:
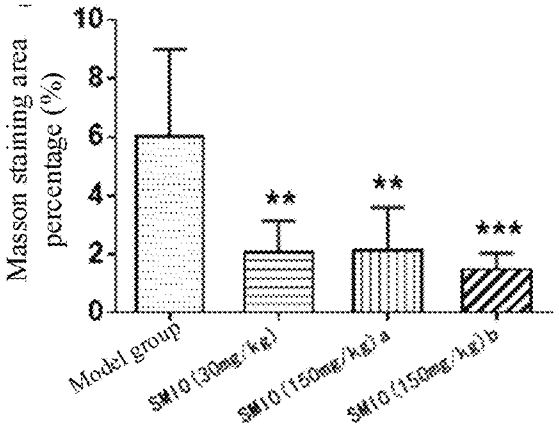
Figure 19D:
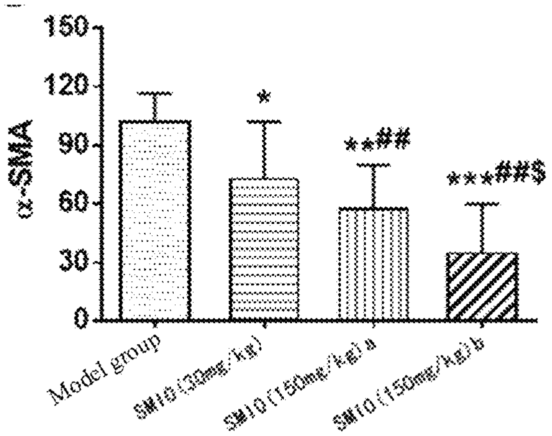
Figure 19E:
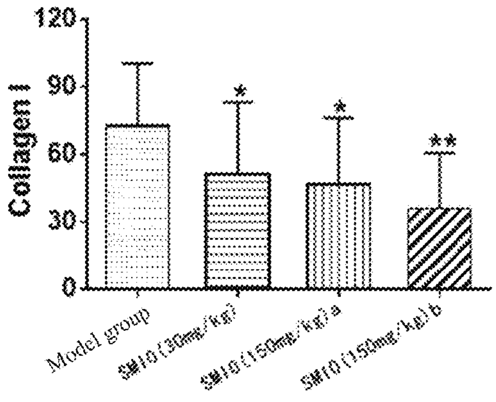

Experimental results: The toxicokinetic parameter of DEN was used to represent CYP2E1 activity, and the influence of the compound SMI0 at low, medium, and high doses on CYP2E1 activity in rats was analyzed. The results showed that, compared with the model group in which DEN was administered alone, SMI0 at low, medium, and high doses could reduce a clearance (CL) of DEN by (63.98±7.78)%, (79.63±7.29)%, and (85.42±3.74)% with inhibition rates of 62.43%, 80.42%, and 86.77%, respectively (as shown in FIG. 12 and Table 2, *P<0.05 and ***P<0.001 vs model group); similarly, SMI0 at low, medium, and high doses could extend a half-life $t_{1/2}$ of DEN by (133.60±116.80)%, (619.97±363.57)%, and (868.70±241.26)%, increase $AUC_{0-t}$ by (196.82±73.63)%, (407.70±184.30)%, and (529.67±153.72)%, and increase $AUC_{0-\infty}$ by (189.99±67.55)%, (455.90±219.26)%, and (626.56±187.15)%, respectively; and the compound SMI0 at a medium dose exhibited a significantly better inhibitory effect than the compound SMI0 at a low dose, and the compound SMI0 at a high dose exhibited a significantly better inhibitory effect than the compound SMI0 at low and medium doses ($^{\#}$P<0.05, $^{\#\#}$P<0.01, $^{\#\#\#}$P<0.001 vs low-dose SMI0 group; $^{\$}$P<0.05, $^{\$\$\$}$P<0.001 vs medium-dose SMI0 group), indicating that the compound SMI0 at different doses could significantly inhibit the metabolic activity of CYP2E1 for DEN in rats, and there was a prominent dose-dependent relationship.

It can be seen from the above results that SMI0 has a significant inhibitory effect on CYP2E1 activity in rats.

TABLE 2

Toxicokinetic parameters for the inhibition of the compound SMI0 on in vivo metabolism of DEN by CYP2E1

| Rat | $C_{max}$ mg/L | $T_{max}$ h | $t_{1/2}$ h | $V_d$ L/kg | CL L/h/kg | $AUC_{0-t}$ mg/L*h | $AUC_{0-\infty}$ mg/L*h |
|---|---|---|---|---|---|---|---|
| Model group | | | | | | | |
| Mean | 55.99 | 0.33 | 2.11 | 0.556 | 0.189 | 260.55 | 270.59 |
| SD | 5.17 | 0.19 | 0.92 | 0.192 | 0.031 | 38.45 | 43.26 |
| SMI0 (6 mg/kg) | | | | | | | |
| Mean | 60.97 | 0.21 | 4.50*** | 0.455 | 0.071*** | 701.75*** | 724.58*** |
| SD | 7.43 | 0.16 | 1.29 | 0.156 | 0.012 | 105.91 | 112.50 |
| SMI0 (30 mg/kg) | | | | | | | |
| Mean | 68.10**$^{\#}$ | 0.38 | 11.93*** $^{\#\#\#}$ | 0.580$^{\#}$ | 0.037***$^{\#\#\#}$ | 1304.93***$^{\#\#}$ | 1476.49***$^{\#\#}$ |
| SD | 6.84 | 0.62 | 5.18 | 0.062 | 0.011 | 483.24 | 603.32 |
| SMI0 (150 mg/kg) | | | | | | | |
| Mean | 70.70* | 0.70 | 19.69***$^{\#\#\#\$\$\$}$ | 0.689*$^{\#\#\$}$ | 0.025***$^{\#\#\#\$}$ | 1749.59*** $^{\#\#\#\$}$ | 2066.53***$^{\#\#\#\$}$ |
| SD | 13.15 | 0.82 | 4.94 | 0.110 | 0.006 | 352.96 | 474.90 |

Notes:

In Table 2, mean represents an average value, and SD represents a standard deviation.

$C_{max}$ represents a peak concentration of a drug, which is the highest blood drug concentration after administration; and this parameter is an important index to reflect an absorption rate and an absorption degree of a drug in the body.

$T_{max}$ represents a time to peak (TTP), which is a time required to reach a peak concentration after administration; and this parameter reflects a speed at which a drug enters the body, and the higher the absorption rate, the shorter the peak time.

$V_d$ represents an apparent volume of distribution, which is a ratio constant of a drug amount in the body to a blood drug concentration when a drug reaches a dynamic equilibrium in the body and has a unit generally of L; and this parameter reflects a distribution range of a drug in the body, and the larger the value, the wider the distribution. The apparent volume of distribution is numerically obtained through a ratio of a clearance to a terminal elimination rate.

CL represents a clearance, which is an apparent volume of distribution of a drug cleared from the body per unit time and has a unit generally of L/h; and this parameter is an important parameter to reflect a treatment characteristic of the body for a drug and is closely related to physiological factors. A clearance is obtained based on a ratio of a dose to $AUC_{(0-\infty)}$.

AUC represents an area under the concentration-time curve, which is an area surrounded by a blood drug concentration curve and a time axis; and this parameter is an important index to evaluate an absorption degree of a drug, and reflects an exposure characteristic of a drug in the body. Since a blood drug concentration can only be observed until a specified time point t in pharmacokinetic studies, AUC has two representations: $AUC_{(0-t)}$ and $AUC_{(0-\infty)}$, where the former is obtained according to a trapezoidal area method and the latter is calculated according to the following equation: $AUC_{(0-\infty)} = AUC_{(0-t)}$ + terminal point concentration/terminal elimination rate.

Example 11 Inhibition of the Compound SMI0 on DEN-Induced Rat Liver Damage

Experimental method: An SD rat liver damage model was constructed through intermittent intraperitoneal injection of DEN. A model group was injected intraperitoneally with DEN at 50 mg/kg twice a week in the first 4 weeks and then once a week in the 5th to 8th weeks. SMI0 intervention groups, which were injected with DEN at the amount and the way the same as that in the model group, included SMI0+DEN low-dose and high-dose groups and an SMI0 high-dose continuous administration group, where the SMI0+DEN low-dose and high-dose groups were intragastrically administered with the compound SMI0 at 30 mg/kg and 150 mg/kg 5 min before DEN administration each time, respectively; and the SMI0 high-dose continuous administration group was intragastrically administered with the compound SMI0 at 150 mg/kg every day from the 1st week to the 8th week. At the end of molding, blood was collected from the orbit, and plasma liver function indexes of rats were determined by an automatic biochemical analyzer (model group, n=10 rats; SMI0 compound low-dose group, n=21 rats; (150 mg/kg)[a], SMI0 compound+DEN high-dose group, n=28 rats; and (150 mg/kg)[b], SMI0 compound high-dose continuous administration group, n=24 rats].

Experimental results: Compared with the model group, in the SMI0 intervention group, the albumin (ALB2) and cholinesterase (CHE2) levels were significantly increased, and the alkaline phosphatase (ALP) (ALP2S), alanine aminotransferase (ALTL), direct bilirubin (BILD2), total bilirubin (BILT3), and glutamyl transpeptidase (GGTI2) levels were significantly reduced; and the TP2 level was significantly increased in the SMI0 low-dose group, and the GGTI2 level was significantly reduced in the SMI0+DEN high-dose group and the SMI0 high-dose continuous administration group (as shown in FIGS. 13A-13I, *P<0.05, P<0.01, and *P<0.001 vs model group; and 150 mg/kg[a] was for the SMI0+DEN high-dose group, and 150 mg/kg[b] was for the SMI0 high-dose continuous administration group); compared with the SMI0 low-dose group, in the SMI0+DEN high-dose group, the ALTL, BILD2, BILT3, and GGTI2 levels were significantly reduced, and the TP2 level was significantly increased; and in the SMI0 high-dose continuous administration group, the ALB2 level was significantly increased, and the ALP2S, ALTL, ASTL, BILD2, CHE2, BILT3, and GGTI2 levels were significantly reduced ($^{##}$P<0.01, $^{###}$P<0.001 vs SMI0 low-dose group); and compared with the SMI0+DEN high-dose group, in the SMI0 high-dose continuous administration group, the ALB2 level was significantly increased, and the ALP2S, ALTL, ASTL, BILD2, CHE2, BILT3, and GGTI2 levels were significantly reduced ($^{\$}$P<0.05 and $^{\$\$\$}$P<0.001 vs SMI0+DEN high-dose group), indicating that the SMI0 administration can significantly improve the DEN-induced rat liver damage.

It can be seen from the above results that SMI0 has a significant prevention and treatment effect on the DEN-induced rat liver damage, indicating that the compound SMI0 can be used for the prevention and treatment of clinical liver damage.

Example 12 Inhibition of SMI0 on Liver Steatosis and Hepatitis in Mice Caused by a High-Fat Diet Experimental method: Healthy male C57/6J mice were fed with a high-fructose, high-fat, and high-cholesterol feed to prepare mouse liver steatosis and hepatitis models, and a control group was fed with a low-fat and low-sugar control feed. An SMI0 intervention group was divided into a low-dose intervention group and a high-dose intervention group, which were intragastrically administered with the compound SMI0 at 30 mg/kg and 150 mg/kg every day from the beginning of modeling to the 22nd week of modeling. At the end of the 22-week experiment, blood was collected from the orbit, a body weight was measured, and then the mice each were sacrificed. The weight and appearance of a liver (color, texture, and presence or absence of nodules of the liver) were recorded. Some liver specimens were subjected to HE staining and then observed, and a steatosis score of mice in each group was recorded; and Masson staining was conducted to evaluate a liver fibrosis status of mice, and an oil red O staining area percentage and an LCA staining inflammation score were determined (model group, n=8 mice; SMI0 compound low-dose group, n=10 rats; and SMI0 compound high-dose group, n=10 rats).

The pathological results of HE staining of a liver tissue were subjected to quantitative scoring based on the following criteria to determine a steatosis severity:

| | |
|---|---|
| (1) steatosis area less than 5% | 0 point |
| (2) steatosis area: 5% to 20% | 1 point |
| (3) steatosis area: 20% to 35% | 2 points |
| (4) steatosis area: 35% to 50% | 3 points |
| (5) steatosis area: 50% to 65% | 4 points |
| (6) steatosis area: 65% to 80% | 5 points |
| (7) steatosis area larger than 80% | 6 points. |

The pathological results of Masson staining of a liver tissue were subjected to quantitative scoring based on the following criteria to determine a fibrosis severity:

| | |
|---|---|
| (1) no fibrosis | 0 point |
| (2) in area 3, there is weak perisinusoidal fibrogenesis | 1 point |
| (3) in area 3, there is medium-intensity perisinusoidal fibrogenesis | 2 points |
| (4) there is obvious fibrogenesis in or around the portal vein | 3 points |
| (5) there is obvious fibrogenesis around the sinus and in or around the portal vein | 4 points |
| (6) fiber bridging formation | 5 points |
| (7) cirrhosis formation | 6 points |

Experimental results: Compared with the control group, in the model group, the liver coefficient, steatosis degree (steatosis score and oil red O staining area percentage), and liver inflammation level (number of LCA-positive cell staining foci) were significantly increased to varying degrees (as shown in FIGS. 14A-14B and FIGS. 15A-15E, *P<0.05, P<0.01, and *P<0.001 vs the control group; and scales in FIGS. 14A-14B each were 100 m); and compared with the model group, in the SMI0 low-dose intervention group, the liver coefficient and steatosis degree (steatosis score and oil red O staining area percentage) were significantly reduced ($^{#}$P<0.05, $^{##}$P<0.01, and $^{###}$P<0.001 vs the model group), and in the SMI0 high-dose intervention group, the steatosis degree (steatosis score and oil red O staining area percentage) and liver inflammation level (number of LCA-positive cell staining foci) were significantly reduced, indicating that the compound SMI0 can significantly reduce the liver steatosis and inflammation induced by a high-fat diet.

It can be seen from the above results that SMI0 has a significant prevention and treatment effect on the liver steatosis and hepatitis induced by a high-fat diet, indicating that the compound SMI0 can be used for the prevention and treatment of clinical fatty liver and hepatitis.

Example 13 Inhibition of SMI0 on the Occurrence and Development of Liver Fibrosis (1) Inhibition of SMI0 on Liver Fibrosis in Mice Induced by a High-Fat Diet Experimental method: Male C57/6J mice were fed with a high-fructose, high-fat, and high-cholesterol feed to prepare mouse liver steatosis and hepatitis models, and a control group was fed with a low-fat and low-sugar control feed. An SMI0 intervention group was divided into a low-dose intervention group and a high-dose intervention group, which were intragastrically administered with the compound SMI0 at 30 mg/kg and 150 mg/kg every day from the beginning of modeling to the 26nd week of modeling. At the end of the 26-week experiment, blood was collected from the orbit, a body weight was measured, and then the mice each were sacrificed. The weight and appearance of a liver (color, texture, and presence or absence of nodules of the liver) were recorded. Some liver specimens were subjected to HE staining and then observed, and a steatosis score of mice in each group was recorded; and Masson staining was conducted to evaluate a liver fibrosis status of mice, and an oil red O staining area percentage was determined (model group, n=10 mice; SMI0 compound low-dose group, n=10 rats; and SMI0 compound high-dose group, n=10 rats).

Experimental results: Compared with the control group, in the model group, the liver coefficient, index reflecting a steatosis degree (steatosis score and oil red O staining area percentage), and Masson staining score reflecting a fibrosis degree were significantly increased to varying degrees (as shown in FIGS. 16A-16B and FIGS. 17A-17D, *P<0.05 and P<0.01 vs the control group; and in FIG. 16**B, HE and Masson staining scales each were 100 m, and an oil red staining scale was 50 m); and compared with the model group, in the SMI0 low-dose and high-dose intervention groups, the steatosis degree (steatosis score and oil red O staining area percentage) and fibrosis degree (Masson staining score) ($^{\#}$P<0.05, $^{\#\#}$P<0.01, and $^{\#\#\#}$P<0.001 vs the model group), indicating that the compound SMI0 can significantly reduce a liver fibrosis level in mice induced by a high-fat diet.

It can be seen from the above results that SMI0 has a significant prevention and treatment effect on the liver fibrosis in mice induced by a high-fat diet, indicating that the compound SMI0 can be used for the prevention and treatment of clinical liver fibrosis.

(2) Inhibition of SMI0 on DEN-Induced Liver Fibrosis in Rats

Experimental method: An SD rat liver damage model was constructed through intermittent intraperitoneal injection of DEN. A model group was injected intraperitoneally with DEN at 50 mg/kg twice a week in the first 4 weeks and then once a week in the 5th to 12th weeks. SMI0 intervention groups, which were injected with DEN at the amount and the way the same as that in the model group, included SMI0+DEN low-dose and high-dose groups and an SMI0 high-dose continuous administration group, where the SMI0+DEN low-dose and high-dose groups were intragastrically administered with the compound SMI0 at 30 mg/kg and 150 mg/kg 5 min before DEN administration each time, respectively; and the SMI0 high-dose continuous administration group was intragastrically administered with the compound SMI0 at 150 mg/kg every day from the 1st week to the 12th week. At the end of molding, blood was collected from the orbit, and plasma liver function indexes of rats were determined by an automatic biochemical analyzer (model group, n=10 rats; SMI0 compound low-dose group, n=21 rats; SMI0 compound+DEN high-dose group, n=28 rats; and SMI0 compound high-dose continuous administration group, n=24 rats).

Experimental results: Compared with the model group, in the SMI0 intervention group, the liver coefficient, liver fibrosis Ishark score, liver fibrosis Masson staining area percentage, α-SMA, and Collagen I were reduced to varying degrees (as shown in FIGS. 18A-18B and FIGS. 19A-19E, *P<0.05, P<0.01, and *P<0.001 vs the model group; and scales in FIG. 18B each were 100 μm); and the SMI0 high-dose (150 mg/kg$^{b}$) continuous administration group exhibited a significantly better effect than the SMI0+DEN high-dose group (150 mg/kg$^{a}$) and the SMI0 low-dose group ($^{\#\#}$P<0.01 and $^{\#\#\#}$P<0.001 vs the SMI0 low-dose group; and $^{\&}$P<0.05 and $^{\&\&\&}$P<0.001 vs the SMI0+DEN high-dose group).

It can be seen from the above results that SMI0 has a significant prevention and treatment effect on the DEN-induced rat liver fibrosis, indicating that the compound SMI0 can be used for the prevention and treatment of clinical liver fibrosis.

Example 14 Inhibition of SMI0 on the Occurrence and Development of Pulmonary Fibrosis in Mice (1) Inhibition of CYP2E1 Gene Knockout on Pulmonary Fibrosis in Mice Experimental method: A C57BL/6N mouse pulmonary fibrosis model was established through intratracheal instillation with 8 mg/kg LPS. C57BL/6N mice were divided into a control group, a model group, and a CYP2E1 gene-knockout group, and the modeling took 28 days (control group, n=8; model group, n=8; and gene knockout group, n=8). At the end of the experiment, a body weight of mice in each group was recorded, blood was collected from the orbit, the mice were sacrificed, and lung tissues were collected and weighed. The left lungs were fixed in 4% formalin and subjected to HE and Masson staining, and the lung tissues were subjected to fibrosis grading and fibrosis and histological scoring to reflect a severity of pulmonary fibrosis.

Experimental results: Compared with the control group, in the model group, the lung index of mice was significantly increased, the alveolar septum was pathologically thickened, the alveolar chamber shrank or even disappeared, the lung parenchyma underwent obvious inflammatory cell infiltration, and the fibrosis score and histological score were significantly increased; and compared with the model group, in the CYP2E1 gene-knockout group, the lung index of mice was significantly reduced, there was no obvious pathological inflammatory cell infiltration, and the fibrosis score and histological score were significantly reduced (as shown in FIGS. 20A-20B), indicating that the CYP2E1 gene knockout can significantly inhibit the occurrence of LPS-induced pulmonary fibrosis.

(2) Intervention of SMI0 in Lung Injury in Mice

Experimental method: A C57BL/6N mouse pulmonary fibrosis model was established through intratracheal instillation with 8 mg/kg LPS. An SMI0 intervention group was divided into a low-dose group and a high-dose group, which were intragastrically administered with the compound SMI0 respectively at 30 mg/kg and 90 mg/kg every day from three days before modeling until 6 h before the end of the modeling (control group, n=8; model group, n=8; and SMI0 compound high-dose group, n=8). At the end of the experiment, a body weight of mice in each group was recorded, blood was collected from the orbit, the mice were sacrificed, and lung tissues were collected and weighed. The left lungs were fixed in 4% formalin and subjected to HE staining.

Experimental results: Compared with the control group, in the model group, the lung index of mice was significantly increased (P<0.001); and compared with the model group, in both the SMI0 low-dose and high-dose groups, the lung index of mice was significantly reduced (P<0.01), indicating that SMI0 can significantly reduce the increase of lung index in mice with LPS-induced acute lung injury (ALI). Similarly, compared with the control group, in the model group, the lung tissue structure of mice was obviously damaged, which was mainly manifested as alveolar edema, alveolar wall thickening, alveolar chamber shrinkage, and infiltration of a large number of inflammatory cells, and the lung injury score was significantly increased; and compared with the model group, in the SMI0 administration group, there was alleviated pulmonary edema, narrowed alveolar septum, reduced inflammatory cell infiltration, and normalized lung tissue results, and the lung injury score was significant reduced (as shown in FIGS. 21A-21B), indicating that SMI0 can mitigate the LPS-induced ALI in mice.

(3) Intervention of SMI0 in Pulmonary Fibrosis in Mice

Experimental method: A C57BL/6N mouse pulmonary fibrosis model was established through intratracheal instillation with 8 mg/kg LPS. An SMI0 intervention group was divided into a low-dose group and a high-dose group, which were intragastrically administered with the compound SMI0 respectively at 30 mg/kg and 90 mg/kg every day from three days before modeling to the end of the 28-d modeling (control group, n=8; model group, n=8; and SMI0 compound high-dose group, n=8). At the end of the experiment, a body weight of mice in each group was recorded, blood was collected from the orbit, the mice were sacrificed, and lung tissues were collected and weighed. The left lungs were fixed in 4% formalin and subjected to HE and Masson staining, and the lung tissues were subjected to fibrosis grading and fibrosis and histological scoring to reflect a severity of pulmonary fibrosis.

Experimental results: Compared with the control group, in the model group, the lung index of mice was significantly increased, the alveolar septum was pathologically thickened, the alveolar chamber shrank or even disappeared, and the lung parenchyma underwent obvious inflammatory cell infiltration; and compared with the model group, in the SMI0 intervention group, the lung index of mice was significantly reduced, and there was no obvious pathological inflammatory cell infiltration (as shown in FIGS. 22A-22B), indicating that the administration of SMI0 can significantly inhibit the occurrence of LPS-induced pulmonary fibrosis.

It can be seen from the above results that the CYP2E1 inhibitor SMI0 has a significant prevention and treatment effect on the occurrence and development of pulmonary fibrosis induced by intratracheal instillation of LPS, indicating that SMI0 can be used for the prevention and treatment of clinical pulmonary fibrosis.

(4) Correlation Between CYP2E1 Activity and Pulmonary Fibrosis Severity in Mice after SMI0 Inhibition Experimental method: A calcium precipitation method was used to prepare a mouse liver microsome, and a Braford method was used to determine a protein concentration in the microsome. An incubation system was prepared with 2×PBS, a CZX solution, and the liver microsome at a final concentration of 0.5 mg/mL, and then pre-incubated at 37° C. for 5 min; NADPH was added to initiate a reaction, and a resulting mixture was incubated at 37° C. for 30 min and then placed on ice to terminate the reaction; and ethyl acetate was added to extract 6-hydroxychlorzoxazone, a resulting mixture was vortexed and centrifuged, and a resulting upper organic phase was collected and blow-dried with nitrogen. A peak area of a CZX metabolite 6-hydroxychlorzoxazone was detected by HPLC under the following conditions: methanol:water=56:44, and detection wavelength: 287 nm. A concentration A C of the metabolite 6-hydroxychlorzoxazone was calculated through substitution into a standard curve; and a reaction rate of conversion of CZX into 6-hydroxychlorzoxazone was calculated according to V(pmol/min/mg)=(AC*1000)/(B*T) to evaluate an enzymatic activity of CYP2E1, where B represents a protein concentration of the microsome (mg/mL) and T represents an incubation time (min). A correlation between a CYP2E1 activity and a pulmonary fibrosis severity in mice was analyzed.

Experimental results: Compared with the control group, a reaction rate V of CZX metabolism in mice of the model group was significantly increased (P<0.01); and compared with the model group, a reaction rate V of CZX metabolism in the SMI0 high-dose group was significantly reduced (P<0.05), indicating that SMI0 can effectively inhibit the increase in enzymatic activity of CYP2E1 in the LPS-induced mouse pulmonary fibrosis model. A correlation between the reaction rate V of CZX and the lung index of pulmonary fibrosis was analyzed, and a correlation coefficient r of the two was 0.81, P<0.01 (as shown in FIGS. 23A-23B), indicating that the enzymatic activity of CYP2E1 has prominent correlation with the pulmonary fibrosis severity, and an antifibrosis effect of SMI0 may be related to the inhibition on enzymatic activity of CYP2E1.

(5) Inhibition of SMI0 on an Inflammatory Microenvironment of Pulmonary Fibrosis in Mice A. Inhibition of SMI0 on an Inflammatory Response in Lung Injury Mice Experimental method: A neutrophil level in a mouse lung tissue was evaluated through immunohistochemistry (IHC) staining, and an immunostaining-positive area percentage was quantitatively evaluated by Image-Pro Plus software. RNA of a mouse lung tissue was extracted by a kit method, and expression levels of TNF-α and IL-1β in lung tissues of mice were determined by RT-PCR.

Figure 24A:
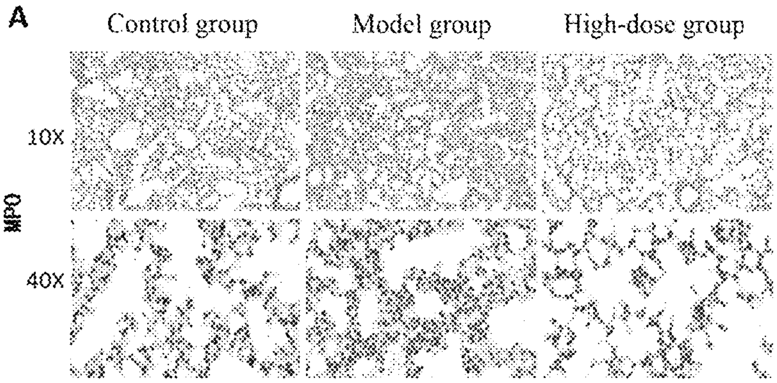
FIGS. 24A-24B show inhibitory effects of the compound SMI0 on myeloperoxidase (MPO) levels in lung tissues in LPS-induced mouse pulmonary fibrosis models, where
Figure 24B:
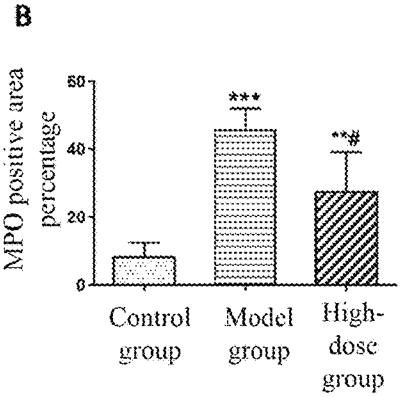
Figure 25A:
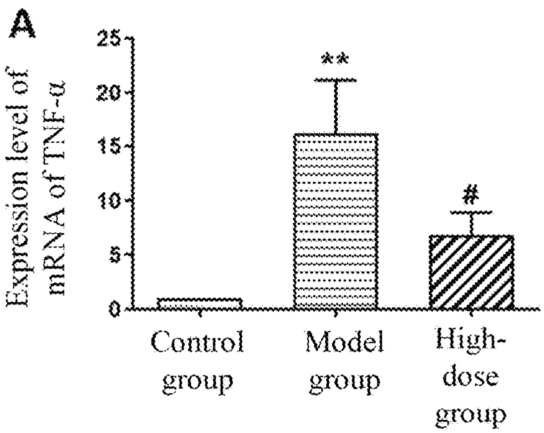
FIGS. 25A-25B show inhibitory effects of the compound SMI0 on inflammatory factors in lung tissues of LPS-induced mouse pulmonary fibrosis models, where
Figure 25B:
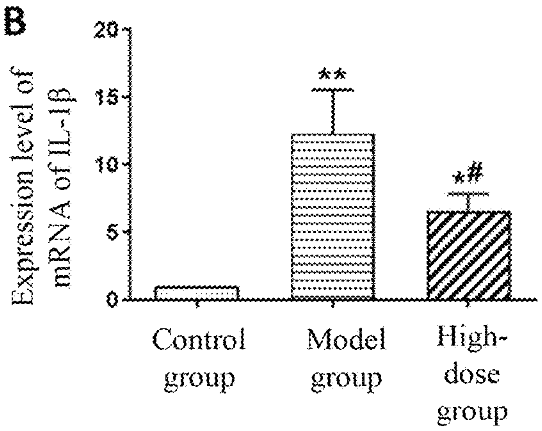
Figure 26A:
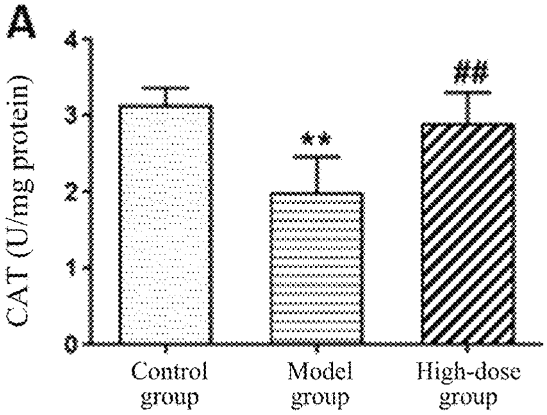
FIGS. 26A-26F show inhibitory effects of the compound SMI0 on the oxidative stress and the expression of epithelial cell marker E-cadherin and apoptosis-associated proteins in lung tissues of LPS-induced mouse pulmonary fibrosis models, where
Figure 26B:
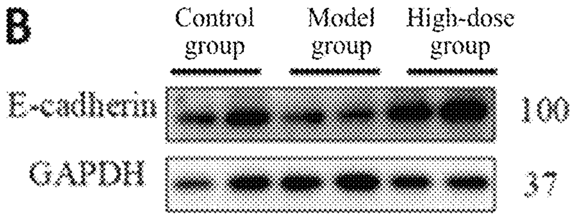
Figure 26C:
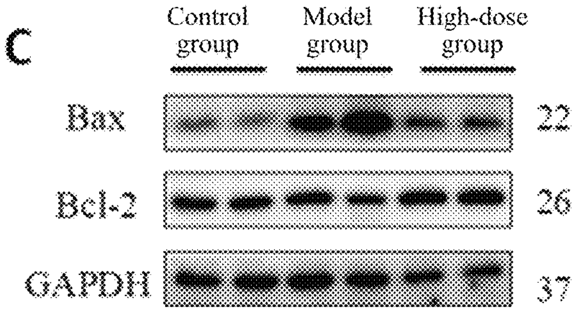
Figure 26D:
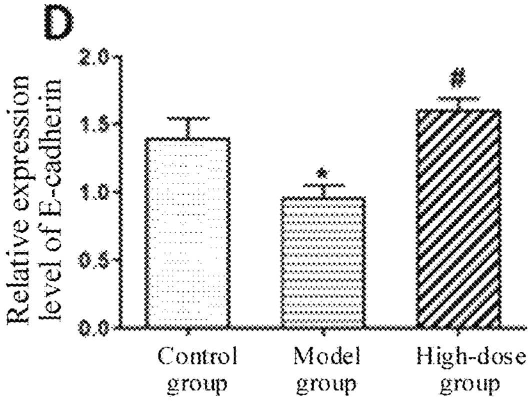
Figure 26E:
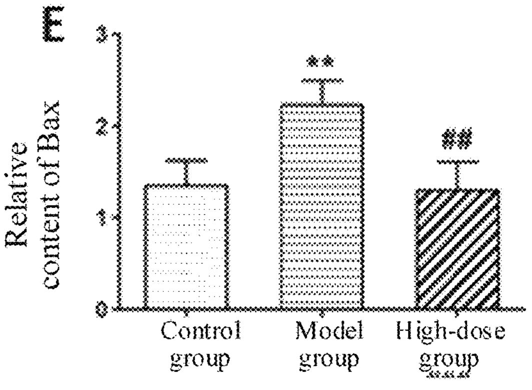
Figure 26F:
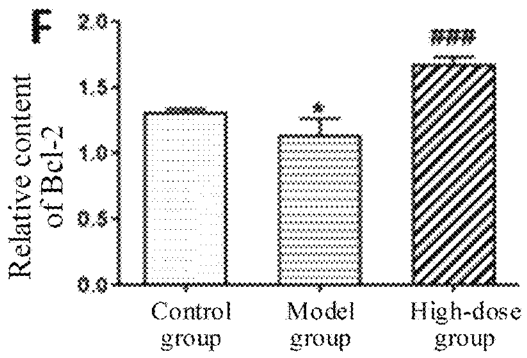
Figure 27A:
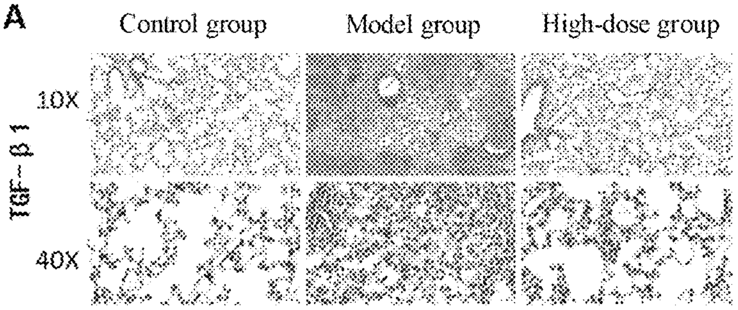
FIGS. 27A-27D show inhibitory effects of the compound SMI0 on the expression of TGF-β1 and α-SMA in lung tissues of LPS-induced mouse pulmonary fibrosis models, where
Figure 27B:
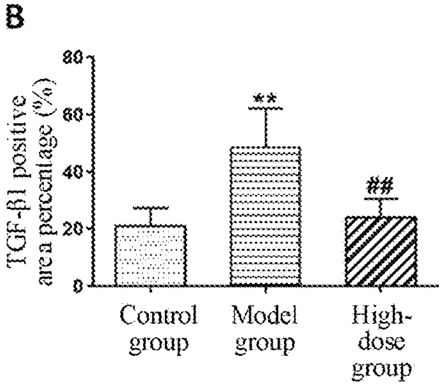
Figure 27C:
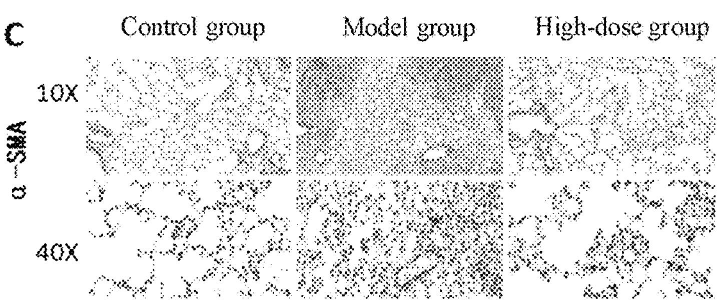
Figure 27D:
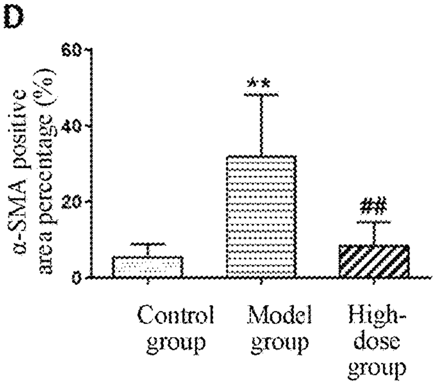

Experimental results: Compared with the control group, in the model group, the MPO immunostaining-positive area percentage in the lung tissue was significantly increased (P<0.001) (as shown in FIGS. 24A-24B), and expression levels of TNF-α and IL-1β in the lung tissue were significantly increased (P<0.01) (as shown in FIGS. 25A-25B); and compared with the model group, in the SMI0 high-dose group, the MPO immunostaining-positive area percentage was significantly reduced (P<0.05), and expression levels of TNF-α and IL-1β in the lung tissue were significantly reduced (P<0.05), indicating that SMI0 can alleviate the neutrophil infiltration and inhibit the release of proinflammatory cytokines in the lung tissue of mice with LPS-induced ALI.

B. Inhibition of SMI0 on an Inflammatory Microenvironment in Pulmonary Fibrosis Mice Experimental method: An ammonium molybdate method and a microplate method were used to treat a mouse lung tissue homogenate, and changes of oxidative stress indexes CAT and GSH in the lung tissue of mice in each group were detected. Expression levels of TGF-01 and α-SMA in the mouse lung tissue were evaluated through immunohistochemical staining, and a positive area percentage was counted by Image-Pro Plus software. Expression levels of the epithelial cell marker E-cadherin, the apoptosis-associated protein Bax, and the anti-apoptotic protein Bcl-2 were detected by WB.

Experimental results: Compared with the control group, in the model group, the oxidative stress index CAT (P<0.01) and epithelial cell marker E-cadherin (P<0.05) levels were significantly reduced, the immunostaining-positive area percentages of α-SMA and TGF-β1 were significantly increased (P<0.01), the expression level of the apoptotic factor Bax was significantly increased (P<0.01), and the expression level of the anti-apoptotic factor Bcl-2 was significantly reduced (P<0.05); and compared with the model group, in the SMI0 intervention group, the oxidative stress index CAT (P<0.01) and epithelial cell marker E-cadherin (P<0.05) levels were significantly increased, the immunostaining-positive area percentages of α-SMA and TGF-β1 were significantly reduced (P<0.01), the Bax level was significantly reduced (P<0.01), and the Bcl-2 level was significantly increased (P<0.001) (as shown in FIGS. 26A-26F to FIGS. 27A-27D), indicating that the alleviation of LPS-induced pulmonary fibrosis in mice by SMI0 may be related to the improvement of oxidation resistance, the anti-apoptotic effect, and the reduction in fibrosis-inducing factor TGF-01 level and epithelial mesenchymal cell transformation in the lung tissue of pulmonary fibrosis mice.

Example 15 Inhibition of SMI0 on the Lung Cancer Proliferation in Mice (1) CYP2E1 Changes in Clinical Lung Cancer Patients Experimental method: The changes of CYP2E1 expression in paracancerous tissues of 30 clinical lung cancer patients were investigated with lung tissues of 30 healthy individuals as a control, and the changes of CYP2E1 contents in the paracancerous tissues of the lung cancer patients were determined.

Figure 28:
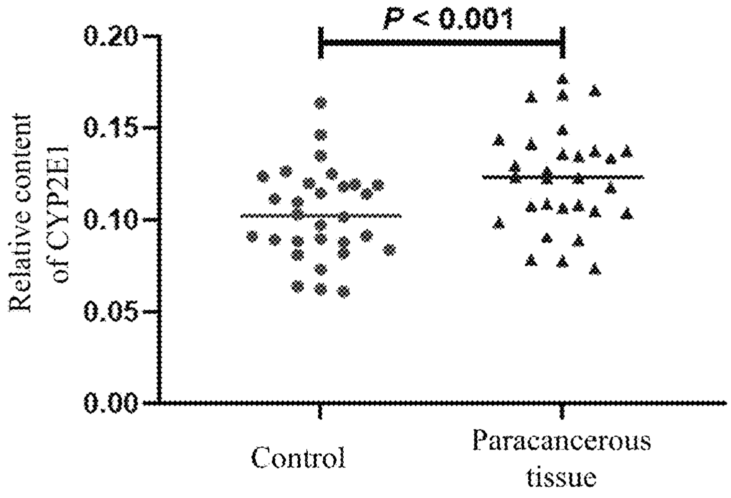
FIG. 28 shows a high expression level of CYP2E1 in a paracancerous tissue of lung cancer.

Experimental results: Immunohistochemical results showed that the expression of CYP2E1 in the paratumoral tissues of the lung cancer patients was significantly higher than that in the healthy lung tissue (as shown in FIG. 28, ***$P<0.001$ vs the healthy lung tissue group).

(2) Changes of In Situ Transplanted Tumors in Lungs of CYP2E1 Gene-Knockout Mice Experimental method: A female C57 mouse lung cancer model with an in situ transplanted tumor was prepared with a lung cancer cell line Lewis at a cell amount of $2*10^4$. C57BL/6N mice were divided into a control group, a model group, and a CYP2E1 gene-knockout group, and the modeling took 18 days (control group, n=8; model group, n=8; and gene knockout group, n=8). At the end of the experiment, a body weight of mice in each group was recorded, blood was collected from the orbit, the mice were sacrificed, and lung tissues and tumor tissues were collected and weighed. Some lung specimens were subjected to HE staining, and then the lung lesion and tumorigenesis of mice in each group were observed.

Figure 29A:
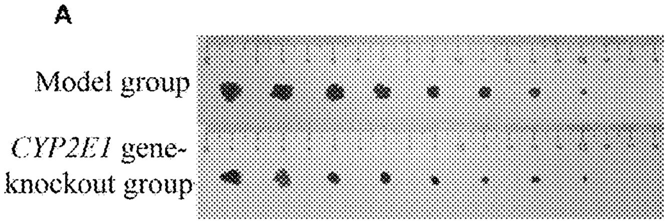
FIGS. 29A-29B show inhibitory effects of CYP2E1 gene knockout on mouse lung cancer models constructed through in situ implantation of lung cancer Lewis cells into lungs of mice, where
Figure 29B:
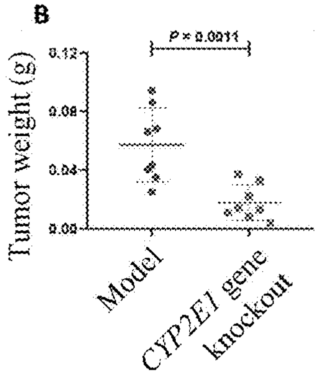

Experimental results: Compared with the model group, a weight of lung cancer in CYP2E1 gene-knockout mice was significantly reduced (as shown in FIGS. 29A-29B), indicating that the CYP2E1 knockout can significantly inhibit the occurrence and development of lung cancer in the Lewis lung cancer model with the in situ transplanted tumor.

(3) Intervention of SMI0 in an In Situ Transplanted Lewis Cell Tumor in Lungs of Mice Experimental method: A female C57 mouse lung cancer model with an in situ transplanted tumor was prepared with a lung cancer cell line Lewis at a cell amount of $2*10^4$. C57BL/6N mice were divided into a control group, a model group, a positive drug group, and an SMI0 intervention group, and the modeling took 18 days (control group, n=20; model group, n=20; positive drug group (20 mg/kg), n=15; SMI0 (3.3 mg/kg), n=15; SMI0 (10 mg/kg), n=20; and SMI0 (30 mg/kg), n=20). At the end of the experiment, a body weight of mice in each group was recorded, blood was collected from the orbit, the mice were sacrificed, and lung tissues and tumor tissues were collected and weighed. The weight and appearance of the lung (color, texture, or the like of the lung) were recorded. All tumors of an animal were cumulatively arranged together to indicate the tumorigenesis of the animal, and a cumulative weight of lung tumors in each animal was determined. Some lung specimens were subjected to HE staining, and then the lung lesion and tumorigenesis of mice in each group were observed.

Figure 30A:
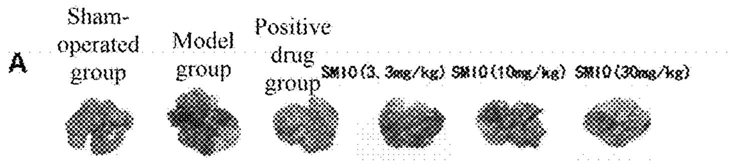
FIGS. 30A-30C show inhibitory effects of the compound SMI0 on mouse lung cancer models constructed through in situ implantation of lung cancer Lewis cells into lungs of mice, where
Figure 30B:
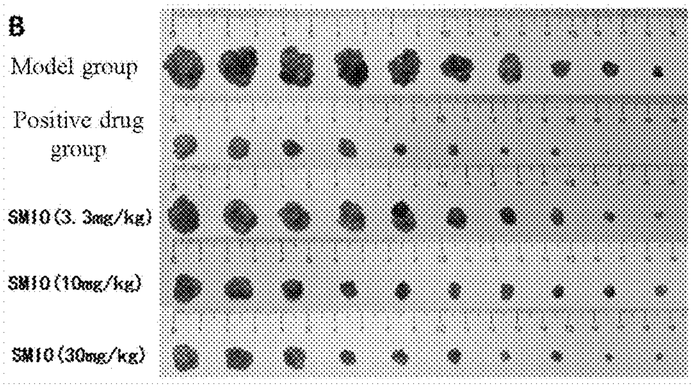
Figure 30C:
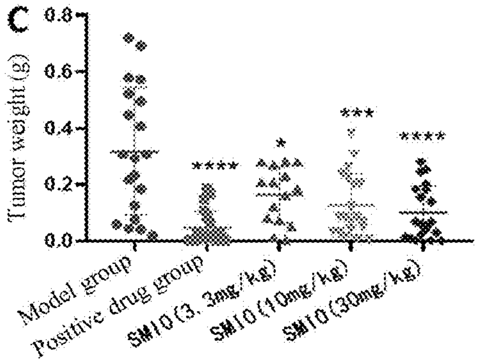

Experimental results: Compared with the model group, the proliferation of lung tumors in mice of the SMI0 intervention group was significantly inhibited, that is, the SMI0 intervention could significantly inhibit the growth of lung tumors in mice, with a tumor proliferation inhibition rate as high as 68.3% (as shown in FIGS. 30A-30C, *$P<0.05$ vs the model group, where FIG. 30A shows a representative picture of a tumor-bearing lung tissue of each mouse in each group; FIG. 30B shows a lung tumor tissue of each mouse; and FIG. 30C shows a tumor weight in each group), indicating that the SMI0 administration can significantly inhibit the occurrence and development of lung cancer in the mouse Lewis lung cancer model with the in situ transplanted tumor.

(4) Intervention of SMI0 in a Mouse CT26 Cell Lung Metastasis

Experimental method: A female Balb/C mouse lung metastasis model was constructed through tail vein injection of a CRC cell CT26, with a cell amount of $3*10^5$. Mice were divided into a control group, a model group, and an SMI0 intervention group, and the modeling took 14 days (control group, n=5; model group, n=5; and SMI0 (30 mg/kg), n=5). At the end of the experiment, a body weight of mice in each group was recorded, blood was collected from the orbit, the mice were sacrificed, and lung tissues were collected and weighed. The lung tissues were fixed in a *Brucella* staining solution for 24 h, and a number of lung nodules of mice in each group was recorded.

Experimental results: Compared with the model group, in the SMI0 intervention group, the lung weight of mice was significantly reduced, the number of nodules was significantly reduced, and the tumor proliferation inhibition rate was as high as 66.7% (as shown in FIGS. 31A-31B, *$P<0.05$ vs the model group, where FIG. 31A shows a representative picture of a tumor-bearing lung tissue of mice in each group and FIG. 31B shows the lung weight and the number of lung nodules of each mouse), indicating that the SMI0 administration can significantly inhibit the occurrence and development of the lung metastasis in the lung metastasis model constructed through tail veil injection of the cell CT26.

(5) Intervention of SMI0 in a Mouse B16-F10 Cell Lung Metastasis

Experimental method: A female C57BL/6 mouse lung metastasis model was constructed through tail vein injection of a melanoma cell B16-F10, with a cell amount of $8*10^5$. Mice were divided into a control group, a model group, and an SMI0 intervention group, and the modeling took 14 days (control group, n=5; model group, n=5; and SMI0 (30 mg/kg), n=4). At the end of the experiment, a body weight of mice in each group was recorded, blood was collected from the orbit, the mice were sacrificed, and lung tissues were collected and weighed. The lung tissues were fixed in a formalin solution for 24 h, and a number of lung nodules of mice in each group was recorded.

Experimental results: Compared with the model group, in the SMI0 intervention group, the lung weight of mice was significantly reduced, the number of nodules was significantly reduced, and the tumor proliferation inhibition rate was as high as 58.3% (as shown in FIGS. 32A-32B, *$P<0.05$ vs the model group, where FIG. 32A shows a representative picture of a tumor-bearing lung tissue of mice in each group and FIG. 32B shows the lung weight of each mouse), indicating that the SMI0 administration can significantly inhibit the occurrence and development of the lung metastasis in the mouse lung metastasis model constructed through tail veil injection of the cell B16-F10.

It can be seen from the above results that the CYP2E1 inhibitor SMI0 has a significant prevention and treatment effect on the occurrence and development of the Lewis cell lung in situ transplanted tumor and the lung metastases constructed through tail veil injection of CT26 and B16-F10, indicating that the compound SMI0 can be used for the prevention and treatment of lung cancer.

(6) Correlation Between CYP2E1 Activity and Tumor Severity in a Lung Cancer In Situ Model after SMI0 Inhibition Experimental method: A calcium precipitation method was used to prepare a mouse liver microsome, and a Braford method was used to determine a protein concentration in the microsome. An incubation system was prepared with 2×PBS, a CZX solution, and the liver microsome at a final concentration of 0.5 mg/mL, and then pre-incubated at 37° C. for 5 min; NADPH was added to initiate a reaction, and a resulting mixture was incubated at 37° C. for 30 min and then placed on ice to terminate the reaction; and ethyl acetate was added to extract 6-hydroxychlorzoxazone, a resulting mixture was vortexed and centrifuged, and a resulting upper organic phase was collected and blow-dried with nitrogen. A peak area of a CZX metabolite 6-hydroxychlorzoxazone was detected by HPLC under the following conditions: methanol:water=56:44, and detection wavelength: 287 nm. A concentration A C of the metabolite 6-hydroxychlorzoxazone was calculated through substitution into a standard curve; and a reaction rate of conversion of CZX into 6-hydroxychlorzoxazone was calculated according to V(pmol/min/mg)=(AC*1000)/(B*T) to evaluate an enzymatic activity of CYP2E1, where B represents a protein concentration of the microsome (mg/mL) and T represents an incubation time (min). A correlation between CYP2E1 activity and lung tumor weight in the Lewis lung cancer in situ model was analyzed.

Figure 33A:
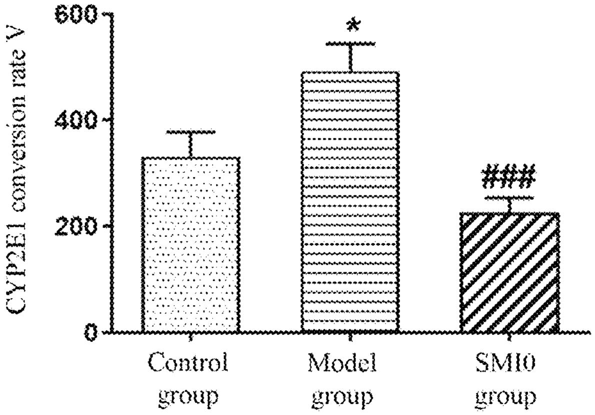
FIGS. 33A-33B show a change of CYP2E1 activity and a correlation between CYP2E1 activity and tumor severity in mouse lung cancer models constructed through in situ implantation of lung cancer Lewis cells into lungs of mice, where the FIG. 33A shows a change of CYP2E1 activity in mice of each group; and the FIG. 33B shows a correlation between CYP2E1 activity and lung tumor weight in mice.
Figure 33B:
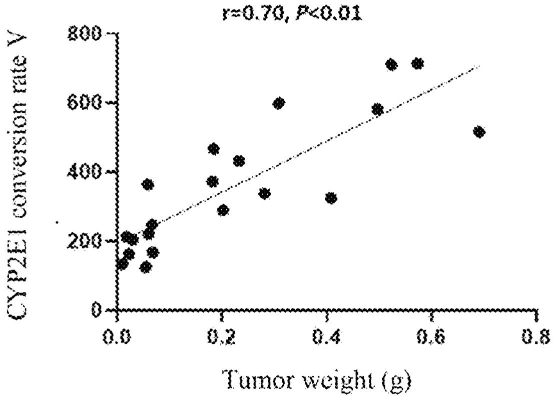

Experimental results: Compared with the sham-operated group, the CYP2E1 activity in the model group was significantly increased ($P<0.05$); and compared with the model group, the CYP2E1 activity in the SMI0 intervention group was significantly reduced ($P<0.05$), indicating that SMI0 can effectively inhibit the increase in enzymatic activity of CYP2E1 in the liver tissue of the mouse Lewis lung cancer in situ model, and the CYP2E1 activity of mice is significantly positively correlated with the tumor weight of the mouse Lewis lung cancer in situ model ($r=0.70$, $P<0.01$) (as shown in FIGS. 33A-33B), indicating that the enzymatic activity of CYP2E1 is positively correlated with the severity of Lewis lung cancer in situ, and the anti-lung cancer effect of SMI0 may be related to the inhibition on enzymatic activity of CYP2E1.

(7) Inhibition of SMI0 on an Inflammatory Microenvironment of a Mouse Lung In Situ Transplanted Tumor Experimental method: A WB method was used to detect the expression of proinflammatory cytokines TGF-β, IL-10, and IL-4, inflammation-associated signaling pathway proteins IL-6/p-STAT3 and p-ERK1/2/ERK1/2, and epithelial-mesenchymal transition (EMT)-associated proteins MMP-2 and MMP-9 in the mouse paracancerous lung tissue of each group and detect the expression of anti-apoptosis-associated proteins caspase3 and Bcl-2 and an autophagy-associated protein p53 in the tumor tissue.

Figure 34A:
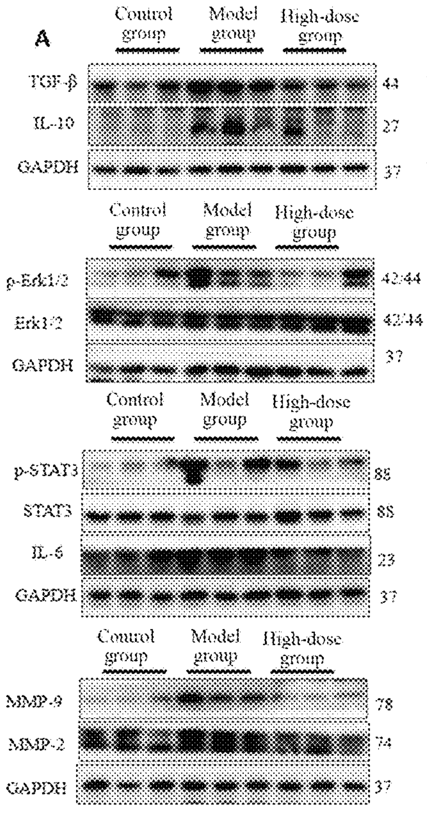
FIGS. 34A-34B show the inhibition of the compound SMI0 on an inflammatory microenvironment in a paracancerous lung tissue of a tumor model constructed through in situ transplantation of Lewis cells into lungs, where
Figure 34B:
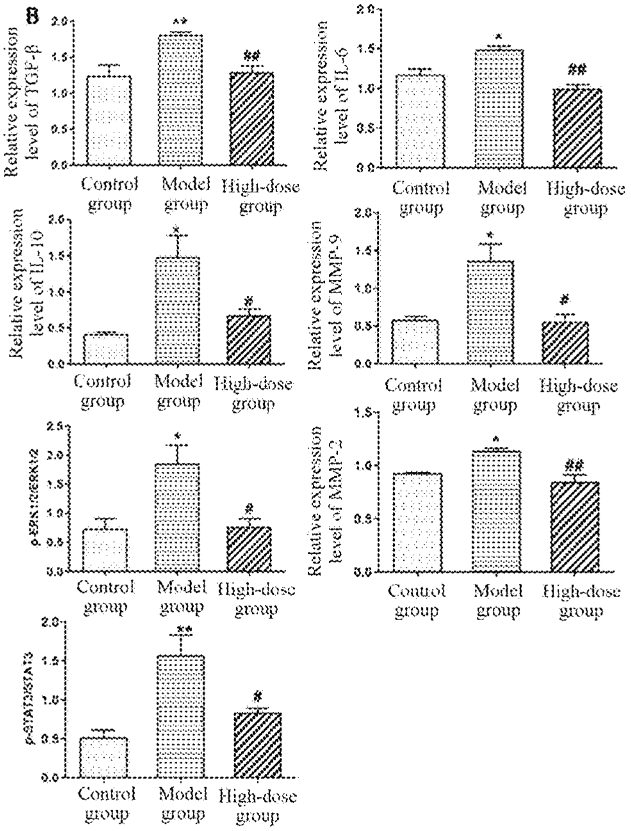
Figure 35A:
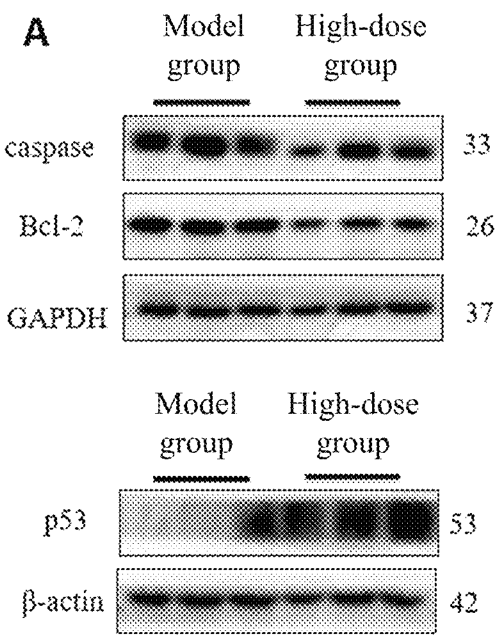
FIGS. 35A-35B show effects of the compound SMI0 on apoptosis and autophagy-associated proteins in a cancer tissue of a tumor model constructed through in situ transplantation of Lewis cells into lungs, where
Figure 35B:
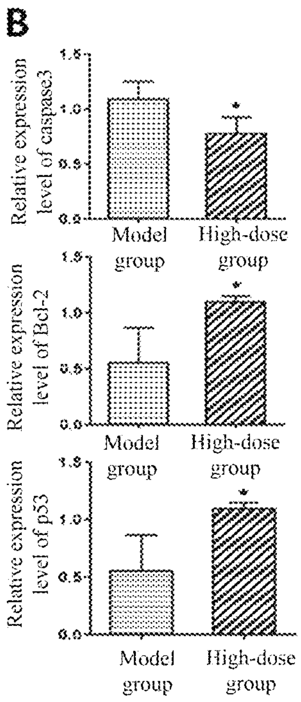

Experimental results: Compared with the sham-operated group, the expression of proinflammatory cytokines (TGF-β and IL-10), inflammation-associated signaling pathway proteins (IL-6/p-STAT3 and p-ERK1/2/ERK1/2), and matrix metalloproteinase (MMP) (MMP-2 and MMP-9) was significantly increased in the paratumoral tissue of the model group ($P<0.05$); further, compared with the model group, the expression of the above proteins was significantly reduced in the SMI0 intervention group ($P<0.05$) (as shown in FIGS. 34A-34B); and similarly, compared with the model group, in the SMI0 (30 mg/kg) intervention group, the expression of anti-apoptotic proteins caspase3 and Bcl-2 in the tumor tissue was significantly reduced ($P<0.05$), and the expression of the autophagy-associated protein p53 was significantly increased ($P<0.01$) (as shown in FIGS. 35A-35B), indicating that SMI0 can significantly inhibit the activation of inflammation and related signaling pathways and the expression of MMPs in the paratumoral lung tissue of the Lewis lung in situ transplanted tumor model and enhance the p53-mediated autophagy in the tumor tissue.

(8) Inhibition of SMI0 on M2 Polarization of Macrophages in a Paratumoral Microenvironment A. SMI0 Exhibited No Direct Inhibitory Effect on Lung Cancer Cells.

Experimental method: Lewis lung cancer cells and A549 lung cancer cells in a logarithmic growth phase each were selected and inoculated into a 96-well plate at a concentration of $1*10^5$ cells/mL, then 100 μL of a basic medium including SMI0 at different concentrations (0 μmol/L, 0.16 μmol/L, 0.8 μmol/L, 4 μmol/L, 20 μmol/L, and 100 μmol/L) was added to each well, and 24 h later, 10 μL of a CCK8 reagent was added to each well; and the cells were further cultivated for 2 h, and an absorbance OD value of each well was determined at 450 nm by a microplate reader. 3 replicates were set for each well, and an average was taken. The proliferation activity was calculated based on the OD value.

Figure 36A:
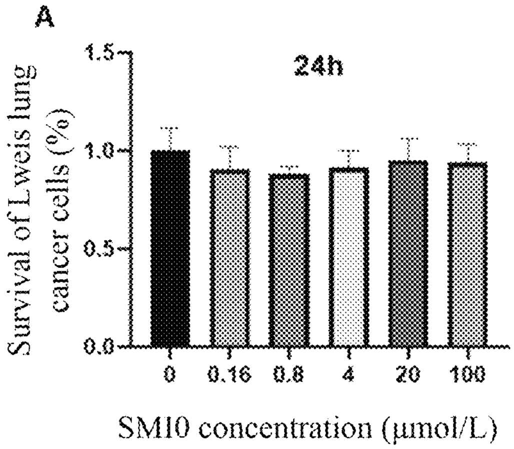
FIGS. 36A-36B show that the compound SMI0 has no direct inhibitory effect on lung cancer cells, where
Figure 36B:
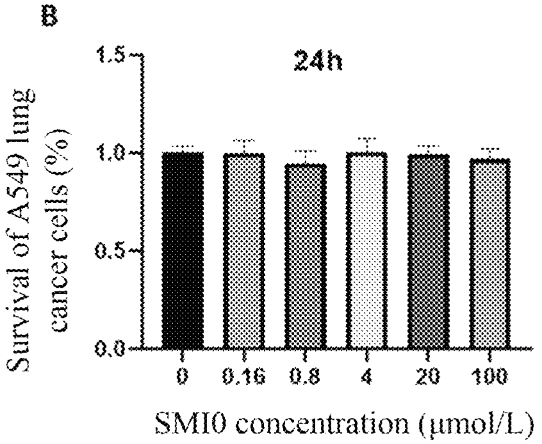

Experimental results: SMI0 at a test concentration (up to 100 μmol/L) exhibited no significant inhibitory effect on the proliferation of Lewis lung cancer cells and A549 lung cancer cells (as shown in FIGS. 36A-36B).

B. SMI0 Inhibited the Proliferation of Lung Cancer Cells by Inhibiting the M2 Polarization of Macrophages.

Experimental method: PMA was used at 100 μmol/L to induce the transformation of human monocytic leukemia cells THP-1 into MO macrophages, and then IL-4 and IL-13 were used at 20 ng/mL to induce the transformation of MO macrophages into M2 macrophages. A supernatant was collected to establish a co-cultivation system with an A549 lung cancer cell, thereby simulating a M2-type macrophage microenvironment of lung cancer. In the SMI0 intervention group, SMI0 (50 μmol/L) was added for intervention while interleukin was added for induction. Culture supernatants of the MO macrophages, M2 macrophages, and SMI0 intervention group were collected to prepare conditional media. Lewis lung cancer cells in a logarithmic growth phase were selected and inoculated into a 96-well plate at a concentration of $1*10^5$ cells/mL, then 100 μL of each of different conditional media was added to each well, and 24 h later, 10 μL of a CCK8 reagent was added to each well; and the cells were further cultivated for 2 h, and an absorbance OD value of each well was determined at 450 nm by a microplate reader. 3 replicates were set for each well, and an average was taken. The proliferation activity was calculated based on the OD value.

Figure 37:
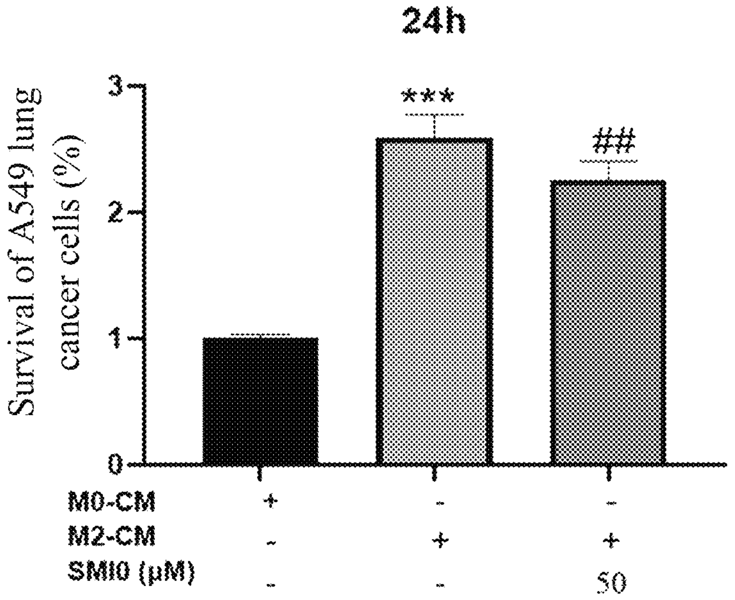
FIG. 37 shows that the compound SMI0 inhibits the proliferation of A549 lung cancer cells by inhibiting the M2 polarization of macrophages.

Experimental results: Compared with the group in which A549 lung cancer cells were cultivated alone, the proliferation activity of A549 cells in the M2 macrophage co-cultivation group was significantly enhanced ($P<0.01$); and compared with the M2 macrophage co-cultivation group, the proliferation activity of A549 cells in the SMI0 intervention group (50 mol/L) was significantly weakened ($P<0.05$) (as shown in FIG. 37), indicating that the inhibition of the CYP2E1 inhibitor SMI0 on the Lewis lung in situ transplanted tumor may be related to the inhibition on the paratumoral inflammatory microenvironment of lung cancer, especially to the M2 polarization of macrophages in the paratumoral microenvironment.

Example 16 Inhibition of SMI0 on the Occurrence and Development of Liver Cancer in Mice (1) CYP2E1 Changes in Clinical Liver Cancer Patients Experimental method: The changes of CYP2E1 expression in paracancerous tissues of 35 clinical liver cancer patients were investigated with liver tissues of 35 healthy individuals as a control, and the changes of CYP2E1 contents in the paracancerous tissues of the liver cancer patients were determined.

Figure 38:
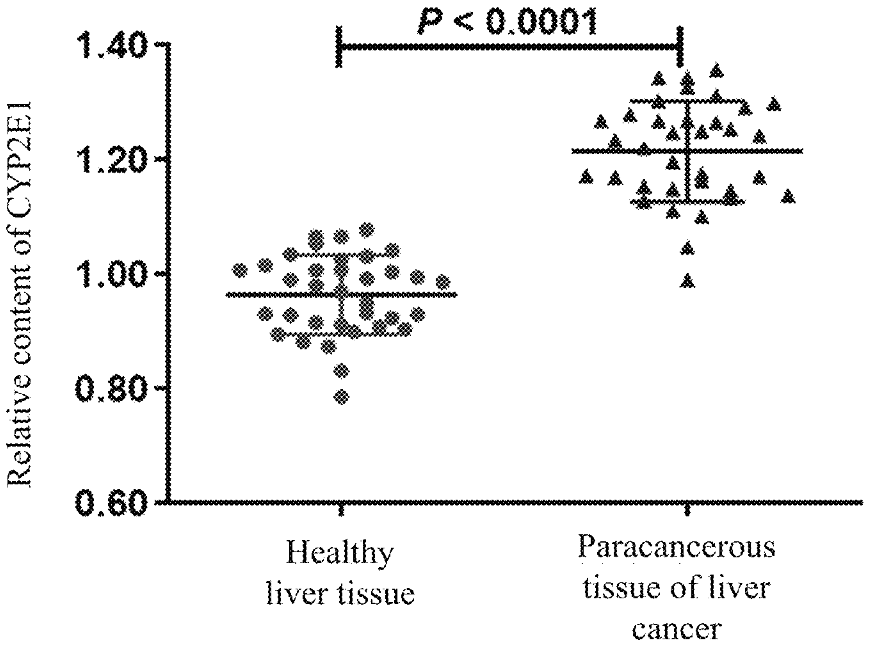
FIG. 38 shows the increased CYP2E1 contents in paracancerous liver tissues of liver cancer patients.

Experimental results: Immunohistochemical results showed that the expression of CYP2E1 in the paratumoral tissues of the liver cancer patients was significantly higher than that in the healthy liver tissue (as shown in FIG. 38, ***P<0.0001 vs the healthy liver tissue group).

(2) Inhibition of CYP2E1 Gene Knockout on a Rat Liver In Situ Transplanted Tumor Experimental method: An SD rat liver in situ transplanted tumor model was constructed through in situ implantation of a breast sarcoma cell line Walker256 into the liver, with a cell concentration of $4*10^6$. SD rats were divided into a model group and a CYP2E1 gene-knockout group, and the modeling took 21 days (model group, n=9 rats; and gene-knockout group, n=8 rats). At the end of the experiment, blood was collected from the orbit, a body weight was measured, and then the rats each were sacrificed. The weight and appearance of a liver (color and texture of the liver) were recorded. Some liver specimens were subjected to HE staining, and then the liver lesion and tumorigenesis of rats in each group were observed.

Figure 39A:
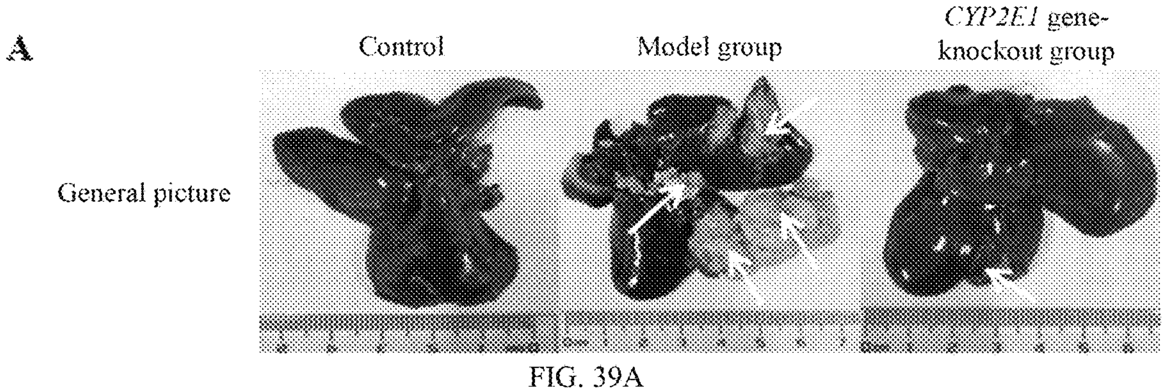
FIGS. 39A-39C show inhibitory effects of CYP2E1 gene knockout on rat liver cancer models constructed through in situ implantation of Walker256 cells into livers, where
Figure 39B:
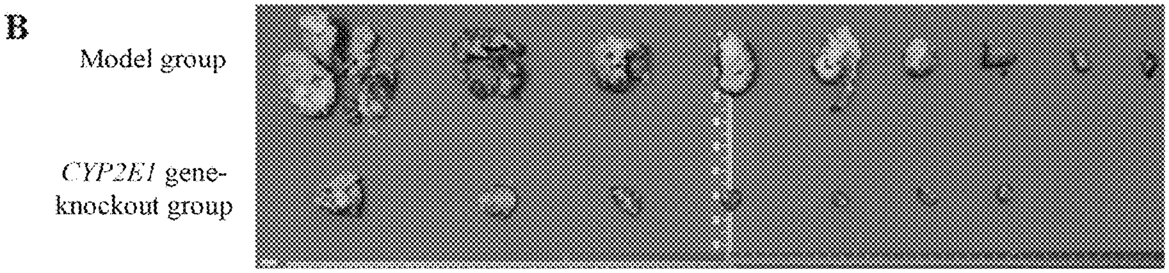
Figure 39C:
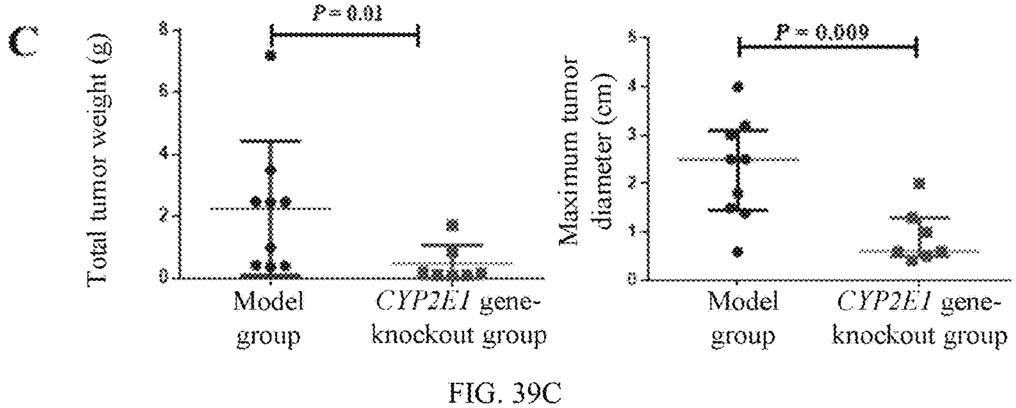

Experimental results: Compared with the model group, the liver tumor growth was significantly inhibited in rats of the CYP2E1 gene-knockout group, with a tumor proliferation inhibition rate as high as 82.0% (as shown in FIGS. 39A-39C), indicating that the CYP2E1 gene knockout can significantly inhibit the occurrence of a tumor in the rat liver transplanted tumor model constructed through in situ implantation of the Walker256 cell.

(3) INTERVENTION OF SMI0 IN A MOUSE LIVER IN SITU TRANSPLANTED TUMOR

Experimental method: A male BALB/c mouse liver transplanted tumor model was constructed through in situ implantation of a liver cancer cell line H22 into the liver, with a cell concentration of $1.5*10^5$. An SMI0 intervention group was divided into a low-dose group, a medium-dose group, and a high-dose group, which were intragastrically administered with the compound SMI0 respectively at 3.3 mg/kg, 10 mg/kg, and 30 mg/kg every day from two days before modeling to the end of the 24-day modeling (model group, n=19 mice; SMI0 compound low-dose group, n=19 mice; SMI0 compound medium-dose group, n=18 mice; and SMI0 compound high-dose group, n=29 mice). At the end of the experiment, blood was collected from the orbit, a body weight was measured, and then the mice each were sacrificed. The weight and appearance of a liver (color and texture of the liver) were recorded. Some liver specimens were subjected to HE staining, and then the liver lesion and tumorigenesis of mice in each group were observed.

Figure 40A:
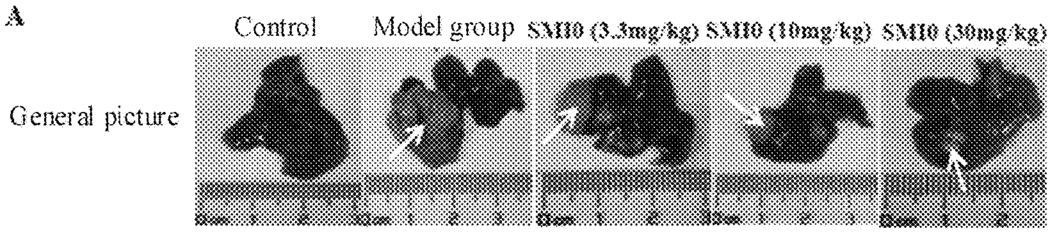
FIGS. 40A-40C show inhibitory effects of the compound SMI0 on mouse liver cancer models constructed through in situ implantation of liver cancer cells H22 into livers, where
Figure 40B:
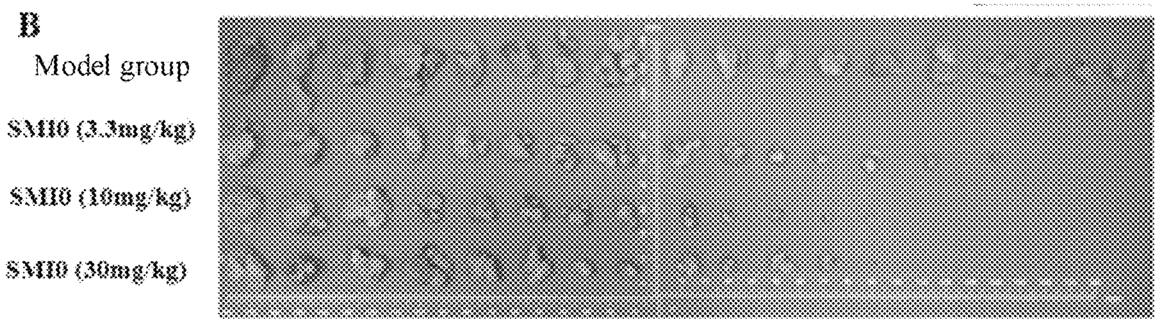
Figure 40C:
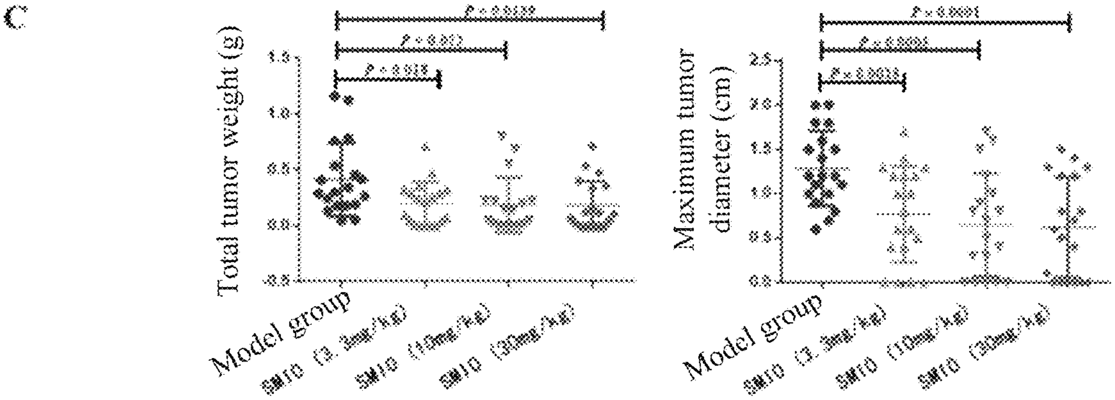

Experimental results: Compared with the model group, the liver H22 tumor incidences in mice of the low-dose, medium-dose, and high-dose SMI0 intervention groups were significantly reduced from 100% in the model group respectively to 78.9%, 72.2%, and 68.4% (as shown in FIGS. 40A-40C, *P<0.05 and P<0.01 vs the model group). FIGS. 40A-40**C show pictures of the liver tumor tissues of mice. If multiple tumors are formed on the liver of a mouse, all of the tumors are cumulatively arranged together to indicate the tumorigenesis of the mouse. A cumulative weight of liver tumors in each animal was measured. It was found that there was tumorigenesis in the liver of each mouse in the model group, and compared with the model group, the tumor proliferation was significantly inhibited in the SMI0 intervention group, that is, the SMI0 intervention significantly inhibited the growth of liver tumors in mice, with a tumor proliferation inhibition rate as high as 71.8%, indicating that the SMI0 administration can significantly inhibit the occurrence and development of a tumor in the liver cancer transplanted tumor model constructed through in situ implantation of the H22 cell.

(4) Inhibition of SMI0 on an Inflammatory Microenvironment of a Mouse Liver In Situ Transplanted Tumor Experimental method: The levels of oxidative stress indexes MDA and T-AOC in the mouse paracancerous liver tissue were determined by a kit method; the expression of the chemokine CXCL-12 in the mouse paracancerous liver tissue was detected by RT-PCR; the expression of proinflammatory cytokines (TNF-α, IL-6, and IL-1β) and inflammation-associated signaling pathway proteins (ARRB1, Src, ITGAV, p-STAT3/STAT3, p-ERK/ERK, and p-P38MAPK/P38MAPK) in the mouse paracancerous liver tissue was detected by a WB method; and the expression of apoptosis-associated proteins and signaling pathways casPase3, cleaved casPase3, p-ERK/ERK, and p-p38MAPK/p38MAPK in the tumor tissue was detected by a WB method.

Figure 41A:
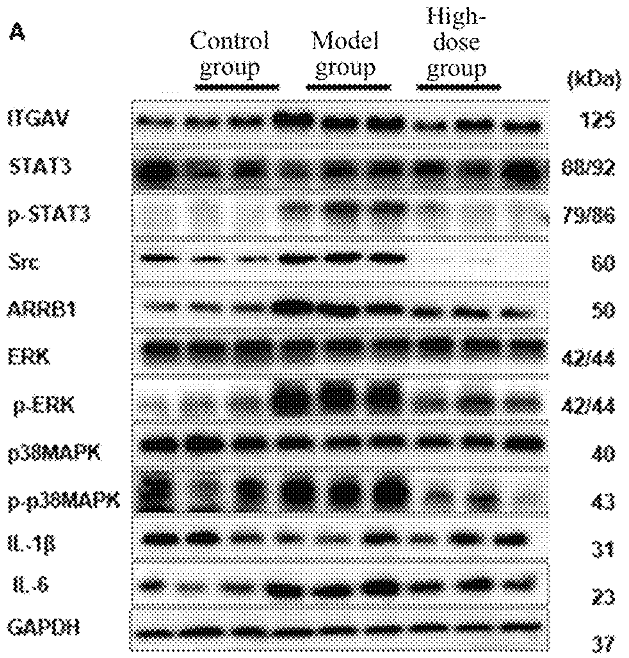
FIGS. 41A-41B show the inhibition of the compound SMI0 on an inflammatory microenvironment in a paracancerous liver tissue of a mouse tumor model constructed through in situ transplantation of H22 cells into a liver, where
Figure 41B:
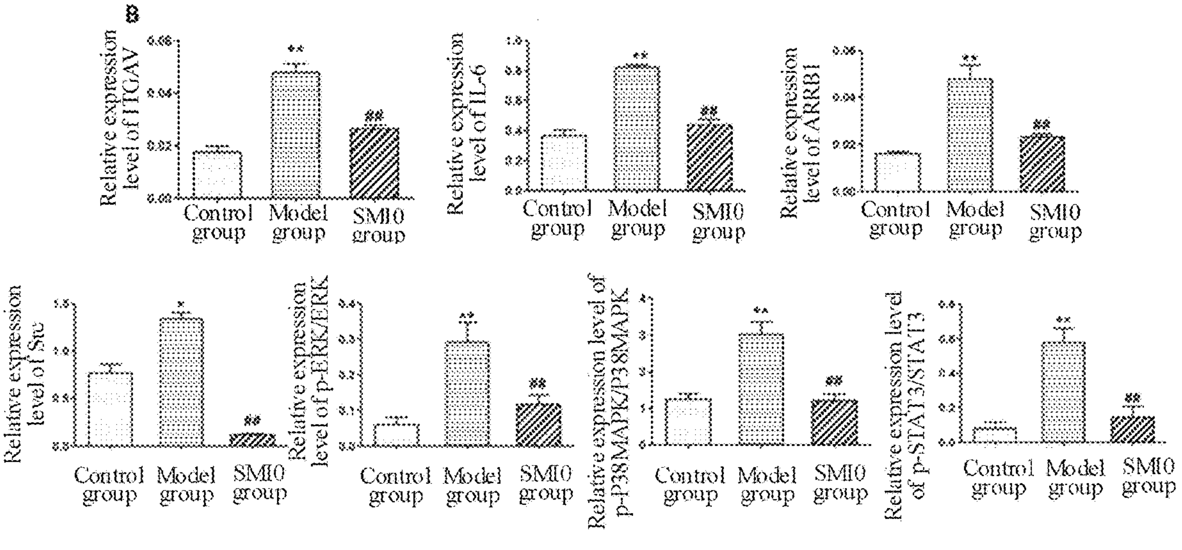
Figure 42A:
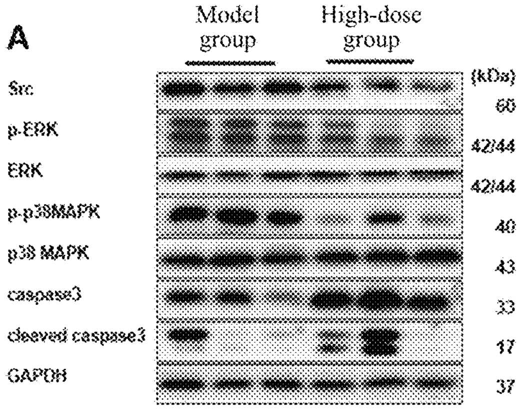
FIGS. 42A-42B show effects of the compound SMI0 on apoptosis and related signaling pathway proteins in a paracancerous liver tissue and a cancer tissue of a mouse tumor model constructed through in situ transplantation of H22 cells into a liver, where
Figure 42B:
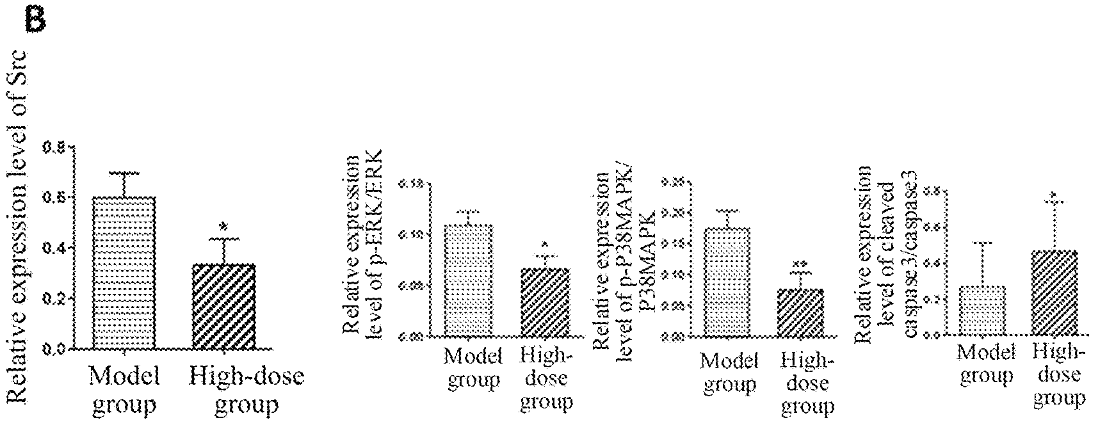

Experimental results: Compared with the sham-operated group, in the model group, the expression of an oxidative stress index MDA, a chemokine CXCL-12, proinflammatory cytokines (TNF-α, IL-6, and IL-10), and inflammation-associated signaling pathway proteins (ARRB1, Src, ITGAV, p-STAT3/STAT3, p-ERK/ERK, and p-p38MAPK/p38MAPK) in the paratumoral liver tissue of mice was significantly up-regulated (P<0.05 or P<0.01), and the expression of a total oxidation resistance index T-AOC was significantly decreased (P<0.01); further, compared with the model group, in the SMI0 intervention group, the expression of the total oxidation resistance index T-AOC was significantly increased (P<0.01), and the expression of other proteins was significantly reduced (P<0.05 or P<0.01) (as shown in FIGS. 41A-41B); and similarly, compared with the model group, in the SMI0 (30 mg/kg) intervention group, the expression of apoptosis-associated proteins cleaved caspase3/caspase3 in the tumor tissue was significantly up-regulated (P<0.01), and the expression of p-ERK/ERK and p-p38MAPK/p38MAPK was significantly down-regulated (P<0.05 or P<0.01) (as shown in FIGS. 42A-42B), indicating that SMI0 can significantly inhibit the activation of oxidative stress and inflammation-associated signaling pathways in the paracancerous liver tissue of the mouse H22 liver in situ transplanted tumor and promote the apoptosis of the tumor.

(5) SMI0 Played an Anti-Liver Cancer Role by Affecting Macrophages.

A. SMI0 Exhibited No Direct Inhibitory Effect on Liver Cancer Cells.

Experimental method: HepG2 liver cancer cells and H22 liver cancer cells in a logarithmic growth phase each were selected and inoculated into a 96-well plate at a concentration of $1*10^5$ cells/mL, and then 100 μL of a basic medium including SMI0 at different concentrations (0 μmol/L, 0.16 μmol/L, 0.8 μmol/L, 4 μmol/L, 20 μmol/L, and 100 μmol/L) was added to each well; and 24 h later, the proliferation activity of HepG2 was determined by a CCK8 method, a migration ability of HepG2 was determined by wound-healing assay, and an apoptosis ability of HepG2 was determined by flow cytometry (FCM).

Figure 43A:
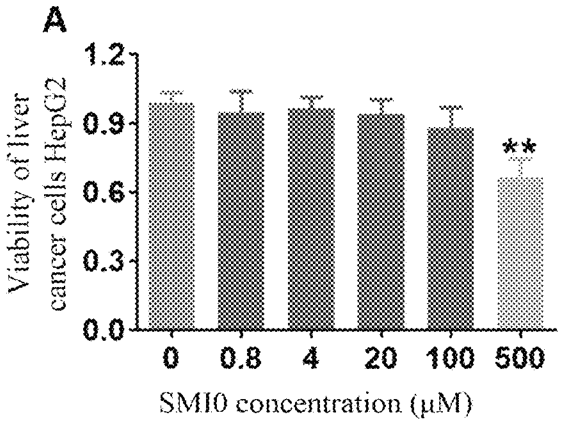
FIGS. 43A-43B show that the compound SMI0 has no direct inhibitory effect on liver cancer cells, where
Figure 43B:
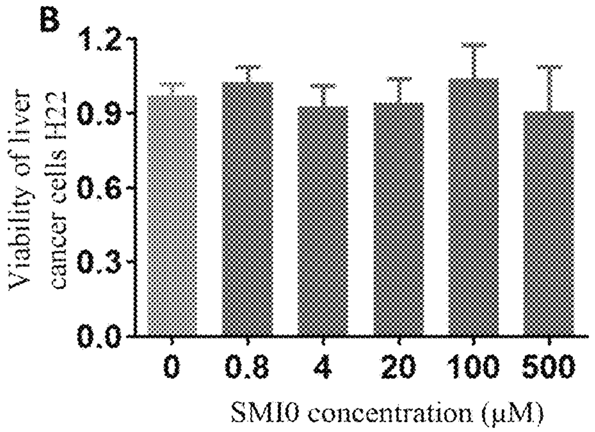
Figure 44A:
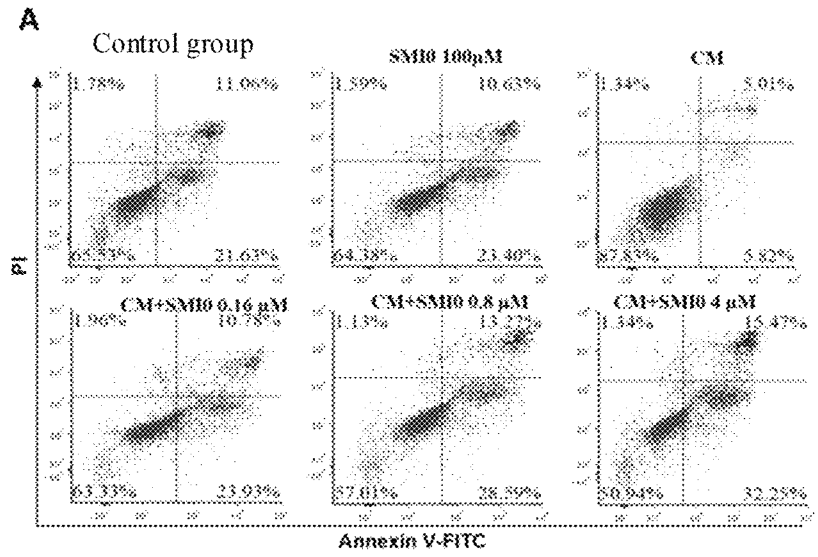
FIGS. 44A-44E show that the compound SMI0 plays an anti-liver cancer role by influencing macrophages, where
Figure 44B:
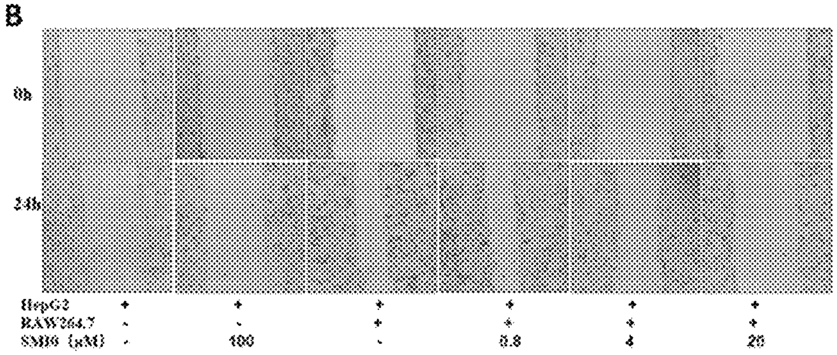
Figure 44C:
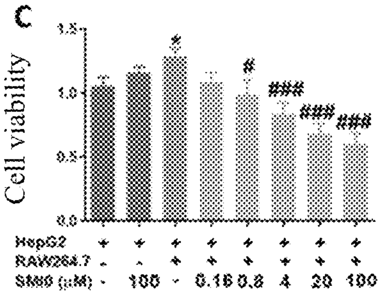
Figure 44D:
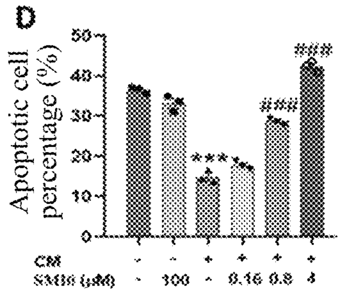
Figure 44E:
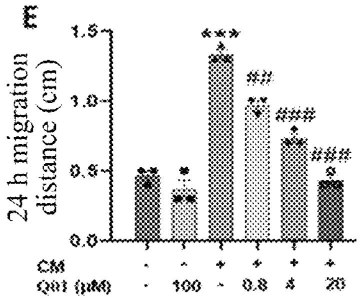

Experimental results: SMI0 at a test concentration (up to 100 μmol/L) exhibited no significant inhibitory effect on the proliferation, migration, and apoptosis of HepG2 and H22 liver cancer cells (as shown in FIGS. 43A-43B), indicating that the CYP2E1 inhibitor SMI0 has no direct inhibitory effect on liver cancer cells.

B. SMI0 Played an Anti-Liver Cancer Role by Affecting Macrophages.

Experimental method: A supernatant of a murine macrophage RAW264.7 was collected to establish a co-cultivation system with the HepG2 liver cancer cell, thereby simulating a macrophage inflammatory microenvironment of liver cancer. In the SMI0 intervention groups, SMI0 was added at different concentrations (0 μmol/L, 0.16 μmol/L, 0.8 μmol/L, 4 μmol/L, 20 mol/L, and 100 μmol/L) while interleukin was added for induction. Culture supernatants of the SMI0 intervention groups were collected to prepare conditional media. HepG2 liver cancer cells in a logarithmic growth phase were adopted. The proliferation activity of HepG2 was determined by a CCK8 method, a migration ability of HepG2 was determined by wound-healing assay, and an apoptosis ability of HepG2 was determined by FCM.

Experimental results: Compared with the group in which HepG2 liver cancer cells were cultivated alone, in the RAW264.7 macrophage co-cultivation group, the proliferation activity ($P<0.05$) and migration ability ($P<0.001$) of the HepG2 cells were significantly enhanced, and the apoptosis ability of the HepG2 cells was significantly reduced ($P<0.001$); and compared with the macrophage co-cultivation group, in the SMI0 intervention groups (especially 4 μmol/L), the proliferation activity ($P<0.001$) and migration ability ($P<0.001$) of the HepG2 liver cancer cells were significantly weakened, and the apoptosis ability of the HepG2 liver cancer cells was significantly enhanced ($P<0.001$) (as shown in FIGS. 44A-44E), indicating that the inhibition of the CYP2E1 inhibitor SMI0 on liver cancer may be achieved by affecting macrophages in a paratumoral microenvironment to inhibit the proliferation and migration of HepG2 liver cancer cells and promote the apoptosis of HepG2 liver cancer cells.

It can be seen from the above results that SMI0 has a significant prevention and treatment effect on the occurrence and development of a tumor in a mouse liver cancer model constructed through in situ implantation of H22 cells, indicating that the compound SMI0 can be used for the prevention and treatment of clinical liver cancer.

Example 17 Inhibition of SMI0 on the Glioma Proliferation in Mice (1) CYP2E1 Changes in Clinical Glioma Patients Experimental method: The changes of CYP2E1 expression in paracancerous tissues of 32 clinical glioma patients were investigated with brain tissues of 46 healthy individuals as a control, and the changes of CYP2E1 protein contents in the paracancerous tissues of the glioma patients were determined. CYP2E1 mRNA levels in paratumoral brain tissues of 12 glioma patients were investigated with brain tissues of 6 healthy individuals as a control, and the CYP2E1 mRNA level changes in the paratumoral brain tissues were determined.

Figure 45A:
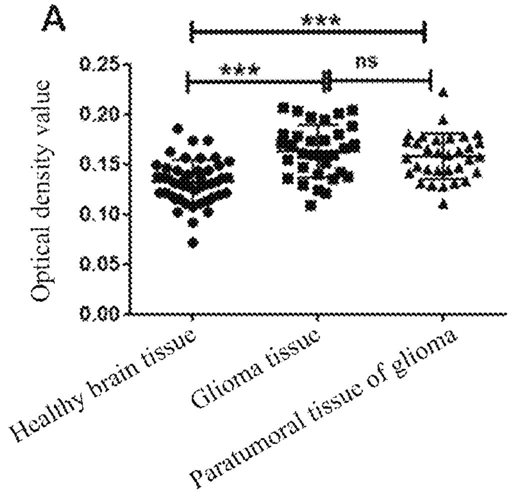
FIGS. 45A-45B show a high expression level of CYP2E1 in a paratumoral tissue of a glioma patient, where
Figure 45B:
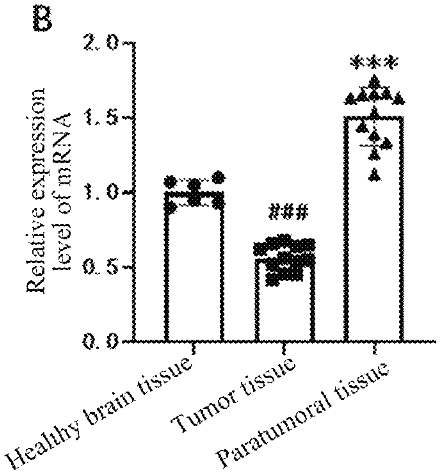

Experimental results: Immunohistochemical results showed that the expression of CYP2E1 in the paratumoral tissues of the glioma patients was significantly higher than that in the healthy brain tissues (as shown in FIG. 45A, *$P<0.001$ vs the healthy brain tissue group); and qPCR results showed that the expression of CYP2E1 mRNA in the paratumoral tissues of the glioma patients was significantly higher than that in the healthy brain tissues (as shown in FIG. 45B, *$P<0.001$ vs the healthy brain tissue group).

(2) Inhibition of CYP2E1 Knockout on a Mouse Brain In Situ Transplanted Tumor

Experimental method: A female C57/BL6 mouse brain glioma in situ model was constructed with a mouse brain glioma cell line GL261. Molding method: The skull was perforated at a position 0.15 mm posterior to and 2 mm at the right of the anterior fontanelle, 5 μL of a GL261 single-cell suspension ($1\times10^6$ cells in total) was drawn with a microsyringe, and then a needle of the microsyringe was slowly vertically inserted along a needle hole with an insertion depth of 4 mm and a retracting depth of 1 mm; and this step was repeated 10 times, and tumor-bearing cells were then slowly injected at a speed of 1 μL/min. A model group and a CYP2E1 gene-knockout group were adopted for the experiment, and the modeling took about 21 days (model group, n=10 mice; and CYP2E1 gene-knockout group, n=6 mice). At the end of the experiment, a body weight was measured, blood was collected from the orbit, then the mice each were sacrificed, and brain tissues were collected. Brain tissue specimens were subjected to HE staining, and then the tumorigenesis and tumor size of mice in each group were observed.

Figure 46:
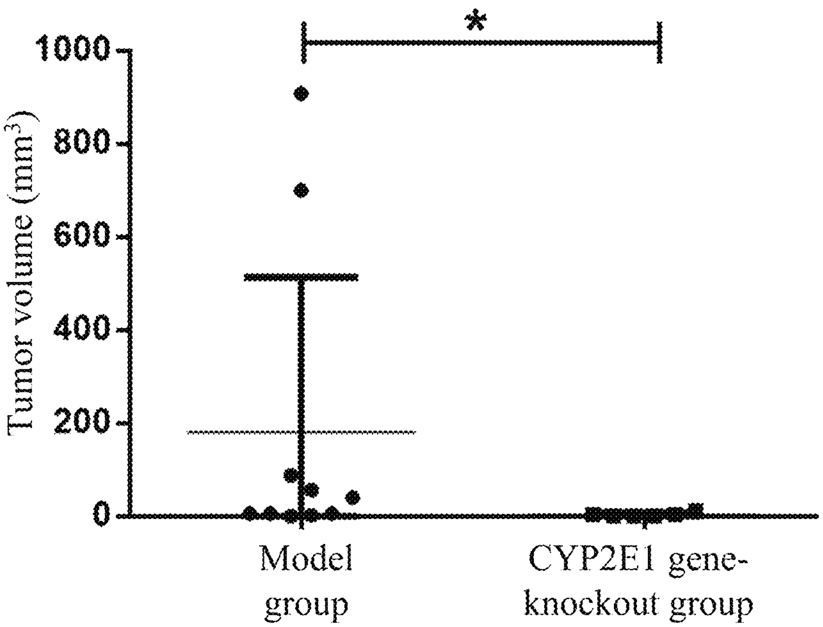
FIG. 46 shows an inhibitory effect of CYP2E1 gene knockout on a mouse glioma model constructed through in situ implantation of glioma GL261 cells into the brain.

Experimental results: Compared with the model group, the CYP2E1 gene knockout significantly inhibited the glioma growth in mice (as shown in FIG. 46, *$P<0.05$ vs the wild-type (WT) model group), indicating that the CYP2E1 gene knockout can significantly inhibit the occurrence of a tumor in the GL261 cell brain in situ transplanted mouse glioma model.

(3) Intervention of SMI0 in a Mouse Brain In Situ Transplanted Tumor

Experimental method: A female C57/BL6 mouse glioma model was constructed through in situ implantation of a glioma cell line GL261, with a cell concentration of $1*10^6$. Experimental groups: sham-operated group (n=9); model group (n=10); temozolomide group (50 mg/kg, ig, n=11); SMI0 low-dose group (3.3 mg/kg, ig, n=13); SMI0 medium-dose group (10 mg/kg, ig, n=13); and SMI0 high-dose group (30 mg/kg, ig, n=13). The SMI0 intervention group was intragastrically administered with the compound SMI0 every day starting from three days before modeling, and the positive drug group was administered on day 3 to day 7 and day 10 to day 14 after surgery. The modeling took about 21 days. At the end of the experiment, blood was collected from the orbit, a body weight was measured, then the mice each were sacrificed, and brain tissues were collected. Brain tissue specimens were subjected to HE staining, and then the brain tissue lesion and tumorigenesis of mice in each group were observed.

Figure 47A:
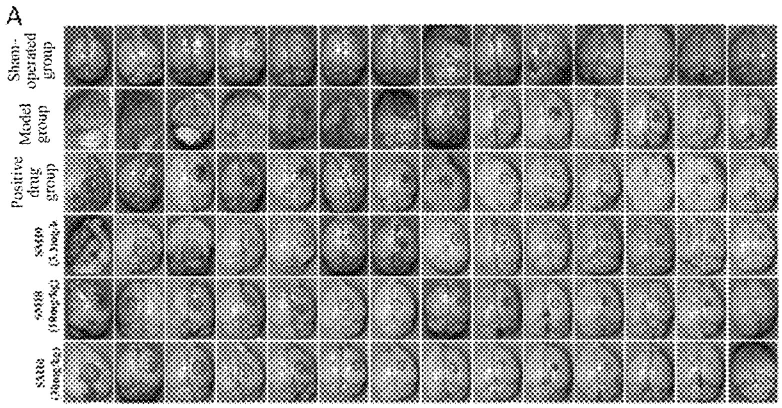
FIGS. 47A-47D show an inhibitory effect of the compound SMI0 on a mouse glioma model constructed through in situ implantation of glioma GL261 cells into the brain, where
Figure 47B:
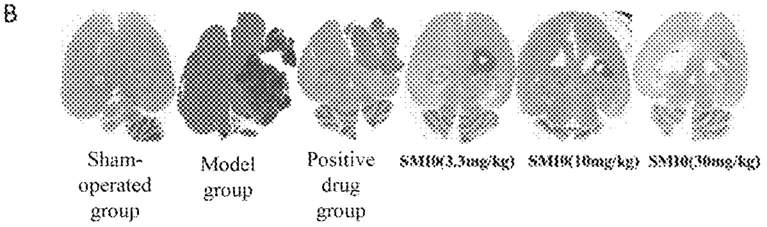
Figure 47C:
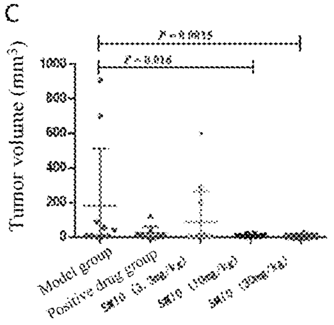

Experimental results: Compared with the model group, the SMI0 intervention significantly inhibited the glioma growth in mice, where the SMI0 high-dose group (30 mg/kg) had the optimal inhibitory effect, with a tumor proliferation inhibition rate as high as 97.6% (as shown in FIGS. 47A-47C, *$P<0.05$ vs the model group and **$P<0.01$ vs the model group), indicating that SMI0 can significantly inhibit the occurrence and development of a tumor in the GL261 cell brain in situ transplanted mouse glioma model.

Figure 47D:
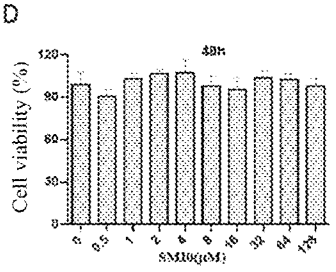

In addition, an in vitro inhibition experiment (FIG. 47D) showed that SMI0 in a concentration range of 0 μM to 128 μM continuously acted on GL261 cells for 48 h, and exhibited no significant inhibitory effect on GL261.

It can be seen from the above results that the CYP2E1 gene knockout can significantly inhibit the occurrence and development of glioma in mice, and the CYP2E1 inhibitor SMI0 has a significant prevention and treatment effect on the occurrence and development of glioma in GL261 cell brain in situ implanted mice, indicating that the compound SMI0 can be used for the prevention and treatment of clinical glioma.

(4) Correlation Between CYP2E1 Activity and Tumor Severity in a Glioma Model after SMI0 Inhibition Experimental method: A calcium precipitation method was used to prepare a mouse liver microsome, and a Braford method was used to determine a protein concentration in the microsome. An incubation system was prepared with 2×PBS, a CZX solution, and the liver microsome at a final concentration of 0.5 mg/mL, and then pre-incubated at 37° C. for 5 min; NADPH was added to initiate a reaction, and a resulting mixture was incubated at 37° C. for 30 min and then placed on ice to terminate the reaction; and ethyl acetate was added to extract 6-hydroxychlorzoxazone, a resulting mixture was vortexed and centrifuged, and a resulting upper organic phase was collected and blow-dried with nitrogen. A peak area of a CZX metabolite 6-hydroxychlorzoxazone was detected by HPLC under the following conditions: methanol:water=56:44, and detection wavelength: 287 nm. A concentration A C of the metabolite 6-hydroxychlorzoxazone was calculated through substitution into a standard curve; and a reaction rate of conversion of CZX into 6-hydroxychlorzoxazone was calculated according to V(pmol/min/mg)=(AC*1000)/(B*T) to evaluate an enzymatic activity of CYP2E1, where B represents a protein concentration of the microsome (mg/mL) and T represents an incubation time (min). A correlation between CYP2E1 activity and tumor size in the mouse glioma model was analyzed.

Figure 48A:
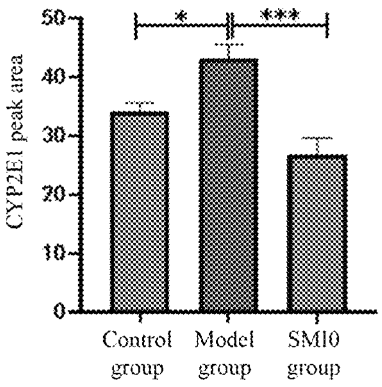
FIGS. 48A-48B show a change of CYP2E1 activity and a correlation between CYP2E1 activity and tumor severity in a mouse model constructed through in situ transplantation of glioma, where the FIG. 48A shows a change of CYP2E1 activity in mice of each group; and the FIG. 48B shows a correlation between CYP2E1 activity and lung tumor weight in mice.
Figure 48B:
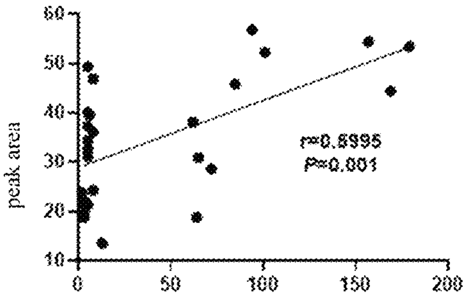

Experimental results: Compared with the sham-operated group, the CYP2E1 activity in the model group was significantly increased (P<0.05); and compared with the model group, the CYP2E1 activity in the SMI0 intervention group was significantly reduced (P<0.001), indicating that SMI0 can effectively inhibit the increase in enzymatic activity of CYP2E1 in the liver tissue of the in situ transplanted mouse glioma model, and the CYP2E1 activity of mice is significantly positively correlated with the tumor weight of the in situ transplanted mouse glioma model (r=0.5995, P<0.001) (as shown in FIGS. 48A-48B). It can be known that the enzymatic activity of CYP2E1 is related to glioma, and an anti-glioma effect of SMI0 may be related to the inhibition on enzymatic activity of CYP2E1.

(5) SMI0 Inhibited the Growth of GL261 Glioma Through a Paratumoral Microenvironment.

A. SMI0 Exhibited No Direct Inhibitory Effect on Glioma Cells.

Experimental method: GL261 murine glioma cells and U251 human glioma cells in a logarithmic growth phase each were selected and inoculated into a 96-well plate at a concentration of $5*10^5$ cells/mL, then 100 μL of a cell suspension was added to each well, and 12 h later, a medium was discarded; 200 μL of a basic medium including SMI0 at different concentrations (0 mol/L, 0.16 μmol/L, 0.8 μmol/L, 4 μmol/L, 20 μmol/L, and 100 μmol/L) was added to each well, and 24 h later, 10 μL of a CCK8 reagent was added to each well; and the cells were further cultivated for 2 h, and an absorbance OD value of each well was determined at 450 nm by a microplate reader. 3 replicates were set for each well, and an average was taken. The proliferation activity was calculated based on the OD value.

Figure 49A:
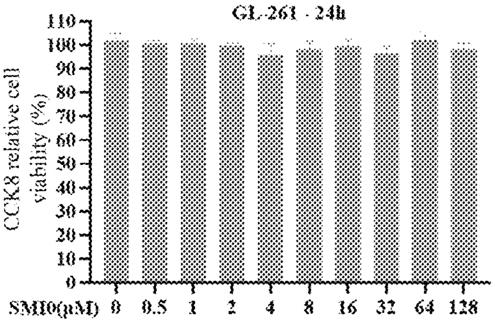
FIGS. 49A-49B show that the compound SMI0 has no direct effect on GL261 (FIG. 49A) or U251 (FIG. 49B) glioma cells.
Figure 49B:
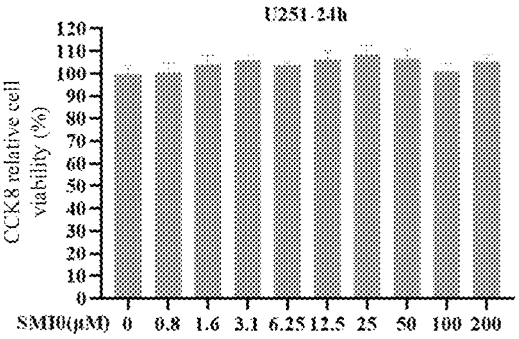
Figure 50A:
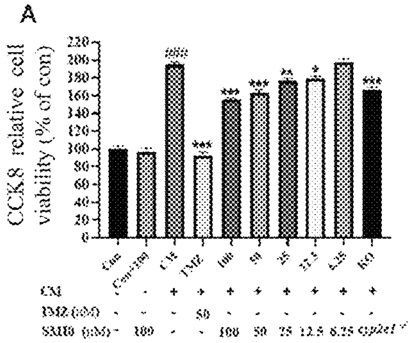
FIGS. 50A-50D show that the compound SMI0 inhibits GL261 or U251 glioma by inhibiting primary microglial cells or source microglial cells HMC-3, where
Figure 50B:
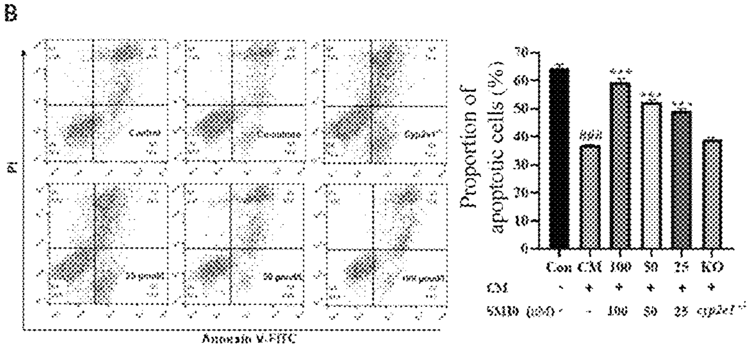
Figure 50C:
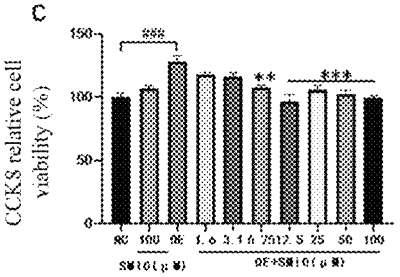
Figure 50D:
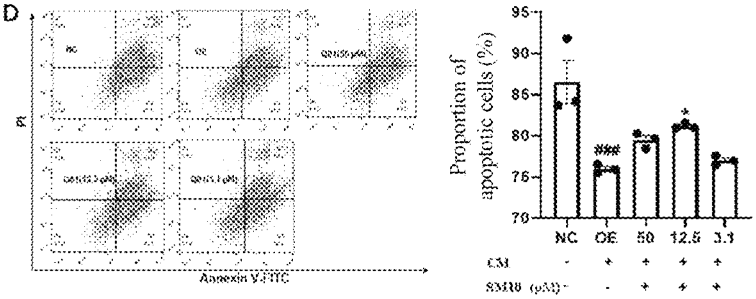

Experimental results: SMI0 at a test concentration (up to 128 μmol/L or 200 μmol/L) exhibited no significant inhibitory effect on the proliferation of GL261 and U251 glioma cells (as shown in FIGS. 49A-49B).

B. SMI0 Resisted Glioma Through Paratumoral Microglial Cells and Astrocytes.

Experimental method: 10 1-2 d newborn C57BL/6 WT mice and 6 $CYP2E1^{-/-}$ mice were taken, primary microglial cells and astrocytes were collected and inoculated into 6-well plates, and 24 h later, culture supernatants were taken and co-cultivated with glioma cells. Experimental groups: control group; M2 model group; high-concentration, medium-concentration, and low-concentration SMI0 (50 μmol/L, 12.5 μmol/L, and 3.1 μmol/L) groups; and CYP2E1 gene-knockout group. 24 h later, supernatants were discarded; and IL-4 and IL-13 each were added at 20 ng/mL to induce the transformation of microglial cells into the M2 type in the M2 model group and the high-concentration, medium-concentration, and low-concentration SMI0 groups, and different concentrations of SMI0 (50 μmol/L, 12.5 μmol/L, and 3.1 μmol/L) were also added in the intervention groups. The proliferation of glioma cells was determined by a CCK8 method, and an apoptosis proportion was determined by an Annexin V-FITC-PI apoptosis staining kit.

Experimental results: Compared with the group in which GL261/U251 glioma cells were cultivated alone, in the M2 microglial cell co-cultivation group, the proliferation activity of GL261/U251 cells was significantly enhanced, and the apoptosis was significantly inhibited; and compared with the M2 microglial cell co-cultivation group, in the SMI0 intervention group (50 mol/L), the proliferation of GL261/U251 cells was significantly inhibited (P<0.001), and the apoptosis of GL261 cells was promoted (as shown in FIGS. 50A-50D), indicating that the inhibition of the CYP2E1 inhibitor SMI0 on GL261 and U251 in situ transplanted tumors may be related to microglial cells.

Figure 51A:
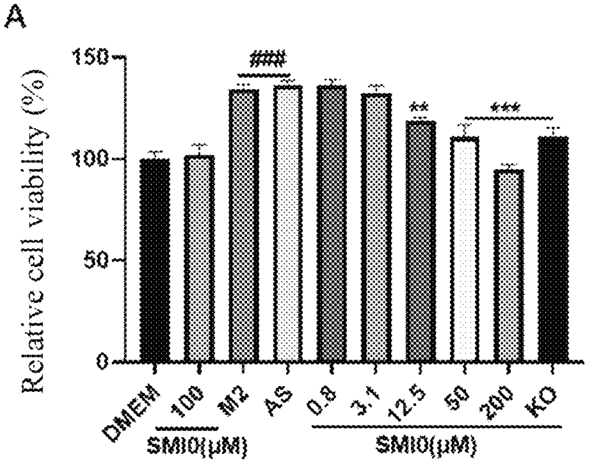
FIGS. 51A-51B show that the compound SMI0 inhibits GL261 glioma by inhibiting primary astrocytes, where
Figure 51B:
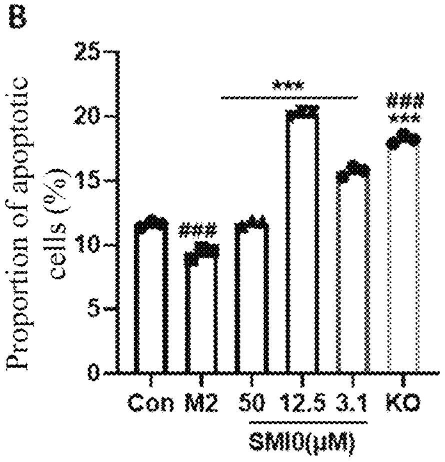
Figure 52A:
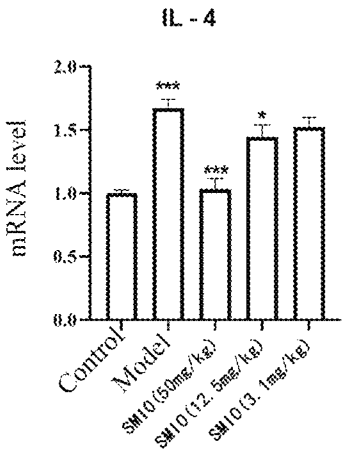
FIGS. 52A-52F show the inhibition of the compound SMI0 on M2 polarization of primary microglial cells.
Figure 52B:
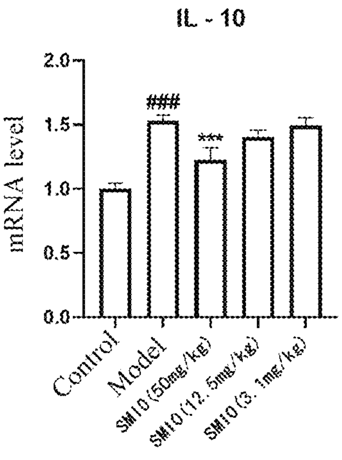
Figure 52C:
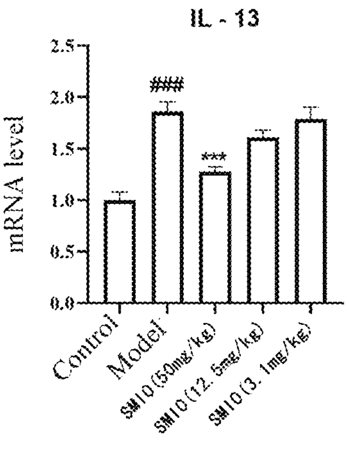
Figure 52D:
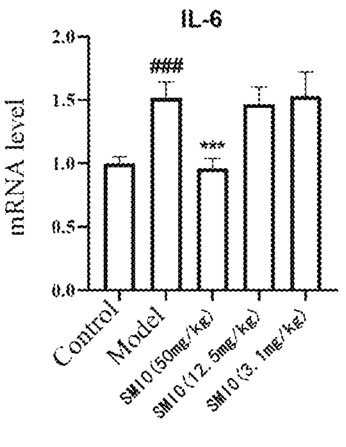
Figure 52E:
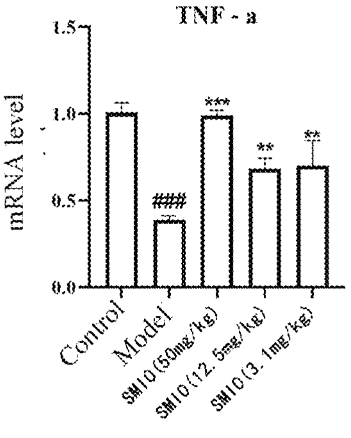
Figure 52F:
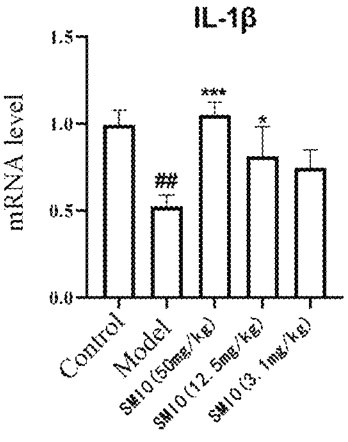
Figure 53A:
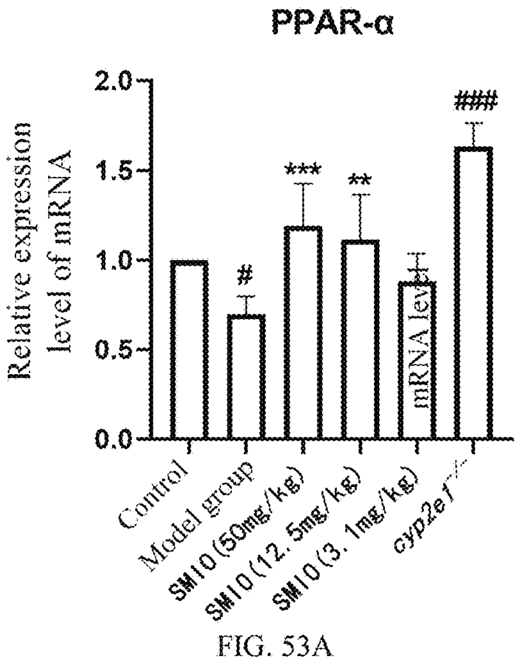
FIGS. 53A-53D show the inhibition of the compound SMI0 on cholesterol metabolism of astrocytes.
Figure 53B:
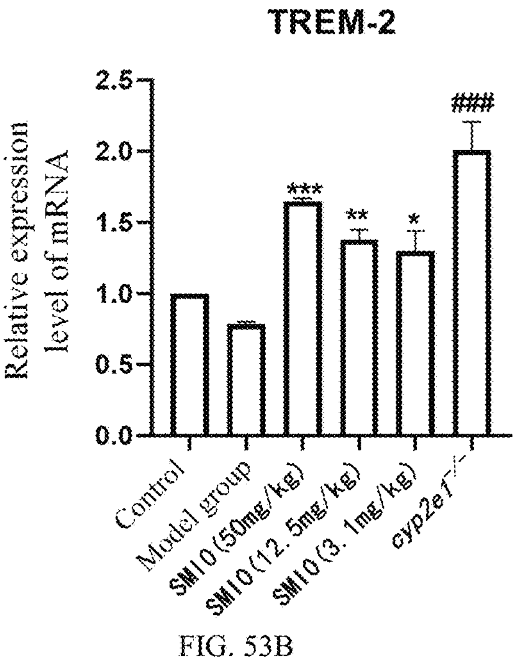
Figure 53C:
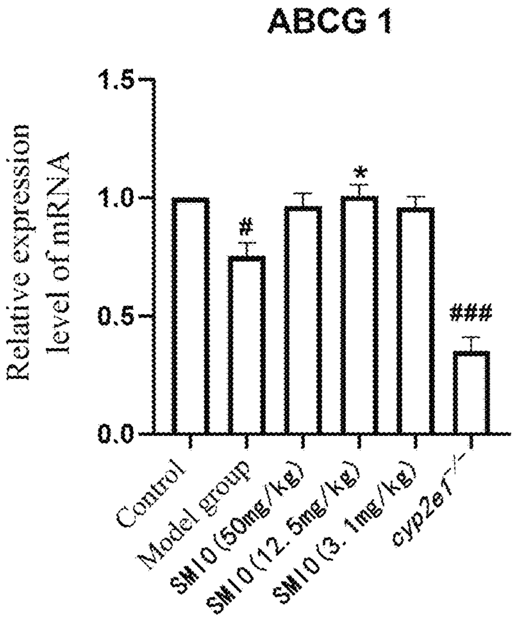
Figure 53D:
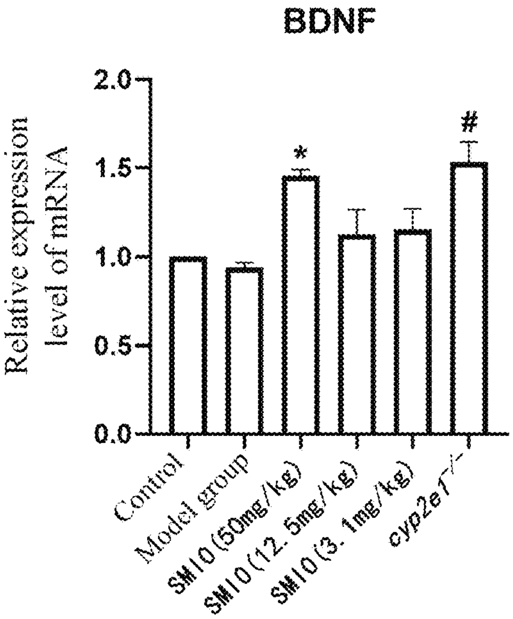

Compared with the group in which GL261 glioma cells were cultivated alone, in the M2 astrocyte co-cultivation group, the proliferation activity of GL261 cells was significantly enhanced (P<0.01), and the apoptosis was significantly inhibited (P<0.01); and compared with the M2 astrocyte co-cultivation group, in the SMI0 intervention group (50 μmol/L), the proliferation activity of GL261 cells was significantly weakened (P<0.05) (as shown in FIGS. 51A-51B, P<0.01), indicating that the inhibition of the CYP2E1 inhibitor SMI0 on GL261 in situ transplanted tumors may be related to astrocytes.

C. The Inhibition of SMI0 on Glioma Growth was Related to the Inhibition on M2 Polarization of Microglial Cells and the Cholesterol Metabolism of Astrocytes.

Experimental method: Astrocytes in the co-cultivation group were collected, RNA was extracted and reverse-transcribed into cDNA, and the changes of inflammatory factor and cholesterol metabolism-associated genes were detected by qPCR.

Experimental results: Compared with the group in which GL261 glioma cells were cultivated alone, in M2 microglial cells, the levels of IL-4, IL-10, and IL-13 were significantly increased, and the level of the lipid metabolism-associated gene PPAR-a was significantly reduced; and compared with the M2 microglial cell co-cultivation group, in the SMI0 intervention group (50 mol/L), the levels of IL-4, IL-10, and IL-13 were significantly reduced, and the level of the lipid metabolism-associated gene PPAR-a was significantly increased (as shown in FIGS. 52A-52F and FIGS. 53A-53D), indicating that the inhibition of the CYP2E1 inhibitor SMI0 on GL261 in situ transplanted tumors may be related to the inhibition of M2 polarization of microglial cells and the cholesterol metabolism of astrocytes.

Example 18 Inhibition of SMI0 on the Occurrence and Development of Ovarian Cancer in Mice (1) Ovarian Cancer In Situ Transplanted Tumor Experimental method: A female C57/6 mouse ovarian cancer in situ transplanted tumor model was constructed with a murine ovarian cancer ID-8 cell line at a cell concentration of $1\times10^6$. A model group and an SMI0 intervention group were set for the experiment. The intervention group was intragastrically administered with the SMI0 compound at 30 mg/kg every day from three days before modeling to the end of the 60-day modeling (model group, n=15; and SMI0 compound (30 mg/kg) group, n=12). At the end of the experiment, blood was collected from the orbit, a body weight was measured, then the mice each were sacrificed, and ovary tissues and tumor tissues were collected. Ovary tissue specimens were subjected to HE staining, and then the ovary tumor tissue and tumorigenesis of mice in each group were observed.

Figure 54A:
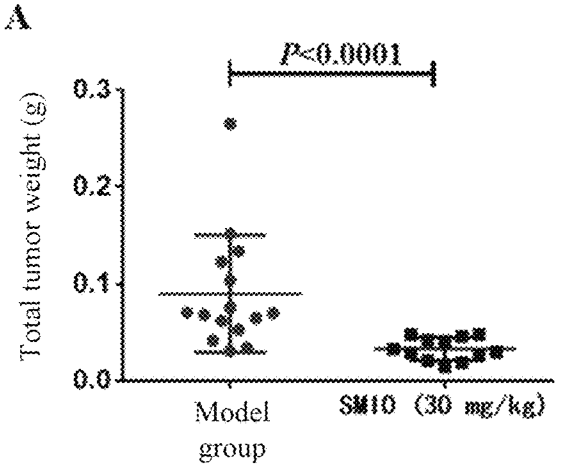
FIGS. 54A-54C show an inhibitory effect of the compound SMI0 on a mouse ovarian cancer model constructed through in situ implantation of ovary cancer ID-8 cells into the ovary, where

Experimental results: Compared with the model group, the SMI0 intervention significantly inhibited the growth of ovarian cancer in mice, with a tumor proliferation inhibition rate as high as 63.14% and an ascites weight inhibition rate as high as 76.40% (as shown in FIG. 54A), indicating that the SMI0 administration can significantly inhibit the occurrence and development of a tumor in the ID-8 ovarian cancer in situ transplanted tumor model.

Figure 54B:
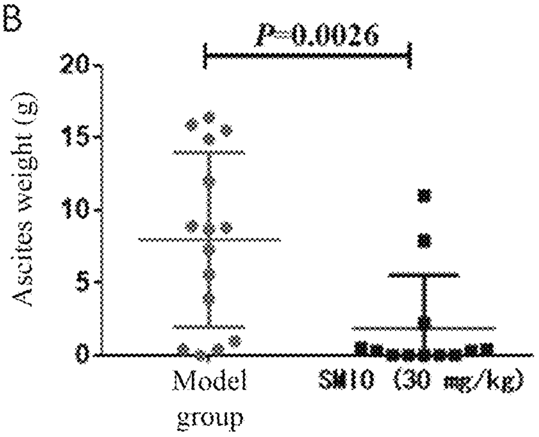
Figure 54C:
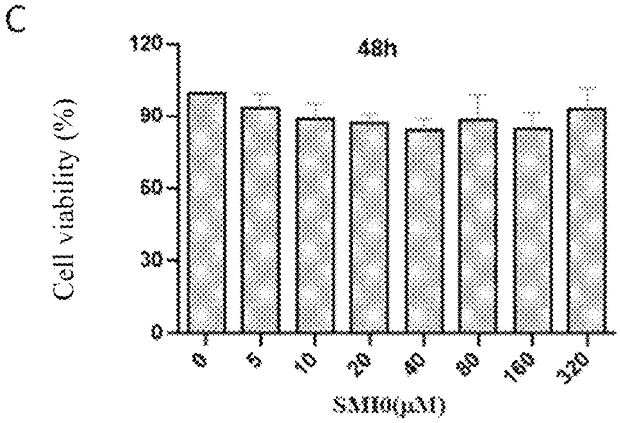

In addition, an in vitro inhibition experiment (FIG. 54B) showed that SMI0 in a concentration range of 0 μM to 320 μM continuously acted on ID-8 cells for 48 h, and exhibited no significant inhibitory effect on ID-8.

(2) Ovarian Cancer Abdominal Transplanted Tumor

Experimental method: A female C57/6 mouse ovarian cancer abdominal transplanted tumor model was constructed with an ovarian cancer murine ID8 cell line at a cell concentration of $2.5\times10^6$. A model group and an SMI0 intervention group were set for the experiment. The intervention group was intragastrically administered with the SMI0 compound at 30 mg/kg every day from three days before modeling to the end of the 30-day modeling (model group, n=10 mice; and SMI0 compound (30 mg/kg) group, n=11 mice). At the end of the experiment, blood was collected from the orbit, a body weight was measured, then the mice each were sacrificed, and ovary tissues were collected. Ovary tissue specimens were subjected to HE staining, and then the ovary tissue lesion and tumorigenesis of mice in each group were observed.

Figure 55A:
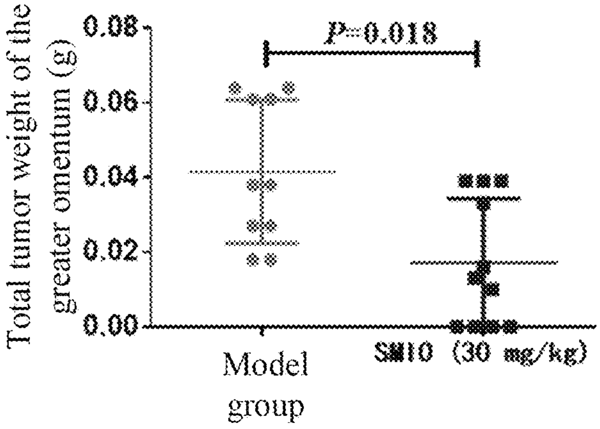
FIGS. 55A-55B show an inhibitory effect of the compound SMI0 on a mouse model constructed through abdominal transplantation of ovarian cancer ID-8 cells, where
Figure 55B:
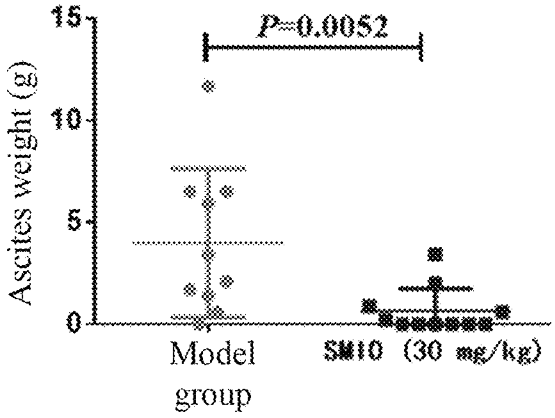

Experimental results: Compared with the model group, in the SMI0 compound (30 mg/kg) intervention group, the body weight of mice was significantly reduced and the ascites volume was significantly reduced, that is, the administration of the SMI0 compound significantly inhibited the ascites production and tumor progression of the ovarian cancer abdominal transplanted tumor in mice, where an inhibition rate for tumor proliferation of the greater omentum was as high as 58.70%, and an inhibition rate for the ascites weight was 83.78% (as shown in FIGS. 55A-55B), indicating that the SMI0 administration can significantly inhibit the occurrence and development of a tumor in the ID-8 ovarian cancer abdominal transplanted tumor model.

It can be seen from the above results that the CYP2E1 inhibitor SMI0 has a significant prevention and treatment effect on the occurrence and development of the ID-8 ovarian cancer in situ transplanted tumor and abdominal transplanted tumor, indicating that the compound SMI0 can be used for the prevention and treatment of ovarian cancer.

Example 19 Inhibition of SMI0 on Rheumatoid Arthritis in Rats (1) Inhibition of CYP2E1 Gene Knockout on Collagen-Induced Rheumatoid Arthritis in Rats Experimental method: A collagen emulsion was prepared with collagen and incomplete freund's adjuvant (IFA) in a volume ratio of 1:1 and then used to construct an SD rat rheumatoid arthritis model. A model group and a CYP2E1 gene-knockout group were set. Each rat was injected subcutaneously with 0.25 mL of the collagen emulsion through the tail for a first immunization, and one week later, a second immunization was conducted in the same way as the first immunization. Within one week after the second immunization, if a rat arthritis score was greater than or equal to 4 (0 point: no redness and swelling; 1 point: slight swelling of a little toe joint; 2 points: swelling of a toe joint and a sole; 3 points: swelling of a toenail below an ankle; 4 points: swelling of the whole foot including an ankle; and 16 points: total points for four feet), it was determined that the modeling was successful. After the modeling was successful, a thickness of each of the left and right hindfeet and the left and right forefeet of rats was measured every day by a vernier caliper, and a volume of each of the left and right hindfeet of rats was measured by a rat foot swelling measuring instrument (which was measured every 12 h in the first 3 days). A foot swelling rate of each rat was calculated according to a change of a hindfoot volume of the rat relative to a hindfoot volume of the rat before the modeling at each time point, and a difference in foot swelling rate between groups of rats was analyzed. After the successful modeling, blood was collected from the orbit on day 7; rats were sacrificed on day 20, blood was collected, and serum was isolated; and tissues such as ankles, toe joints, spleens, and livers were collected. The tissues were subjected to a decalcification treatment and then to HE staining, and the joint lesion, synovial hyperplasia, and connective tissue proliferation were observed under a microscope.

Figure 56A:
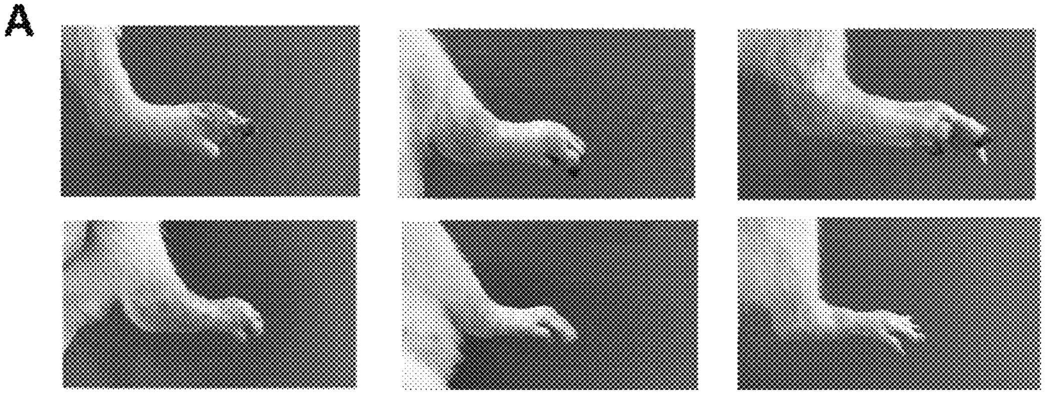
FIGS. 56A-56B show an inhibitory effect of CYP2E1 gene knockout on a collagen-induced rat rheumatoid arthritis model, where
Figure 56B:
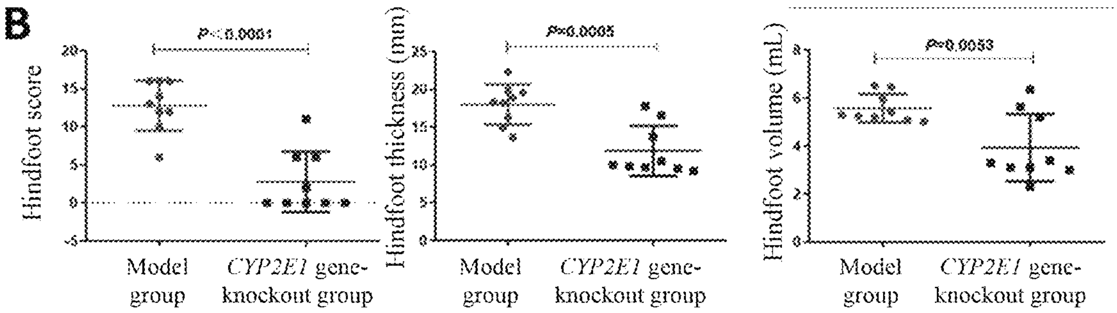

Experimental results: Compared with the model group, in the CYP2E1 gene-knockout group, a success rate of rat modeling was 40%, which was significantly lower than that of the model group (90%); and a joint swelling degree of rats was also significantly lower than that of the model group ($P<0.05$) (as shown in FIGS. 56A-56B), indicating that the CYP2E1 gene knockout can significantly reduce the incidence of collagen-induced rheumatoid arthritis and improve the swelling degree in rats.

(2) Inhibition of SMI0 on Collagen-Induced Rheumatoid Arthritis in Rats

Experimental method: A collagen emulsion was used to construct an SD rat rheumatoid arthritis model. 50 rats successfully modeled were randomly divided into five groups: model group (normal saline (NS), 0.5 mL/kg, i.g.); positive control group (celecoxib, 5 mg/kg, i.g.); SMI0 low-dose group (18.75 mg/kg, i.g.); SMI0 medium-dose group (37.5 mg/kg, i.g.); and SMI0 high-dose group (75 mg/kg, i.g.). The rats each were administered once every day starting from the first day after successful modeling. A thickness of each of the left and right hindfeet and the left and right forefeet of rats was measured every day by a vernier caliper, and a volume of each of the left and right hindfeet of rats was measured by a rat foot swelling measuring instrument (which was measured every 12 h in the first 3 days). A foot swelling rate of each rat was calculated according to a change of a hindfoot volume of the rat relative to a hindfoot volume of the rat before the modeling at each time point, and a difference in foot swelling rate between groups of rats was analyzed. After the successful modeling, blood was collected from the orbit on day 7; rats were sacrificed on day 20, blood was collected, and serum was isolated; and tissues such as ankles, toe joints, spleens, and livers were collected. The tissues were subjected to a decalcification treatment and then to HE staining, and the joint lesion, synovial hyperplasia, and connective tissue proliferation were observed under a microscope.

Figure 57A:
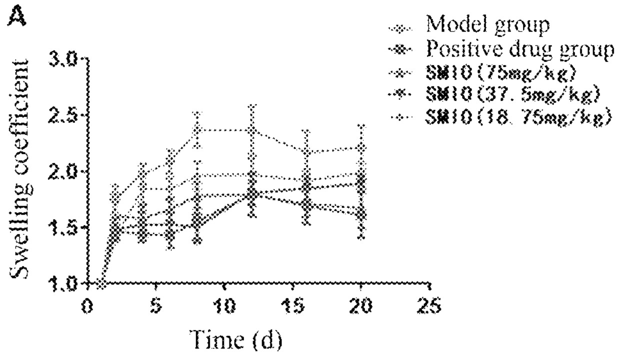
FIGS. 57A-57B show an inhibitory effect of the compound SMI0 on a collagen-induced rat rheumatoid arthritis model, where
Figure 57B:
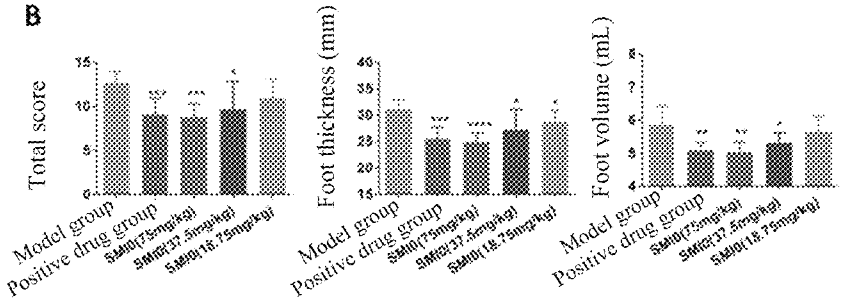
Figure 58A:
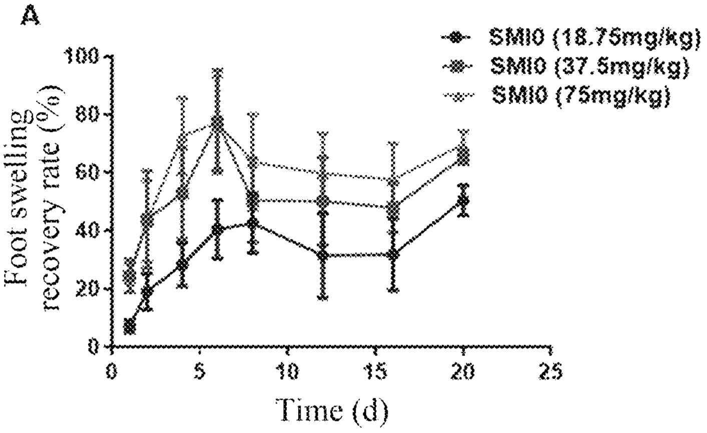
FIGS. 58A-58B show a dose-response relationship of the compound SMI0 for resisting rheumatoid arthritis, where
Figure 58B:
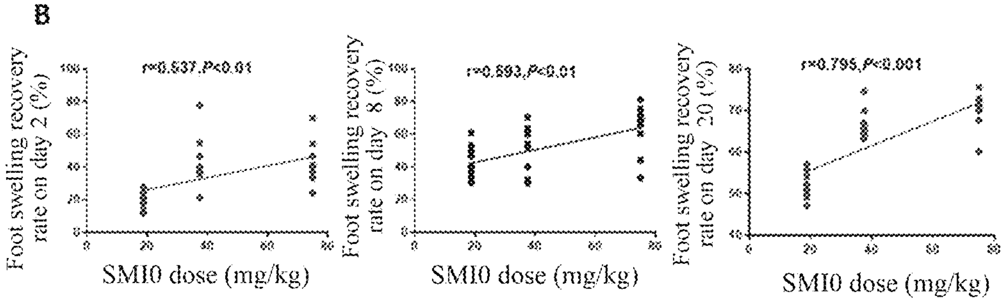

Experimental results: Compared with the model group, the foot swelling degrees in the SMI0 (75 mg/kg, 37.5 mg/kg, and 18.75 mg/kg) groups were significantly reduced on day 21, where the SMI0 (75 mg/kg) group had the optimal foot swelling improvement effect, which was similar to the swelling change in the 5 mg/kg celecoxib group (as shown in FIGS. 57A-57B); and the analysis of a correlation between an SMI0 dose and a foot swelling alleviation rate showed that the anti-rheumatoid arthritis effect of SMI0 exhibited a significant dose-response relationship, where the SMI0 dose was moderately correlated with the foot swelling alleviation rate ($P<0.01$) from day 2 to day 8, and the SMI0 dose was strongly correlated with the foot swelling alleviation rate on day 8 to day 20 ($P<0.001$) (as shown in FIGS. 58A-58B), indicating that SMI0 can significantly alleviate the foot swelling in the collagen-induced rheumatoid arthritis rat model, which is dose-dependent.

(3) Inhibition of SMI0 on CFA-Induced Rheumatoid Arthritis in Rats

Experimental method: An SD rat rheumatoid arthritis model was constructed with CFA (0.1 mL/rat). The SMI0 intervention group was divided into an ultra-low-dose group, a low-dose group, a medium-dose group, and a high-dose group, which were intragastrically administered with the compound SMI0 respectively at 1 mg/kg, 6 mg/kg, 30 mg/kg, and 150 mg/kg every day starting from two days before modeling; and the positive control group was intragastrically administered with celecoxib at 5 mg/kg. 10 animals were provided for each group. 1 d before administration of CFA to the rats, the above grouping and doses were adopted, and then the rats were administered once every day until the modeling was completed on day 10. Each rat was administered with CFA at a sole of a right hindfoot. A volume of each of the right hindfeet of rats was measured every day by a rat foot swelling measuring instrument (which was measured every 12 h in the first 3 days). A foot swelling rate of each rat was calculated according to a change of a right hindfoot volume of the rat relative to a hindfoot volume of the rat before the CFA administration at each time point, and a difference in foot swelling rate between groups of rats was analyzed.

Figure 59:
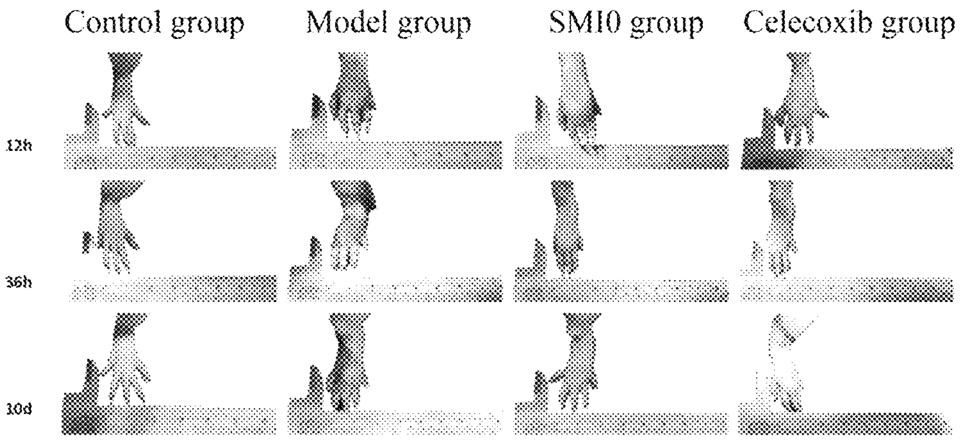
FIG. 59 shows general pictures of feet of complete Freund's adjuvant (CFA)-induced rat rheumatoid arthritis models under the inhibition of the compound SMI0.

Experimental results: Compared with the control group, the feet of rats in the model group were significantly swollen (as shown in FIG. 59); compared with the model group, the rat foot swelling caused by CFA was significantly alleviated in the SMI0 intervention group (as shown in FIG. 59, FIGS. 60B-60D, FIG. 60B shows the 24 h rat foot swelling rate, FIG. 60C shows the 36 h rat foot swelling rate, and FIG. 60D shows the 48 h rat foot swelling rate) (*$P<0.001$ vs the model group); the compound SMI0 at 1 mg/kg, 6 mg/kg, 30 mg/kg, and 150 mg/kg exhibited rat foot swelling alleviation rates respectively of 20.8%, 34.2%, 44.1%, and 52.5% at 36 h (a time point when the maximum foot swelling degree was reached in the model group); and there was a prominent dose-response relationship between the SMI0 dose and the rat foot swelling alleviation rate ($P<0.05$) (as shown in FIGS. 61A-61D, FIG. 61B shows the 24 h dose-response relationship, FIG. 61C shows the 36 h dose-response relationship, and FIG. 61**D shows the 48 h dose-response relationship), indicating that SMI0 can significantly alleviate the foot swelling in the CFA-induced rheumatoid arthritis rat model.

(4) Correlation Between CYP2E1 Activity and Rheumatoid Arthritis Severity in Rats after SMI0 Inhibition Experimental method: A calcium precipitation method was used to prepare a liver microsome of a collagen-induced rheumatoid arthritis rat model, and a Braford method was used to determine a protein concentration in the microsome. An incubation system was prepared with 2×PBS, a CZX solution, and the liver microsome at a final concentration of 0.5 mg/mL, and then pre-incubated at 37° C. for 5 min; NADPH was added to initiate a reaction, and a resulting mixture was incubated at 37° C. for 30 min and then placed on ice to terminate the reaction; and ethyl acetate was added to extract 6-hydroxychlorzoxazone, a resulting mixture was vortexed and centrifuged, and a resulting upper organic phase was collected and blow-dried with nitrogen. A peak area of a CZX metabolite 6-hydroxychlorzoxazone was detected by HPLC under the following conditions: methanol:water=56:44, and detection wavelength: 287 nm. A concentration A C of the metabolite 6-hydroxychlorzoxazone was calculated through substitution into a standard curve; and a reaction rate of conversion of CZX into 6-hydroxychlorzoxazone was calculated according to $V(pmol/min/mg)=(\Delta C*1000)/(B*T)$ to evaluate an enzymatic activity of CYP2E1, where B represents a protein concentration of the microsome (mg/mL) and T represents an incubation time (min). The correlation between the CYP2E1 activity and the rheumatoid arthritis severity in rats was analyzed.

Figure 62A:
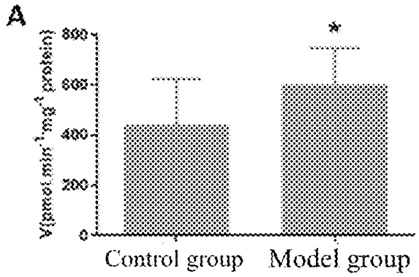
FIGS. 62A-62B show a change of CYP2E1 activity and a correlation of CYP2E1 activity with a foot swelling severity in rheumatoid arthritis rat models, where
Figure 62B:
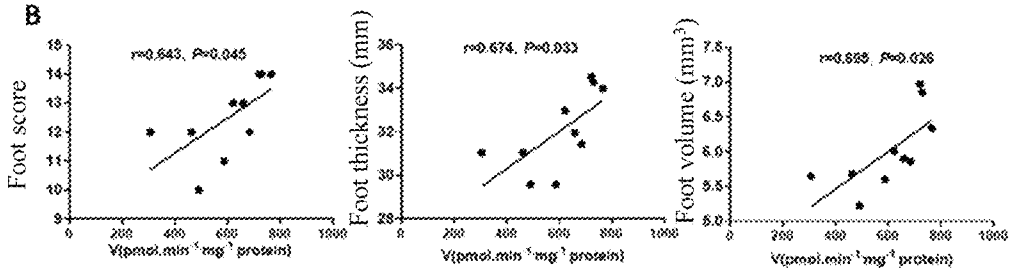
Figure 63A:
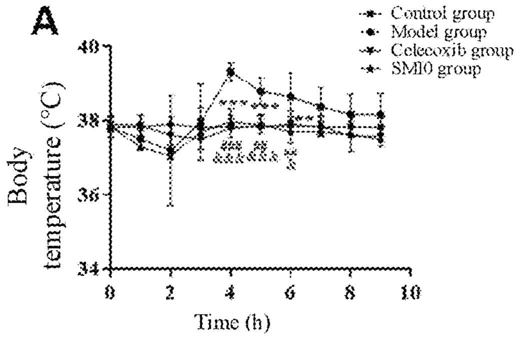
FIGS. 63A-63B show the inhibition of the compound SMI0 on a body temperature change in LPS-induced rat sepsis models, where
Figure 63B:
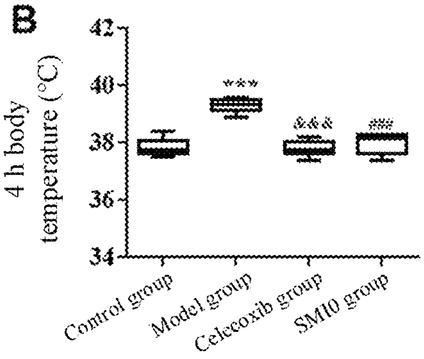
Figure 63C:
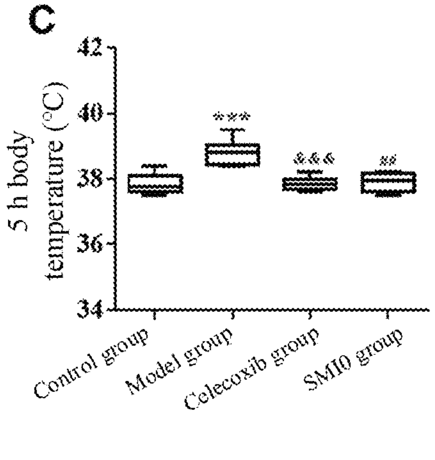
FIG. 63C shows a body temperature of rats in each group at 5 h.
Figure 63D:
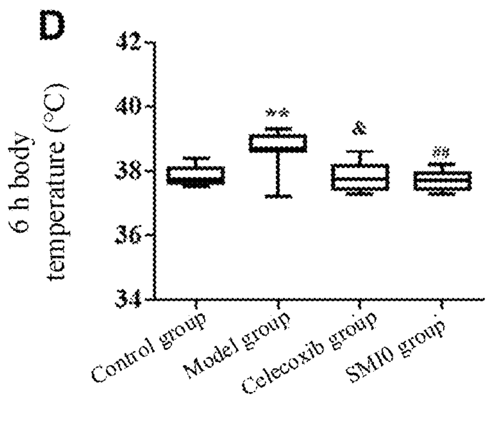
FIG. 63D shows a body temperature of rats in each group at 6 h.
Figure 64A:
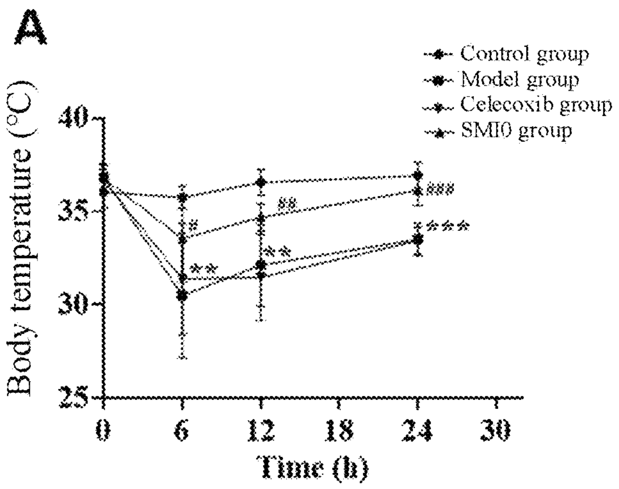
FIGS. 64A-64D show the inhibition of the compound SMI0 on a body temperature change in LPS-induced mouse sepsis models, where
Figure 64B:
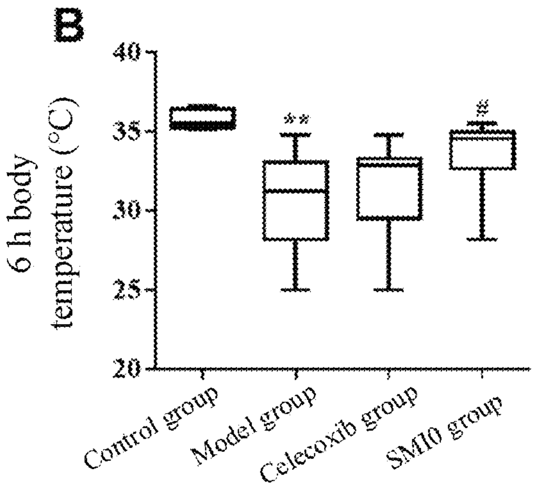
Figure 64C:
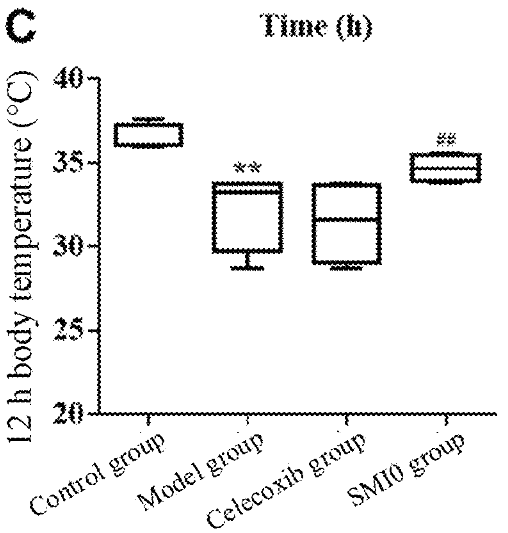
Figure 64D:
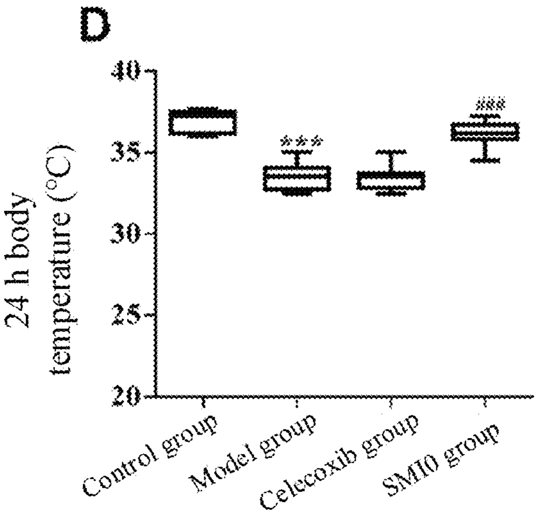
Figure 65A:
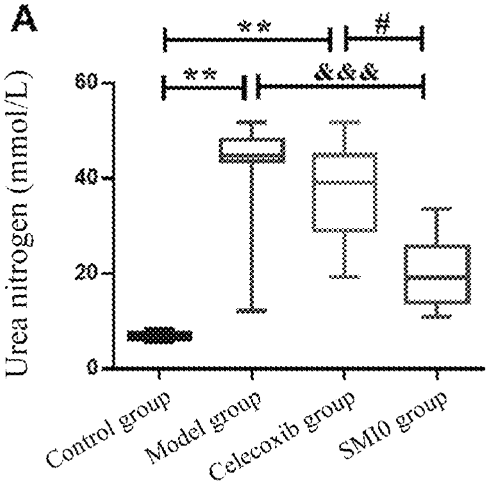
FIGS. 65A-65D show an improvement effect of the compound SMI0 on renal and cardiac function impairment in LPS-induced mouse sepsis models, where
Figure 65B:
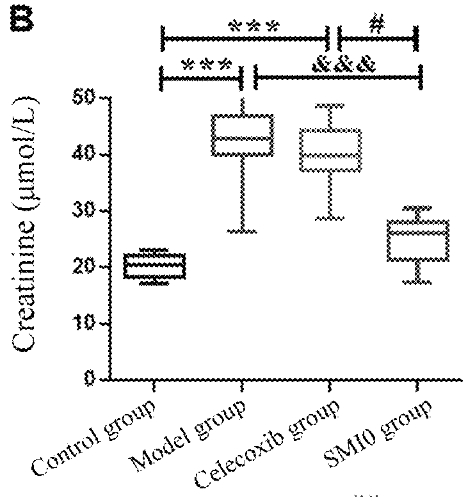
Figure 65C:
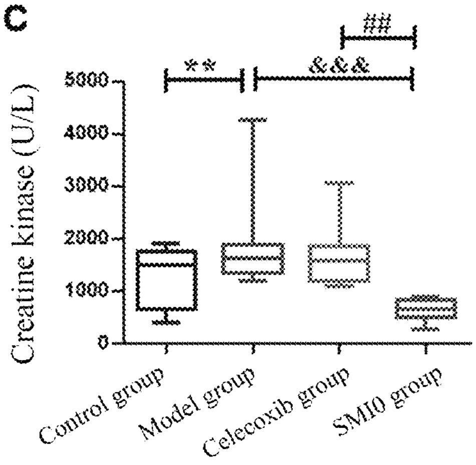
Figure 65D:
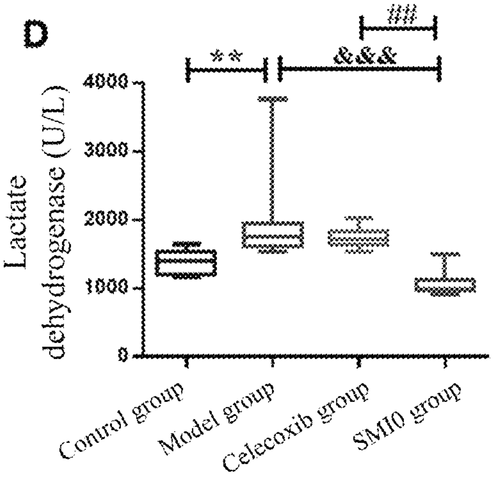

Experimental results: Compared with the control group, in the model group, the CYP2E1 activity was significantly increased ($P<0.05$, FIG. 62A), and the metabolic activity of CYP2E1 was significantly correlated with the arthritis score and the foot swelling thickness and volume ($P<0.05$, as shown in FIG. 62B), indicating that the enzymatic activity of CYP2E1 is positively correlated with the rheumatoid arthritis severity in rats, and the anti-rheumatoid arthritis effect of SMI0 may be related to the inhibition on enzymatic activity of CYP2E1.

It can be seen from the above results that SMI0 has a significant prevention and treatment effect on collagen and CFA-induced rheumatoid arthritis in rats, indicating that the compound SMI0 can be used for the prevention and treatment of clinical rheumatic and rheumatoid arthritis.

Example 20 Inhibition of SMI0 on LPS-Induced Sepsis in Rats and Mice

Experimental Method

Rats: An SD rat sepsis model was constructed through single intraperitoneal injection of LPS (5 mg/kg). 30 min before LPS administration, rats in the model group were administered with NS (0.5 mL/kg, i.g.), rats in the positive control group were administered with celecoxib (5 mg/kg, i.g.), and rats in the CYP2E1 inhibition group were administered with the compound SMI0 (150 mg/kg, i.g.). After LPS administration, a body temperature of each rat was measured and recorded every hour until 9 h (control group, n=8 rats; model group, n=10 rats; celecoxib group, n=10 rats; and SMI0 compound group, n=10 rats).

Mice: A mouse sepsis model was constructed through single intraperitoneal injection of LPS (15 mg/kg). 30 min before LPS administration, mice in the model group were administered with NS (0.5 mL/kg, i.g.), mice in the positive control group were administered with celecoxib (5 mg/kg, i.g.), and mice in the CYP2E1 inhibition group were administered with the compound SMI0 (90 mg/kg, i.g.). A body temperature of each mouse was measured and recorded at 6 h, 12 h, and 24 h after LPS administration, and the body temperature was measured 10 times in total throughout the experimental process. The animals were sacrificed at 24 h, blood samples were collected, and renal and cardiac function-associated indexes were determined (control group, n=8 mice; model group, n=8 mice; celecoxib group, n=8 mice; and SMI0 compound group, n=10 mice).

Experimental Results

Rats: Compared with the control group, the body temperature was increased significantly at 4 h, 5 h, and 6 h in the model group; and compared with the model group, the increase in body temperature in the LPS-induced sepsis rat model was avoided in the SMI0 compound group and the positive drug group (FIGS. 63A-63D, P<0.01 and *P<0.001 vs the control group; and $^{\#}$P<0.05, $^{\#\#}$P<0.01, and $^{\#\#\#}$P<0.001 vs the model group), indicating that the SMI0 intervention can significantly inhibit the LPS-induced increase in body temperature of a rat and can maintain a body temperature of a rat normal.

Mice: Compared with the control group, the body temperature was significantly reduced at 6 h, 12 h, and 24 h in the model group; compared with the model group, the decrease in body temperature in the LPS-induced sepsis mouse model was avoided in the SMI0 compound group; compared with the control group, the body temperature at 6 h, 12 h, and 24 h was significantly lower than that before LPS administration in the model group (FIGS. 64A-64D, P<0.01 and *P<0.001 vs the control group; $^{\&}$P<0.05 and $^{\&\&\&}$P<0.001 vs the model group; and $^{\#\#}$P<0.01 and $^{\#\#\#}$P<0.001 vs the celecoxib group); compared with the control group, the levels of renal function indexes urea nitrogen and creatinine and cardiac function indexes CK and LDH were significantly increased in the model group; and compared with the model group, the levels of renal and cardiac function-associated indexes were significantly reduced in the SMI0 compound group (FIGS. 65A-65D, P<0.01 and *P<0.001 vs the control group; $^{\&\&\&}$P<0.001 vs the model group; and $^{\#}$P<0.01 and $^{\#\#}$P<0.001 vs the celecoxib group), indicating that the SMI0 intervention can significantly inhibit the LPS-induced decrease in body temperature of a mouse, maintain a body temperature of a mouse normal, and improve the renal and cardiac function impairment in the LPS-induced sepsis mouse model.

It can be seen from the above results that SMI0 can avoid a body temperature change in LPS-induced sepsis rat and mouse models. It is speculated that the compound SMI0 can be used for the prevention and treatment of clinical sepsis.

Example 21 Improvement of SMI0 for Cognitive Dysfunction in an STZ-Induced AD Rat Model Experimental method: A male SD rat AD model was constructed through bilateral intracerebroventricular injection of STZ, where STZ was injected at 3 mg/kg on day 1 and STZ was injected at 1.5 mg/kg on day 3. STZ was injected into bilateral cerebral ventricles (0.9 mm posterior to the anterior fontanelle, 1.5 mm at the left or right of the sagittal suture, and below the brain surface and 3.8 mm to the skull) by a brain stereotaxic instrument. The sham-operated group was injected with a same volume of a control solvent according to same operations. The low-dose and high-dose prevention and treatment groups were intragastrically administered with the compound SMI0 respectively at 10 mg/kg and 30 mg/kg starting from day 11 after modeling, and the administration was conducted consecutively for 21 d. On day 14 of the continuous administration (that is, on day 25 of modeling), the Morris water maze (MWM) was used to conduct spatial positioning navigation training consecutively for 6 d, and a spatial exploration experiment was conducted 24 h after the spatial positioning navigation training was completed (15 rats in each group).

Figure 66A:
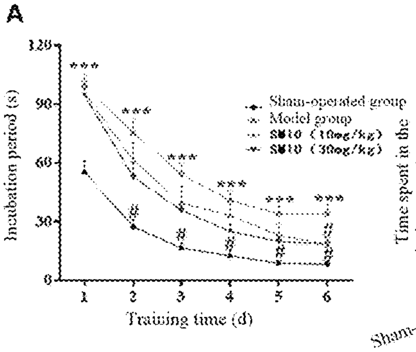
FIGS. 66A-66C show the improvement of the compound SMI0 on cognitive dysfunction in streptozotocin (STZ)-induced rat AD models, where
Figure 66B:
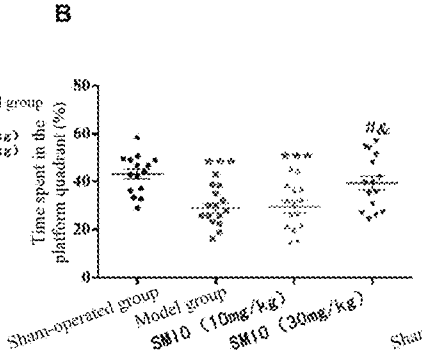
Figure 66C:
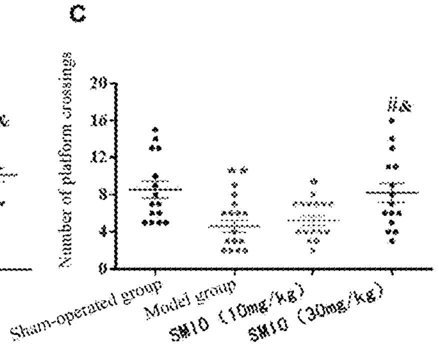

Experimental results: On day 1 to day 6 of the MWM positioning navigation experiment, the incubation period of rats in the model group was significantly extended compared with the sham-operated group; on day 2 to day 6, the incubation period of rats in the SMI0 high-dose group was significantly shortened every day compared with the model group (Table 3 shows the quantification results of parameters related to improvement of the compound SMI0 on cognitive dysfunction in the STZ-induced AD rat model; and as shown in Table 3 and FIG. 66A, *P<0.05, P<0.01, and *P<0.001 vs the sham-operated group, and $^{\#}$P<0.05 vs the model group); on day 7 of the spatial exploration experiment, compared with the sham-operated group, the residence time in a quadrant of the original platform and the number of platform crossings were significantly shortened in the model group (P<0.01 and *P<0.001 vs the sham-operated group); compared with the model group, the residence time in a quadrant of the original platform and the number of platform crossings were significantly increased in the SMI0 high-dose group (30 mg/kg) (as shown in Table 3 and FIGS. 66B-66C, #P<0.05 vs the model group); and compared with the SMI0 low-dose group, the number of platform crossings and the residence time in a quadrant of the original platform were significantly increased in the SMI0 high-dose group (&p K 0.05 vs the low-dose group); and in terms of the overall acquisition of a learning and memory function, compared with the model group, the ICV-STZ-induced cognitive dysfunction was significantly improved in the SMI0 high-dose group, with an improvement rate of 46.7%; and there was an improvement trend in the SMI0 low-dose group, without a significant statistical difference and with an improvement rate of 32.6%, indicating that SMI0 can significantly improve the cognitive dysfunction induced by lateral intracerebroventricular injection of STZ.

TABLE 3

Quantification results of parameters related to improvement of the compound SMI0 on cognitive dysfunction in the STZ-induced AD rat model

| Group | n | Incubation period (s) Day 1 | Day 2 | Day 3 | Day 4 | Day 5 | Day 6 | Time spent in the platform quadrant (%) | Number of crossing platform |
|---|---|---|---|---|---|---|---|---|---|
| Sham-operated group | 15 | 55.2 ± 5.4 | 27.4 ± 3.3 | 16.6 ± 2.2 | 12.7 ± 2.9 | 8.9 ± 1.4 | 8.4 ± 1.4 | 43.1 ± 2.0 | 8.5 ± 0.9 |
| Model group | 15 | 99.1 ± 5.6*** | 75.3 ± 7.1*** | 54.0 ± 5.6*** | 40.9 ± 5.0*** | 34.0 3.7*** | 34.0 ± 4.3*** | 28.8 ± 1.9*** | 4.5 ± 0.6** |
| SMI0 (10 mg/kg) | 15 | 95.7 ± 5.8*** | 61.1 ± 8.7** | 39.5 ± 8.0** | 33.2 ± 7.3** | 23.1 ± 5.8* | 18.5 ± 3.9*$^{\#}$ | 29.4 ± 2.4*** | 5.1 ± 0.5* |
| SMI0 (30 mg/kg) | 15 | 94.6 ± 4.3*** | 52.7 ± 7.2*$^{\#}$ | 35.9 ± 4.0*$^{\#}$ | 25.2 ± 3.4$^{\#}$ | 20.0 ± 3.2$^{\#}$ | 18.6 ± 3.2*$^{\#}$ | 39.3 ± 2.8$^{\#\&}$ | 8.2 ± 1.0$^{\#\&}$ |

It can be seen from the above results that SMI0 at 30 mg/kg can significantly improve the cognitive dysfunction in the STZ-induced AD rat model. It is speculated that the compound SMI0 can be used for the prevention and treatment of clinical AD.

Example 22 Inhibition of SMI0 on Focal CIRI in Rats

Experimental method: A focal CIRI rat model with middle cerebral artery occlusion (MCAO) was constructed by a modified *Zea-longa* suture-occluded method. A rat was intraperitoneally injected with 10% chloral hydrate for anaesthetization, and fixed on a thermostatic plate in a supine position such that a body temperature of the rat was maintained at 36.5° C. to 37.5° C.; the skin in the middle of the neck was disinfected with iodophor and then cut to expose the left common carotid artery (CCA), the CCA, external carotid artery (ECA), and internal carotid artery (ICA) were separated, and the pterygopalatine artery was ligated; a small incision was provided at a side of the ECA, and a nylon suture was inserted through the incision; with a fork route junction as a mark, the nylon suture was carefully and slowly pushed forwards when inserted by about 17 mm, and a resistance was felt at about 18±0.5 mm, indicating that an end of the nylon suture had reached the anterior cerebral artery (ACA); the incision of the ECA was tightened, and the skin was sutured; 2 h after ischemia, the rat was anesthetized with inhalation sevoflurane, and the nylon suture was gently and slowly pulled out until a ball end of the nylon suture reached a bifurcation of the CCA, thereby achieving reperfusion; 2 h after ischemia, the reperfusion was conducted for 24 h, where 10 min before reperfusion, the SMI0 intervention group was intragastrically administered with the compound SMI0 (150 mg/kg), and the sham-operated group and the model group each were injected with an equal volume of a control solvent; neurobehavioral scoring was conducted at 2.5 h and 6 h after surgery; and 24 h after the reperfusion, the rat was decapitated, a brain tissue was collected and stained with triphenyltetrazolium chloride (TTC), and the changes of the cerebral infarction volume and cerebral edema were observed (10 rats in each group).

Figure 67:
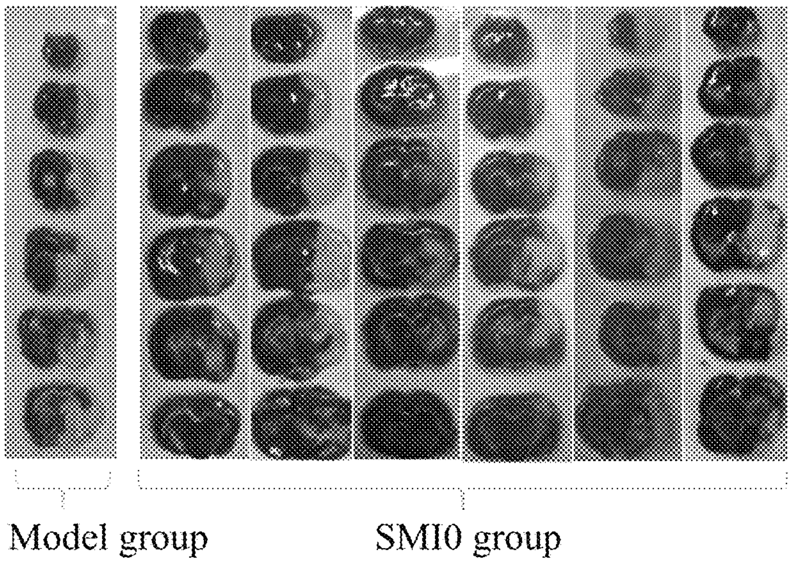
FIG. 67 shows an inhibitory effect of the compound SMI0 on focal cerebral ischemia-reperfusion injury (CIRI) in rats.
Figure 68A:
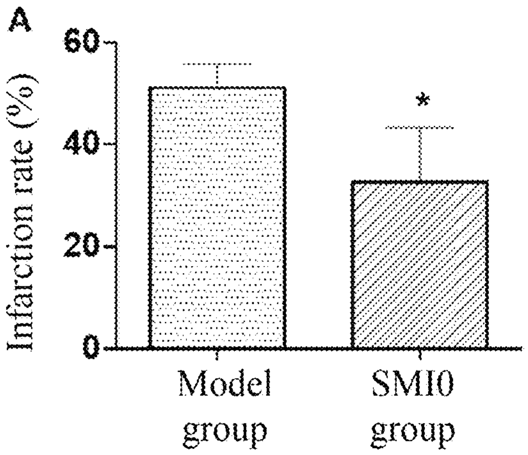
FIGS. 68A-68B show the inhibition of the compound SMI0 on cerebral infarction and cerebral edema caused by focal CIRI in rats, where
Figure 68B:
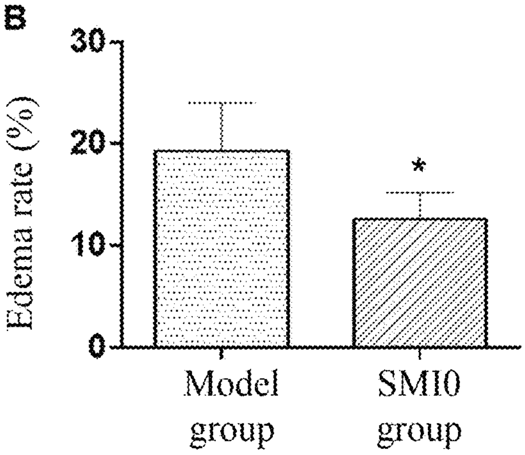

Experimental results: Compared with the model group, the cerebral infarction volume and cerebral edema volume were significantly reduced in the SMI0 intervention group (as shown in FIG. 67 and of FIGS. 68A-68B, *P<0.05 vs the model group), where the cerebral infarction volume was reduced from 51.03% in the model group to 32.62%, the cerebral edema volume was reduced from 19.25% in the model group to 12.63%, and inhibition rates of SMI0 (150 mg/kg) on the cerebral infarction volume and cerebral edema volume were 36.06% and 34.39% respectively, indicating that SMI0 can significantly reduce the cerebral infarction volume and cerebral edema volume in the focal CIRI rat model with MCAO.

It can be seen from the above results that SMI0 can significantly improve the cerebral infarction and cerebral edema in the focal CIRI rat model. It is speculated that the compound SMI0 can be used for the prevention and treatment of clinical ischemic stroke.

Example 23 Reduction of SMI0 in a Blood Lipid Level of a Hyperlipidemia ApoE−/− Mouse Model Induced by a High-Fat Diet Experimental method: ApoE−/− mice were fed with a high-fat and high-cholesterol feed to construct an ApoE−/− mouse hyperlipidemia model. An SMI0 intervention group was divided into a low-dose intervention group and a high-dose intervention group, which were administered with the compound SMI0 at 30 mg/kg and 150 mg/kg every day from the beginning of modeling to the end of the 16-week modeling. At the end of the experiment, blood was collected from the orbit, and the levels of blood lipid-associated indexes in the serum of each mouse were determined by an automatic biochemical analyzer (8 mice in each group).

Figure 69:
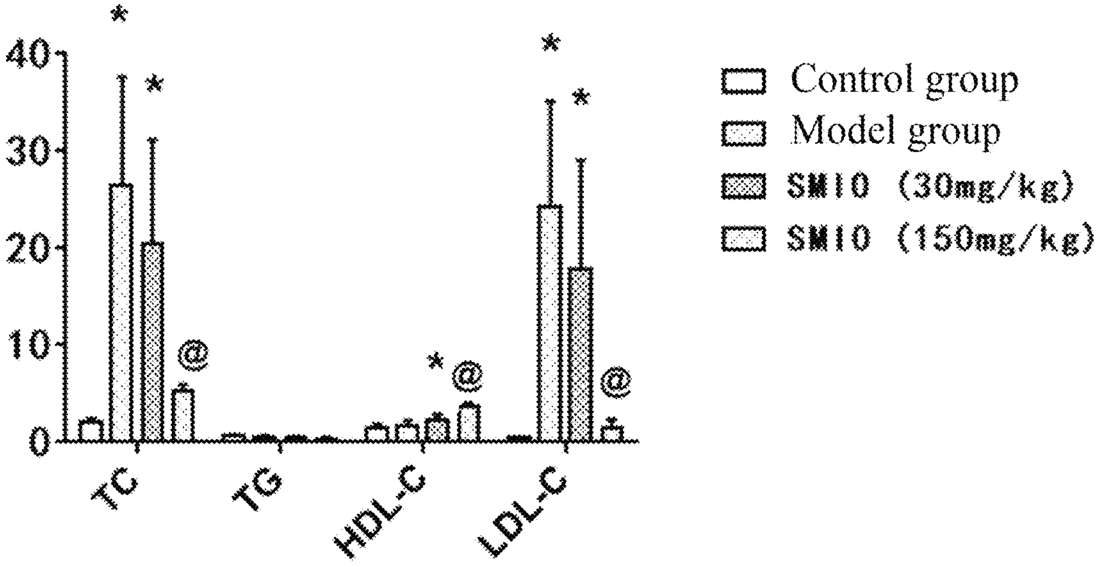
FIG. 69 shows that the compound SMI0 can reduce a blood lipid level in ApoE−/− mouse hyperlipidemia models induced by a high-fat diet.
Figure 70A:
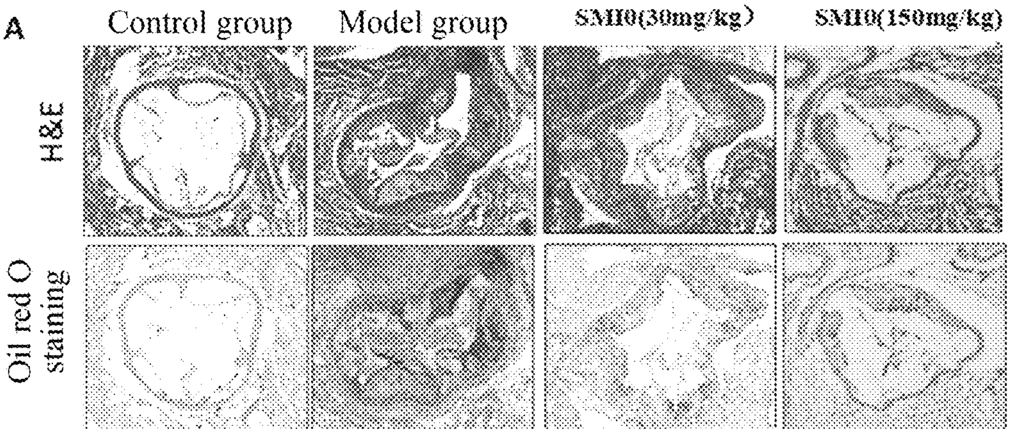
FIGS. 70A-70B show an inhibitory effect of the compound SMI0 on the formation of aortic atherosclerotic plaques in ApoE−/− mice induced by a high-fat diet, where
Figure 70B:
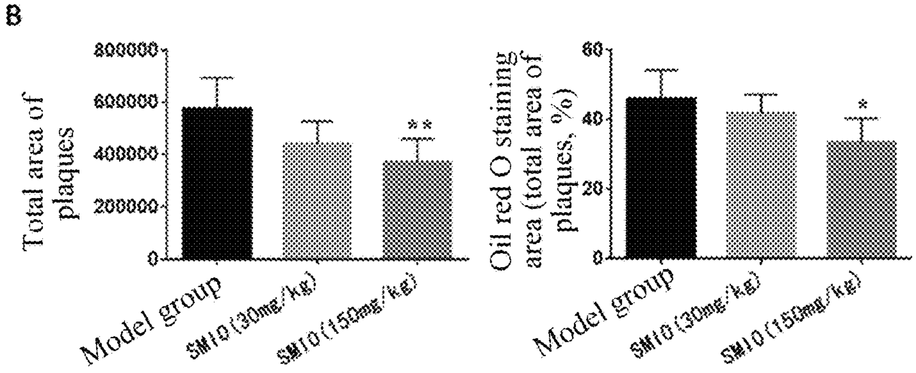

Experimental results: Compared with the control group, the levels of total cholesterol (TC) and low-density lipoprotein (LDL) in mice of the model group were significantly increased (as shown in Table 4 and FIG. 69, *P<0.05 vs the control group); compared with the model group, in the SMI0 high-dose intervention group, the levels of TC and LDL were significantly reduced, and the level of high-density lipoprotein (HDL) was significantly increased (@P<0.05 vs the model group); and compared with the model group, the high blood lipid level induced by the high-fat diet was improved to some extent in the SMI0 low-dose intervention group, without statistical significance. In addition, the SMI0 administration significantly inhibited the formation of aortic atherosclerotic plaques in ApoE−/− mice. HE staining results showed that, compared with the model group, the total area of aortic root lesions in mice was significantly reduced in the SMI0 high-dose group (150 mg/kg) (as shown in FIGS. 70A-70B, **P<0.01 vs the model group); and oil red O staining results also showed that the total area of aortic root lesions was significantly reduced in the SMI0 high-dose group (150 mg/kg) (as shown in FIGS. 70A-70B, *P<0.05 vs the model group), indicating that the administration of SMI0 at 150 mg/kg can significantly improve the high blood lipid level induced by the high-fat diet (decreasing the TC and LDL levels and increasing the HDL level) while inhibiting the formation of aortic atherosclerotic plaques in ApoE−/− mice.

TABLE 4

Quantification results of parameters related to reduction of the compound SMI0 in a blood lipid level in the hyperlipidemia mouse model induced by the high-fat diet

| Group | n | Total cholesterol (mmol/L) | Triglyceride (mmol/L) | High-density lipoprotein (mmol/L) | Low-density lipoprotein (mmol/L) |
|---|---|---|---|---|---|
| Control group | 8 | 2.03 ± 0.45 | 0.64 ± 0.15 | 1.43 ± 0.42 | 0.45 ± 0.10 |
| Model group | 8 | 26.43 ± 10.23* | 0.57 ± 0.14 | 1.77 ± 0.46 | 24.26 ± 9.93* |
| SMI0 (30 mg/kg) | 8 | 20.45 ± 10.77* | 0.56 ± 0.04 | 2.37 ± 0.49* | 17.94 ± 11.16* |
| SMI0 (150 mg/kg) | 8 | 5.35 ± 0.55@ | 0.40 ± 0.10 | 3.68 ± 0.33*@ | 1.50 ± 0.77@ |

It can be seen from the above results that SMI0 can significantly reduce the increase in blood lipid level and the formation of atherosclerotic plaques in mice caused by the high-fat diet. It is speculated that the compound SMI0 can be used for the prevention and treatment of clinical hyperlipidemia, AS, and CHD.

Example 24 Reduction of SMI0 in a Blood Glucose Level in a Diabetes Rat Model Induced by a High-Fat Diet and STZ Experimental method: A diabetes rat model was constructed by a high-fat diet+single intraperitoneal injection of STZ (40 mg/kg). AFBG level of higher than or equal to 16.7 mmol/L after two weeks of molding was a criterion for successful molding. Modeled rats were divided into various groups according to the blood glucose level. Rats in a model group were administered with NS, and rats in SMI0 low-dose and high-dose intervention groups were administered with the compound SMI0 at 30 mg/kg and 150 mg/kg every day, respectively. The FBG level in rats was determined and recorded regularly every week until the sixth week after administration. 10 rats were provided in each group.

Figure 71A:
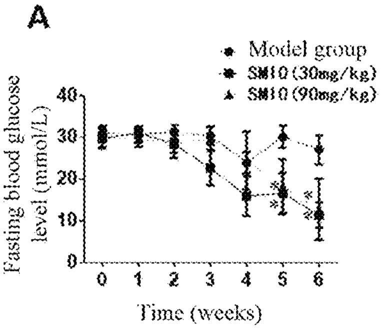
FIGS. 71A-71C show that the compound SMI0 can reduce a blood glucose level in diabetes rats induced by a high-fat diet and STZ, where
Figure 71B:
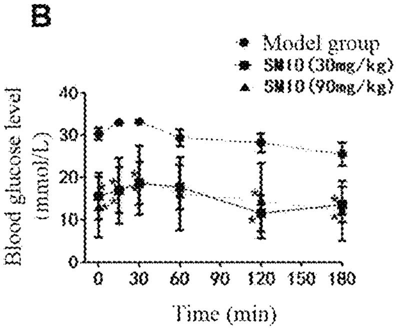
Figure 71C:
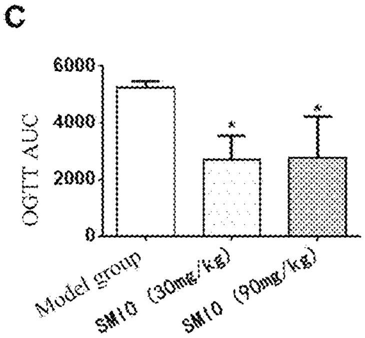

Experimental results: Compared with the model group, FBG levels in rats in the SMI0 low-dose and high-dose intervention groups at weeks 5 and 6 were significantly reduced (*P<0.05 vs the model group) (FIG. 71A); and glucose tolerance test results showed that the glucose tolerance of rats in the SMI0 low-dose and high-dose intervention groups was significantly improved (FIGS. 71B-71C), indicating that the SMI0 intervention can significantly improve the high blood glucose level in rats induced by a high-fat diet and STZ.

It can be seen from the above results that SMI0 can significantly reduce a blood glucose level in diabetes rats induced by a high-fat diet and STZ. It is speculated that the compound SMI0 can be used for the prevention and treatment of clinical diabetes.

Example 25 Increase in Expression of CYP2E1 in a Paracancerous Tissue of Bladder Cancer Experimental method: The changes of CYP2E1 expression in paracancerous tissues of 30 clinical bladder cancer patients were investigated with bladder tissues of 30 healthy individuals as a control, and the changes of CYP2E1 contents in the paracancerous tissues of the bladder cancer patients were determined.

Figure 72:
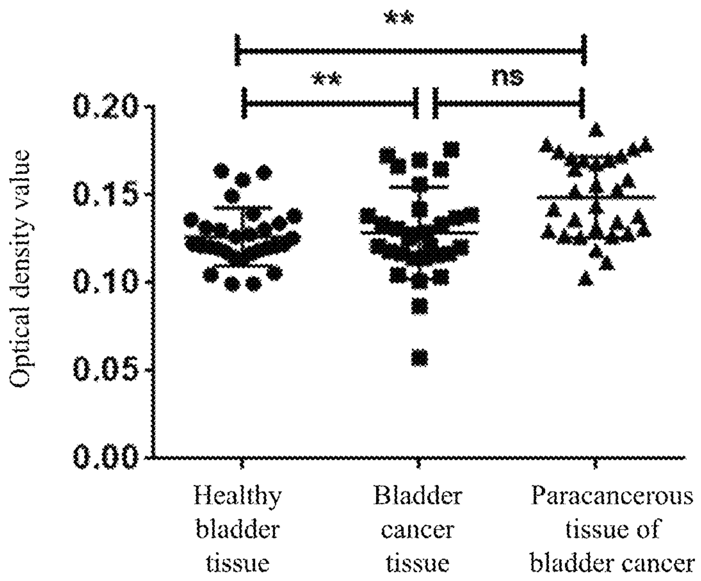
FIG. 72 shows a high expression level of CYP2E1 in a paracancerous tissue of bladder cancer.

Experimental results: Immunohistochemical results showed that the expression of CYP2E1 in the paracancerous tissue of bladder cancer was significantly higher than that in the healthy bladder tissue (P<0.05), as shown in FIG. 72.

Since the expression of CYP2E1 in lung cancer, liver cancer, and glioma can be significantly increased, CYP2E1 can play a role in inflammation-associated tumors, and the compound SMI0 can significantly inhibit the occurrence and development of lung cancer, liver cancer, and glioma, it is speculated that the increased expression of CYP2E1 in the paracancerous tissue of bladder cancer is related to the occurrence of bladder cancer, the compound SMI0 can have a prevention and treatment effect on the occurrence and development of bladder cancer, and the compound SMI0 can be used for the prevention and treatment of clinical bladder cancer.

Example 26 Increase in Expression of CYP2E1 in a Paracancerous Tissue of Gallbladder Cancer Experimental method: The changes of CYP2E1 expression in paracancerous tissues of 33 clinical gallbladder cancer patients were investigated with gallbladder tissues of 31 healthy individuals as a control.

Figure 73:
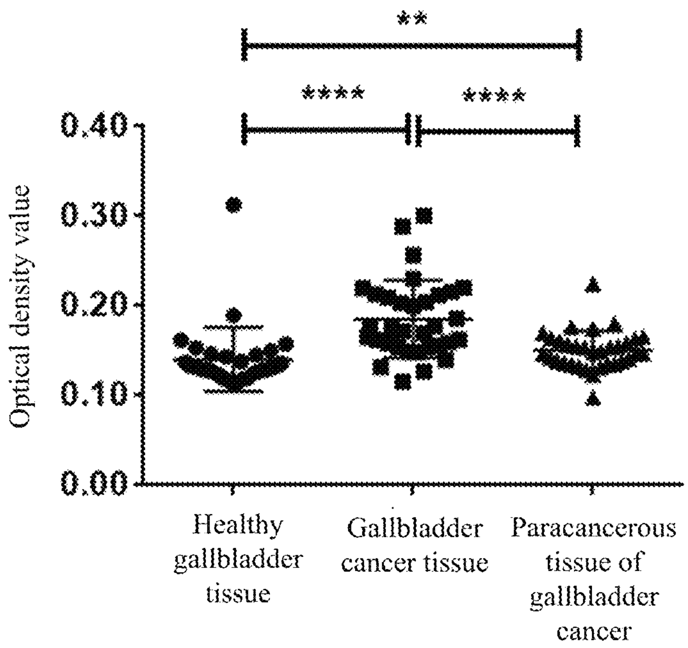
FIG. 73 shows a high expression level of CYP2E1 in a paratumoral tissue of gallbladder cancer.

Experimental results: Immunohistochemical results showed that the expression of CYP2E1 in the paracancerous tissue of gallbladder cancer was significantly higher than that in the healthy gallbladder tissue (P<0.05), as shown in FIG. 73. Since the expression of CYP2E1 in lung cancer, liver cancer, and glioma can be significantly increased, CYP2E1 can play a role in inflammation-associated tumors, and the compound SMI0 can significantly inhibit the occurrence and development of lung cancer, liver cancer, and glioma, it is speculated that the increased expression of CYP2E1 in the paracancerous tissue of gallbladder cancer is related to the occurrence of gallbladder cancer, the compound SMI0 can have a prevention and treatment effect on the occurrence and development of gallbladder cancer, and the compound SMI0 can be used for the prevention and treatment of clinical gallbladder cancer.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A method of inhibiting a CYP2E1, comprising: using one or more compounds or a salt thereof as a CYP2E1 inhibitor to inhibit the CYP2E1, wherein the one or more compounds or a salt thereof target and bind to the CYP2E1, and the one or more compounds are selected from the group consisting of

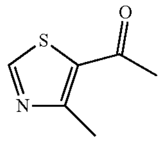
,
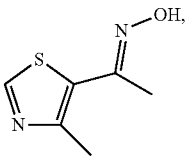

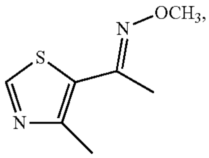

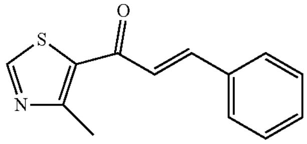
,
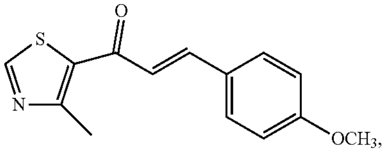

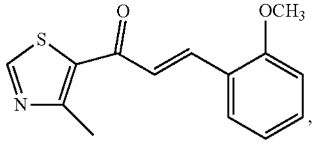
,
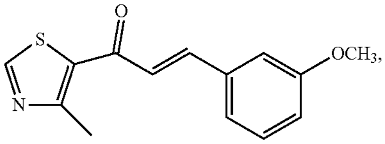

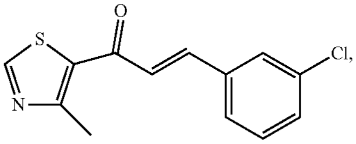

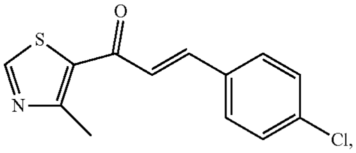

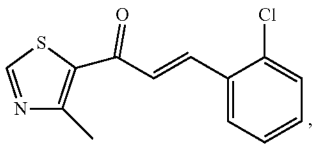
,
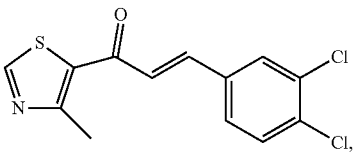

-continued

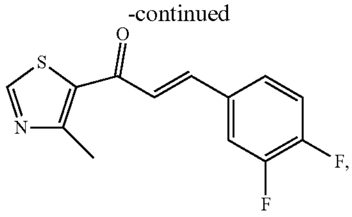

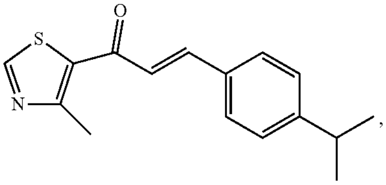
,
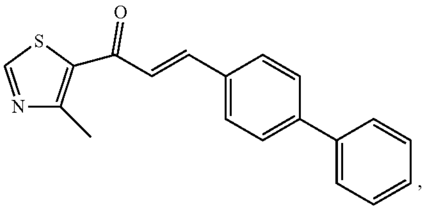
,
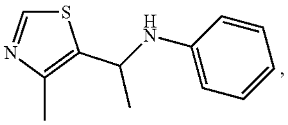
,
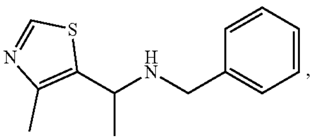
,
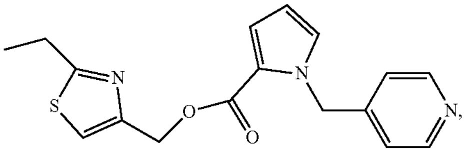

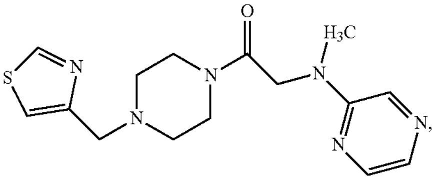

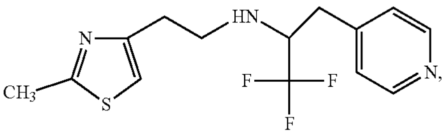

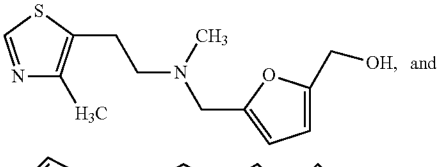
and
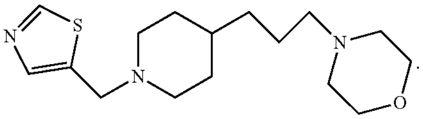
.

2. The method according to claim 1, comprising:

using at least one selected from the group consisting of the following compounds as the CYP2E1 inhibitor to inhibit the CYP2E1, wherein the at least one selected from the group consisting of the following compounds targets and binds to the CYP2E1:

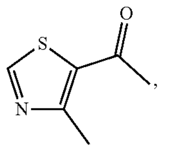

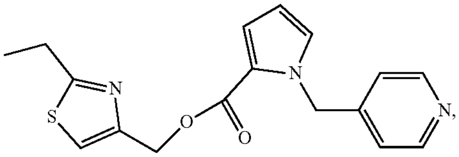

and

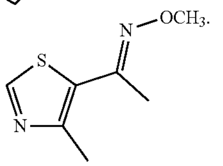

3. The method according to claim 1, wherein the compound reacts with an acid to obtain an acid salt of the compound as the CYP2E1 inhibitor to inhibit the CYP2E1; and the acid is at least one selected from the group consisting of an inorganic acid and an organic acid;

wherein the inorganic acid is at least one selected from the group consisting of hydrochloric acid, hydrobromic acid, hydroiodic acid, sulfuric acid, nitric acid, and phosphoric acid; and the organic acid is at least one selected from the group consisting of acetic acid, oxalic acid, succinic acid, tartaric acid, malic acid, lactic acid, methanesulfonic acid, p-toluenesulfonic acid, citric acid, resin acid, maleic acid, fumaric acid, salicylic acid, and acetylsalicylic acid;

wherein the compound has a structural formula of

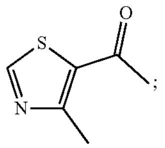

an X-ray powder diffraction (XRPD) pattern of a first crystal form of a hydrochloride of the compound comprises 3 or more 2θ values selected from the group consisting of 8.4±0.2°, 13.1±0.2°, 14.8±0.2°, 16.6±0.2°, 24.1±0.2°, 27.2±0.2°, 30.5±0.2°, 31.8±0.2°, 33.5±0.2°, 35.4±0.2°, and 35.7±0.2°; and a differential scanning calorimetry-thermogravimetric analyzer (DSC-TGA) pattern of the first crystal form of the hydrochloride of the compound comprises a significant endothermic peak at 70° C. to 220° C. and shows a thermal decomposition at 80° C. to 170° C.; and an XRPD pattern of a second crystal form of a sulfate of the compound comprises 5 or more 2θ values selected from the group consisting of 10.1±0.2°, 15.1±0.2°, 16.0±±0.2°, 16.7±0.2°, 19.2±0.2°, 19.9±0.2°, 23.4±0.2°, 24.0±0.2°, 25.8±0.2°, 26.5±0.2°, 28.9±0.2°, 30.3±0.2°, and 32.2±0.2°; and a DSC-TGA pattern of the second crystal form of the sulfate of the compound comprises at least one endothermic peak at 30° C. to 85° C., 90° C. to 160° C., or 215° C. to 330° C. and shows a thermal decomposition at 150° C. to 350° C.

4. The method according to claim 1, wherein a method for preparing the compound as the CYP2E1 inhibitor at least comprises one selected from the group consisting of the following methods:

method 1: subjecting a raw material comprising a compound selected from the group consisting of compounds with a structural formula shown in formula II, a first aprotic solvent, and a Grignard reagent to a first reaction at −20° C. to 25° C. for 0.5 h to 3 h to obtain a first CYP2E1 inhibitor, formula II

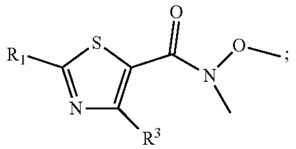

wherein the first CYP2E1 inhibitor is at least one selected from the group consisting of compounds with a structural formula shown in formula III:

formula III

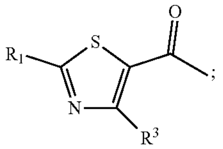

method 2: subjecting a compound with a structural formula shown in formula III and a hydroxylamine hydrochloride to a second reaction in a presence of a first alkali source to obtain a second CYP2E1 inhibitor, wherein the second CYP2E1 inhibitor is at least one selected from the group consisting of compounds with a structural formula shown in formula III-1:

formula III-1

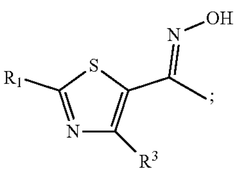

method 3: subjecting the compound with the structural formula shown in formula III and an aromatic aldehyde compound to a third reaction at 25° C. to 100° C. for 2 h to 8 h in a presence of a second alkali source to obtain a third CYP2E1 inhibitor, wherein the third CYP2E1 inhibitor is at least one selected from the group consisting of compounds with a structural formula shown in formula III-2:

formula III-2

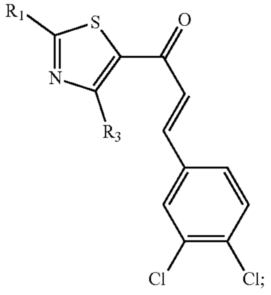

and method 4: subjecting the compound with the structural formula shown in formula III, an amine compound, and a reducing agent to a fourth reaction in a presence of a first acid source to obtain a fourth CYP2E1 inhibitor, wherein the amine compound is at least one selected from the group consisting of phenylamine and benzylamine; and the fourth CYP2E1 inhibitor is at least one selected from the group consisting of compounds with a structural formula shown in formula III-3:

formula III-3

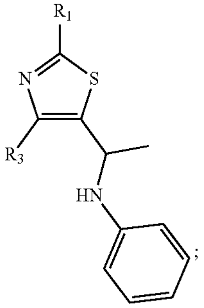

wherein in each of formula II, formula III, formula III-1, formula III-2, and formula III-3, $R_1$ is one selected from the group consisting of hydrogen, $C_1$-$C_{10}$ alkyl, and epoxyalkyl: $R_3$ is at least one selected from the group consisting of hydrogen, $C_1$-$C_{10}$ alkyl, and a second substituted $C_1$-$C_{10}$ alkyl.

5. The method according to claim 4, wherein in the method 1, the first aprotic solvent is at least one selected from the group consisting of tetrahydrofuran (THF) and diethyl ether and the Grignard reagent is at least one selected from the group consisting of methylmagnesium bromide and methylmagnesium chloride;

in the method 2, the first alkali source is at least one selected from the group consisting of potassium hydroxide, sodium hydroxide, sodium carbonate, pyridine, triethylamine (TEA), and N,N-diisopropylethylamine (DIPEA);

in the method 3, the second alkali source is at least one selected from the group consisting of sodium hydroxide, potassium hydroxide, potassium tert-butoxide, sodium methoxide, and potassium fluoride; and the aromatic aldehyde compound is at least one selected from the group consisting of p-methoxybenzaldehyde, o-methoxybenzaldehyde, m-methoxybenzaldehyde, p-chlorobenzaldehyde, o-chlorobenzaldehyde, m-chlorobenzaldehyde, p-phenylbenzaldehyde, p-isopropylbenzaldehyde, and 3,4-difluorobenzaldehyde; and in the method 4, the first acid source is at least one selected from the group consisting of formic acid, acetic acid, and hydrochloric acid; and the reducing agent is at least one selected from the group consisting of sodium cyanoborohydride, sodium borohydride, and lithium aluminum hydride (LAH);

wherein in the method 1, a molar ratio of the compound selected from the group consisting of compounds with the structural formula shown in formula II to the Grignard reagent is 1:1 to 1:3;

in the method 2, a molar ratio of the compound with the structural formula shown in formula III to the hydroxylamine hydrochloride is 1:1 to 1:6;

in the method 3, a molar ratio of the compound with the structural formula shown in formula III to the aromatic aldehyde compound is 1:1 to 1:5; and in the method 4, a molar ratio of the compound with the structural formula shown in formula III to the reducing agent is 1:1 to 1:5.

6. The method according to claim 4, wherein the compound selected from the group consisting of compounds with the structural formula shown in formula II is prepared through the following process:

subjecting a raw material comprising a compound selected from the group consisting of compounds with a structural formula shown in formula II-1, a condensing agent, N,O-dimethylhydroxylamine hydrochloride, and a second aprotic solvent to a fifth reaction at 20° C. to 60° C. for 10 h to 20 h in a presence of a third alkali source to obtain the compound selected from the group consisting of compounds with the structural formula shown in formula II, formula II-1

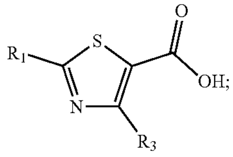

wherein the condensing agent is at least one selected from the group consisting of 1-ethyl-(3-dimethylaminopropyl)carbodiimide hydrochloride, didodecyl carbonate, N,N-carbonyldiimidazole, dicyclohexylcarbodiimide, and N-(4-carboxyphenyl) maleimide (CPMI); and the third alkali source is at least one selected from the group consisting of sodium hydroxide, potassium hydroxide, calcium hydroxide, sodium carbonate, potassium carbonate, pyridine, TEA, and DIPEA;

wherein the compound selected from the group consisting of compounds with a structural formula shown in formula II-1, the condensing agent, and the N,O-dimethylhydroxylamine hydrochloride are in a molar ratio of 1:1:1 to 1:5:5;

a preparation of the compound selected from the group consisting of compounds with a structural formula shown in formula II-1 at least comprises the following steps:

subjecting a raw material comprising a compound selected from the group consisting of compounds with a structural formula shown in formula II-2 to a hydrolysis in a presence of a fourth alkali source to obtain a mixture, and adjusting a pH of the mixture with a second acid source to 2 to 3 to obtain the compound selected from the group consisting of compounds with a structural formula shown in formula II-1, formula II-2

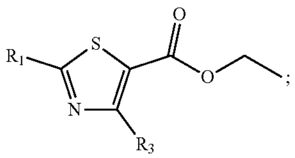

wherein the fourth alkali source is at least one selected from the group consisting of sodium hydroxide, potassium hydroxide, calcium hydroxide, sodium carbonate, and potassium carbonate;

wherein the second acid source is a concentrated hydrochloric acid; and the adjusting the pH of the mixture with the second acid source to 2 to 3 is conducted at 10° C. to 50° C.;

wherein a preparation method of an acid salt of the compound at least comprises:

subjecting a material comprising the compound and a solvent to a sixth reaction at −20° C. to 80° C. for 0.5 h to 10 h to obtain the acid salt of the compound;

wherein the solvent is at least one selected from the group consisting of an ether compound, an alcohol compound, an ester compound, a nitrile compound, a ketone compound, a haloalkane, an alkane, and an aromatic hydrocarbon;

wherein in each of formula II-1 and formula II-2, $R_1$ is one selected from the group consisting of hydrogen, $C_1$-$C_{10}$ alkyl, and epoxyalkyl: $R_3$ is at least one selected from the group consisting of hydrogen, $C_1$-$C_{10}$ alkyl, and a second substituted $C_1$-$C_{10}$ alkyl.

7. The method according to claim 1, wherein the CYP2E1 inhibitor is used in an active ingredient of a drug for treating or preventing an inflammation-mediated disease (IMD); and the IMD comprises at least one selected from the group consisting of a liver cancer, a glioma, an ovarian cancer, a lung cancer, a bladder cancer, a gallbladder cancer, a liver damage, a fatty liver, a hepatitis, a liver fibrosis, a pulmonary fibrosis, a rheumatic and rheumatoid arthritis, a sepsis, an Alzheimer's disease (AD), an ischemic stroke, a Parkinson's disease (PD), a hyperlipidemia, an atherosclerosis (AS), a coronary heart disease (CHD), and a diabetes.

* * * * *